US012649737B2

(12) United States Patent
Vaswani et al.

(10) Patent No.: US 12,649,737 B2
(45) Date of Patent: Jun. 9, 2026

(54) COMPOUNDS AND USES THEREOF

(71) Applicant: Foghorn Therapeutics Inc., Watertown, MA (US)

(72) Inventors: Rishi G. Vaswani, Lexington, MA (US); David S. Huang, Watertown, MA (US); Kevin J. Wilson, Roslindale, MA (US); Shawn E. R. Schiller, Haverhill, MA (US); Neville John Anthony, Northborough, MA (US)

(73) Assignee: FOGHORN THERAPEUTICS INC., Watertown, MA (US)

( * ) Notice: Subject to any disclaimer, the term of this patent is extended or adjusted under 35 U.S.C. 154(b) by 796 days.

(21) Appl. No.: 17/795,929

(22) PCT Filed: Jan. 29, 2021

(86) PCT No.: PCT/US2021/015878

§ 371 (c)(1),
(2) Date: Jul. 28, 2022

(87) PCT Pub. No.: WO2021/155264

PCT Pub. Date: Aug. 5, 2021

(65) Prior Publication Data

US 2023/0121497 A1 Apr. 20, 2023

Related U.S. Application Data

(60) Provisional application No. 62/967,346, filed on Jan. 29, 2020.

(51) Int. Cl.

*C07D 471/04* (2006.01)
*C07D 401/14* (2006.01)
*C07D 403/12* (2006.01)
*C07D 403/14* (2006.01)
*C07D 405/14* (2006.01)
*C07D 413/14* (2006.01)
*C07D 417/14* (2006.01)

(52) U.S. Cl.

CPC ......... *C07D 471/04* (2013.01); *C07D 401/14* (2013.01); *C07D 403/12* (2013.01); *C07D 403/14* (2013.01); *C07D 405/14* (2013.01); *C07D 413/14* (2013.01); *C07D 417/14* (2013.01)

(58) Field of Classification Search

CPC .. C07D 471/04; C07D 401/14; C07D 403/12; C07D 403/14; C07D 405/14; C07D 413/14; C07D 417/14; C07D 513/04; A61K 31/437; A61K 31/4375; A61K 31/444; A61K 31/454; A61K 31/4545; A61K 31/4725; A61K 31/497; A61K 31/5377; A61K 45/06; A61P 31/12; A61P 35/00

See application file for complete search history.

(56) References Cited

U.S. PATENT DOCUMENTS

| | | | |
|---|---|---|---|
| 2,788,341 | A | 4/1957 | Schwyzer |
| 3,717,642 | A | 2/1973 | Von Strandtmann |
| 4,109,496 | A | 8/1978 | Allemann et al. |
| 4,650,796 | A | 3/1987 | George et al. |
| 4,868,103 | A | 9/1989 | Stavrianopoulos et al. |
| 5,223,409 | A | 6/1993 | Ladner et al. |
| 5,225,422 | A | 7/1993 | Nagata et al. |
| 5,283,317 | A | 2/1994 | Saifer et al. |
| 5,631,169 | A | 5/1997 | Lakowicz et al. |
| 5,677,158 | A | 10/1997 | Zhou et al. |
| 5,801,030 | A | 9/1998 | McVey et al. |
| 5,858,358 | A | 1/1999 | June et al. |
| 5,883,223 | A | 3/1999 | Gray |
| 6,180,612 | B1 | 1/2001 | Hockensmith et al. |
| 6,309,634 | B1 | 10/2001 | Bankiewicz et al. |
| 6,352,694 | B1 | 3/2002 | June et al. |
| 6,551,786 | B2 | 4/2003 | Manfredi |
| 6,683,058 | B1 | 1/2004 | Tuszynski |
| 6,692,964 | B1 | 2/2004 | June et al. |
| 6,716,662 | B2 | 4/2004 | Akai |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 6,995,011 | B2 | 2/2006 | Itoh et al. |
| 7,067,318 | B2 | 6/2006 | June et al. |

(Continued)

FOREIGN PATENT DOCUMENTS

| | | | |
|---|---|---|---|
| CN | 103038231 | A | 4/2013 |
| CN | 105473141 | A | 4/2016 |

(Continued)

OTHER PUBLICATIONS

National Center for Biotechnology Information (2025). PubChem Compound Summary for CID 60478710, 5-nitro-N-(1-phenylbenzimidazol-2-yl)furan-2-carboxamide. Retrieved Sep. 4, 2025 from https://pubchem.ncbi.nlm.nih.gov/compound/604 ("PubChem CID 60478710") (Year: 2012).*
National Center for Biotechnology Information (2025). PubChem Compound Summary for CID 110712084, N-[(1-cyclopropylbenzimidazol-2-yl)methyl]furan-2-carboxamide. Retrieved Sep. 4, 2025 from https://pubchem.ncbi.nlm.nih.gov/co ("PubChem CID 110712084") (Year: 2016).*
CAS Registry No. 1212404-62-0 (Year: 2010).*
CAS Registry No. 1644411-35-7 (Year: 2015).*
Extended European Search Report for European Application No. 20749261.2, dated Oct. 18, 2022 (8 pages).

(Continued)

*Primary Examiner* — James H Alstrum-Acevedo
*Assistant Examiner* — Chantal Adlam
(74) *Attorney, Agent, or Firm* — Clark & Elbing LLP

(57) ABSTRACT

The present disclosure features compounds useful for the treatment of BAF complex-related disorders.

14 Claims, No Drawings

(56) References Cited

U.S. PATENT DOCUMENTS

| | | | |
|---|---|---|---|
| 7,144,575 | B2 | 12/2006 | June et al. |
| 7,172,869 | B2 | 2/2007 | June et al. |
| 7,175,843 | B2 | 2/2007 | June et al. |
| 7,205,103 | B2 | 4/2007 | Emerson |
| 7,232,566 | B2 | 6/2007 | June et al. |
| 7,348,326 | B2 | 3/2008 | DeSimone et al. |
| 7,572,631 | B2 | 8/2009 | Berenson et al. |
| 8,324,367 | B2 | 12/2012 | Kaemmerer et al. |
| 8,642,660 | B2 | 2/2014 | Goldfarb |
| 8,697,359 | B1 | 4/2014 | Zhang |
| 8,703,761 | B2 | 4/2014 | Forster et al. |
| 8,771,945 | B1 | 7/2014 | Zhang |
| 8,795,965 | B2 | 8/2014 | Zhang |
| 8,865,406 | B2 | 10/2014 | Zhang et al. |
| 8,945,861 | B2 | 2/2015 | Bomgarden et al. |
| 8,946,268 | B2 | 2/2015 | Lau et al. |
| 9,072,052 | B2 | 6/2015 | Griffin et al. |
| 9,126,985 | B2 | 9/2015 | Kley et al. |
| 9,353,051 | B2 | 5/2016 | Byrd et al. |
| 9,403,843 | B2 | 8/2016 | Thatcher et al. |
| 9,410,943 | B2 | 8/2016 | Kadoch et al. |
| 9,546,206 | B2 | 1/2017 | Ring et al. |
| 9,546,296 | B2 | 1/2017 | Wang et al. |
| 9,636,323 | B2 | 5/2017 | Lin et al. |
| 9,656,959 | B2 | 5/2017 | Ni et al. |
| 9,694,084 | B2 | 7/2017 | Bradner et al. |
| 9,708,338 | B2 | 7/2017 | Yukimasa et al. |
| 9,708,348 | B2 | 7/2017 | Castro et al. |
| 9,850,543 | B2 | 12/2017 | Jagani et al. |
| 9,919,998 | B2 | 3/2018 | Ebright et al. |
| 9,932,340 | B2 | 4/2018 | Dai et al. |
| 10,105,420 | B2 | 10/2018 | Kadoch et al. |
| 10,131,637 | B2 | 11/2018 | Abdel-Meguid et al. |
| 10,207,998 | B2 | 2/2019 | Derbyshire et al. |
| 10,239,888 | B2 | 3/2019 | Bradner et al. |
| 10,266,850 | B2 | 4/2019 | Doudna et al. |
| 10,308,614 | B2 | 6/2019 | Albrecht et al. |
| 10,464,925 | B2 | 11/2019 | Bradner et al. |
| 10,472,376 | B2 | 11/2019 | Yamamoto et al. |
| 10,646,575 | B2 | 5/2020 | Phillips et al. |
| 10,660,968 | B2 | 5/2020 | Phillips et al. |
| 10,669,253 | B2 | 6/2020 | Bradner et al. |
| 10,849,982 | B2 | 12/2020 | Phillips et al. |
| 10,905,768 | B1 | 2/2021 | Phillips et al. |
| 10,976,320 | B2 | 4/2021 | Dykhuizen et al. |
| 11,149,254 | B2 | 10/2021 | Szalay et al. |
| 11,419,859 | B2 | 8/2022 | Agresta |
| 11,485,732 | B2 | 11/2022 | Vaswani et al. |
| 11,497,752 | B2 | 11/2022 | Anthony et al. |
| 11,639,345 | B2 | 5/2023 | Bloch et al. |
| 11,773,085 | B2 | 10/2023 | Zhou et al. |
| 11,793,802 | B2 | 10/2023 | Bearss et al. |
| 11,851,445 | B2 | 12/2023 | Ruppel et al. |
| 11,865,114 | B2 | 1/2024 | Ramachandra et al. |
| 12,282,014 | B2 | 4/2025 | Kadoch et al. |
| 12,383,560 | B2 | 8/2025 | Anthony et al. |
| 12,441,726 | B2 | 10/2025 | Wilson et al. |
| 2002/0037281 | A1 | 3/2002 | Davidson et al. |
| 2003/0027335 | A1 | 2/2003 | Ruley et al. |
| 2004/0216178 | A1 | 10/2004 | Jones et al. |
| 2005/0079512 | A1 | 4/2005 | Emerson et al. |
| 2005/0130919 | A1 | 6/2005 | Xu et al. |
| 2006/0058255 | A1 | 3/2006 | Chen et al. |
| 2007/0105181 | A1 | 5/2007 | Pope et al. |
| 2008/0221157 | A1 | 9/2008 | Chakravarty et al. |
| 2010/0048565 | A1* | 2/2010 | Frenkel .................. A61P 31/04 548/307.4 |
| 2010/0197621 | A1 | 8/2010 | Henry et al. |
| 2011/0003809 | A1 | 1/2011 | Ahrendt |
| 2011/0230486 | A1 | 9/2011 | Lau et al. |
| 2012/0035244 | A1 | 2/2012 | Chinnaiyan et al. |
| 2012/0308484 | A1 | 12/2012 | Szalay et al. |
| 2014/0287931 | A1 | 9/2014 | Bernards et al. |
| 2015/0057169 | A1 | 2/2015 | Siu et al. |
| 2015/0376139 | A1 | 12/2015 | Abdel-Meguid et al. |
| 2016/0032402 | A1 | 2/2016 | Jagani et al. |
| 2016/0130663 | A1 | 5/2016 | Kohno et al. |
| 2016/0200721 | A1 | 7/2016 | Yukimasa et al. |
| 2016/0347708 | A1 | 12/2016 | Ebright et al. |
| 2018/0086720 | A1 | 3/2018 | Albrecht et al. |
| 2018/0105500 | A1 | 4/2018 | Derbyshire et al. |
| 2018/0140722 | A1 | 5/2018 | Willis et al. |
| 2018/0258491 | A1 | 9/2018 | Jagani et al. |
| 2018/0328913 | A1 | 11/2018 | Kadoch et al. |
| 2020/0069669 | A1 | 3/2020 | Grassian et al. |
| 2020/0206344 | A1 | 7/2020 | Kadoch et al. |
| 2020/0261434 | A1 | 8/2020 | Choe et al. |
| 2021/0009568 | A1 | 1/2021 | Zhou et al. |
| 2021/0038611 | A1 | 2/2021 | Anthony et al. |
| 2021/0171958 | A1 | 6/2021 | Chan et al. |
| 2021/0230154 | A1 | 7/2021 | Vaswani et al. |
| 2021/0230190 | A1 | 7/2021 | Ruppel et al. |
| 2021/0251988 | A1 | 8/2021 | Zhou et al. |
| 2021/0260171 | A1 | 8/2021 | Zhou et al. |
| 2021/0388040 | A1 | 12/2021 | Kadoch et al. |
| 2022/0016083 | A1 | 1/2022 | Centore et al. |
| 2022/0079940 | A1 | 3/2022 | Centore et al. |
| 2022/0098190 | A1 | 3/2022 | Ruppel et al. |
| 2022/0119378 | A1 | 4/2022 | Anthony et al. |
| 2022/0396604 | A1 | 12/2022 | Kadoch et al. |
| 2023/0035235 | A1 | 2/2023 | Kadoch et al. |
| 2023/0079819 | A1 | 3/2023 | Vaswani et al. |
| 2023/0121497 | A1 | 4/2023 | Vaswani et al. |
| 2023/0129003 | A1 | 4/2023 | Vaswani et al. |
| 2023/0138480 | A1 | 5/2023 | Anthony et al. |
| 2023/0145003 | A1 | 5/2023 | Wilson et al. |
| 2023/0149414 | A1 | 5/2023 | Anthony et al. |
| 2024/0101550 | A1 | 3/2024 | Vaswani et al. |
| 2024/0158387 | A1 | 5/2024 | Vaswani et al. |
| 2024/0189318 | A1 | 6/2024 | Huang |
| 2025/0241931 | A1 | 7/2025 | Reilly et al. |
| 2025/0325553 | A1 | 10/2025 | Schuck et al. |
| 2025/0339441 | A1 | 11/2025 | Schuck et al. |

FOREIGN PATENT DOCUMENTS

| | | | |
|---|---|---|---|
| CN | 107531668 | A | 1/2018 |
| EA | 202192101 | A1 | 12/2021 |
| JP | 2000-095767 | A | 4/2000 |
| WO | WO-94/10300 | A1 | 5/1994 |
| WO | WO-95/30761 | A2 | 11/1995 |
| WO | WO-2000/024392 | A1 | 5/2000 |
| WO | WO-00/59888 | A1 | 10/2000 |
| WO | WO-00/59905 | A1 | 10/2000 |
| WO | WO-2005/039643 | A2 | 5/2005 |
| WO | WO-2005/112620 | A2 | 12/2005 |
| WO | WO-2006/005941 | A1 | 1/2006 |
| WO | WO-2006/051063 | A1 | 5/2006 |
| WO | WO-2006/070806 | A1 | 7/2006 |
| WO | WO-2008/022396 | A1 | 2/2008 |
| WO | WO-2008/157500 | A1 | 12/2008 |
| WO | WO-2009/086303 | A2 | 7/2009 |
| WO | WO-2009/111277 | A1 | 9/2009 |
| WO | WO-2010/007046 | A2 | 1/2010 |
| WO | WO-2011/115998 | A2 | 9/2011 |
| WO | WO-2011/132175 | A2 | 10/2011 |
| WO | WO-2012/085650 | A1 | 6/2012 |
| WO | WO-2013/116663 | A1 | 8/2013 |
| WO | WO-2013/116682 | A1 | 8/2013 |
| WO | WO-2014/150395 | A1 | 9/2014 |
| WO | WO-2015/002230 | A1 | 1/2015 |
| WO | WO-2015/005473 | A1 | 1/2015 |
| WO | WO-2015/103317 | A1 | 7/2015 |
| WO | WO-2015/120320 | A1 | 8/2015 |
| WO | WO-2015/121688 | A1 | 8/2015 |
| WO | WO-2016/054491 | A1 | 4/2016 |
| WO | WO-2016/138114 | A1 | 9/2016 |
| WO | WO-2016/160718 | A1 | 10/2016 |
| WO | WO-2016/207212 | A1 | 12/2016 |
| WO | WO-2017/024318 | A1 | 2/2017 |
| WO | WO-2017/060470 | A1 | 4/2017 |
| WO | WO-2017/087885 | A1 | 5/2017 |
| WO | WO-2017/118734 | A1 | 7/2017 |
| WO | WO-2017/158381 | A1 | 9/2017 |

(56) References Cited

FOREIGN PATENT DOCUMENTS

WO WO-2018/148443 A1 8/2018
WO WO-2018/160636 A1 9/2018
WO WO-2018/175324 A1 9/2018
WO WO-2019/038215 A1 2/2019
WO WO-2019/040098 A1 2/2019
WO WO-2019/138017 A1 7/2019
WO WO-2019/142192 A1 7/2019
WO WO-2019/152437 A1 8/2019
WO WO-2019/152440 A1 8/2019
WO WO-2019/226915 A1 11/2019
WO WO-2020/035779 A1 2/2020
WO WO-2020/081556 A2 4/2020
WO WO-2020/081588 A1 4/2020
WO WO-2020/106915 A1 5/2020
WO WO-2020/127685 A1 6/2020
WO WO-2020/160100 A1 8/2020
WO WO-2020/160180 A1 8/2020
WO WO-2021/081032 A1 4/2021
WO WO-2021/155262 A1 8/2021
WO WO-2021/155264 A1 8/2021
WO WO-2021/155316 A1 8/2021
WO WO-2021/155320 A1 8/2021
WO WO-2021/155321 A2 8/2021
WO WO-2021/183218 A1 9/2021
WO WO-2021/236080 A1 11/2021
WO WO-2022/192621 A1 9/2022
WO WO-2022/198043 A1 9/2022
WO WO-2023/009834 A2 2/2023
WO WO-2023/196560 A1 10/2023
WO WO-2023/196565 A1 10/2023
WO WO-2023/196567 A2 10/2023
WO WO-2024/024428 A1 2/2024
WO WO-2024/031875 A1 2/2024
WO WO-2024/086577 A1 4/2024
WO WO-2024/216136 A1 10/2024
WO WO-2024/216151 A1 10/2024
WO WO-2024/249769 A2 12/2024
WO WO-2025/080767 A1 4/2025
WO WO-2025/080769 A1 4/2025

OTHER PUBLICATIONS

International Search Report and Written Opinion for International Application No. PCT/US2020/015605, mailed Jun. 16, 2020 (15 pages).
International Search Report and Written Opinion for International Application No. PCT/US2020/015723, mailed Jul. 2, 2020 (15 pages).
International Search Report and Written Opinion for International Application No. PCT/US2020/033829, mailed Aug. 17, 2020 (14 pages).
International Search Report and Written Opinion for International Application No. PCT/US21/15876, mailed on Apr. 7, 2021 (23 pages).
International Search Report and Written Opinion for International Application No. PCT/US2022/019506, dated Jun. 7, 2022 (9 pages).
International Search Report and Written Opinion for International Application No. PCT/US21/15878, dated Jun. 4, 2021 (10 pages).
Kadoch et al., "Reversible Disruption of mSWI/SNF (BAF) Complexes by the SS18-SSX Oncogenic Fusion in Synovial Sarcoma," available in PMC May 16, 2013, published in final edited form as: Cell. 153(1):71-85 (2013) (26 pages).
McBride et al., "Disruption of mammalian SWI/SNF and polycomb complexes in human sarcomas: mechanisms and therapeutic opportunities," J Pathol. 244(5): 638-649 (2018).
Papillon et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers," J Med Chem. 61(22):10155-72 (2018).
PubChem CID 117640569, "N-[2-[[4-(4-Methoxyphenyl)-1,3-thiazol-2-yl]amino]-2-oxoethyl]-1,3-thiazole-5-carboxamide," https://pubchem.ncbi.nlm.nih.gov/compound/117640569, created Feb. 23, 2016 (9 pages).
PubChem CID 56442706, "1-(4-Methoxyphenyl)-N-[2-oxo-2-[4-(1,2,4-triazol-1-yl) anilino]ethyl]pyrazole-3-carboxamide," https://pubchem.ncbi.nlm.nih.gov/compound/56442706, created Jan. 25, 2012 (8 pages).
PubChem CID 91946137, "N-[2-[(1-Ethylpyrazol-3-yl}amino]-2-oxoethyl]-1-methylpyrazole-3-carboxamide," https://pubchem.ncbi.nlm.nih.gov/compound/91946137, created Oct. 22, 2015 (8 pages).
PubChem Compound Summary for CID 155037309, dated Dec. 19, 2020 (9 pages).
PubChem Compound Summary for CID No. 136572628, "4-Chloro-N-[2-(cyclopentylamino)-2-oxoethyl]-5-nitro-1H-pyrazole-3-carboxamide," created Jan. 24, 2019, <https://pubchem.ncbi.nlm.nih.gov/compound/136572628>, (7 pages).
PubChem Compound Summary for CID No. 49726797, "N-Methyl-N-(2-oxo-2-((4-(pyridin-3-yl)thiazol-2-yl)amino)ethyl)-1H-indole-3-carboxamide," created Nov. 27, 2010, <https://pubchem.ncbi.nlm.nih.gov/compound/49726797>, (8 pages).
PubChem Compound Summary for CID No. 91945707, "N-[2-[(4,5-Dimethyl-1,3-thiazol-2-yl) amino]-2-oxoethyl]-1-methylpyrazole-3-carboxamide," created Oct. 22, 2015 <https://pubchem.ncbi.nlm.nih.gov/compound/91945707>, (8 pages).
PubChem Compound Summary for PubChem CID 49726798, "N-(2-((4-(Furan-2-yl)thiazol-2-yl)amino)-2-oxoethyl)-N-methyl-1H-indole-3-carboxamide," created Nov. 27, 2010 <https://pubchem.ncbi.nih.gov/compound/49726798> (8 pages).
PubChem Compound Summary for SID 172131678, dated Dec. 9, 2014 (8 pages).
Tikdari et al., "Reaction of 2-Aminothiazoles with 5-Oxazolones," ChemInform. 18(47):Abstract 199 (1987) (1 page).
Zvarec et al., "5-Benzylidenerhodanine and 5-benzylidene-2-4-thiazolidinedione based antibacterials," Bioorg Med Chem Lett. 22(8):2720-2 (2012).
U.S. Appl. No. 63/707,938, Adam et al.
"Compound Summary: N-[(S)-1-[[4-[6-[(2R,6S)-2,6-Dimethylmorpholino]-2-pyridyl]-2-thiazolyl]amino]-3-methoxy-1-oxo-2-propyl]-1-(methylsulfonyl)-1H-pyrrole-3-carboxamide," PubChem. CID: 156818027, <https://pubchem.ncbi.nlm.nih.gov/compound/156818027>, created Nov. 10, 2021, accessed Jan. 19, 2025 (9 pages).
"FLI1 gene," MedlinePlus, published May 1, 2012, <https://medlineplus.gov/genetics/> (3 pages).
"Form S-1 Registration Statement: Foghorn Therapeutics Inc.," as filed with the United States Securities and Exchange Commission on Oct. 2, 2020 (230 pages).
Adamo et al., "The oncogene ERG: a key factor in prostate cancer," Oncogene 35(4):403-14 (Jan. 28, 2016).
Advani et al., "A Phase 1 study of imatinib mesylate in combination with cytarabine and daunorubicin for c-kit positive relapsed acute myeloid leukemia," Leuk Res. 34(12):1622-6 (Dec. 2010).
Alazawi, "Foghorn Therapeutics," Blackseed Bio, last updated Mar. 4, 2022, retrieved Jul. 24, 2023, from <https://blackseedbio.com/reports/fhtx#pipeline> (26 pages).
Anders et al., "HTSeq—a Python framework to work with high-throughput sequencing data," Bioinformatics 31(2):166-9 (Jan. 15, 2015).
Asangani et al., "Therapeutic targeting of BET bromodomain proteins in castration-resistant prostate cancer," available in PMC Dec. 12, 2014. Published in final edited form as: Nature. 510(7504):278-82 (2014) (44 pages).
Attard et al., "Duplication of the fusion of TMPRSS2 to ERG sequences identifies fatal human prostate cancer," available in PMC Feb. 24, 2009. Published in final edited form as: Oncogene. 27(3):253-63 (2008) (19 pages).
Basuyaux et al., "The Ets transcription factors interact with each other and with the c-Fos/c-Jun complex via distinct protein domains in a DNA-dependent and -independent manner," J Biol Chem. 272(42):26188-95 (1997).
Bendall et al., "Prevention of amino acid conversion in SILAC experiments with embryonic stem cells," Mol Cell Proteomics. 7(9):1587-97 (2008).
Berger et al., "Androgen-induced differentiation and tumorigenicity of human prostate epithelial cells," Cancer Res. 64(24):8867-75 (2004).

(56) References Cited

OTHER PUBLICATIONS

Börno et al., "Genome-wide DNA methylation events in TMPRSS2-ERG fusion-negative prostate cancers implicate an EZH2-dependent mechanism with miR-26a hypermethylation," Cancer Discov. 2(11):1024-35 (2012).
Boulay et al., "Cancer-Specific Retargeting of BAF Complexes by a Prion-like Domain," Cell 171(1):163-78 (Sep. 21, 2017) (36 pages).
Caira, Mino R. "Crystalline polymorphism of organic compounds. "Design of Organic Solids (1998): 163-208.
Camuzeaux et al., "Imaging Erg and Jun transcription factor interaction in living cells using fluorescence resonance energy transfer analyses," Biochem Biophys Res Commun. 332(4):1107-14 (2005).
Cancer Genome Atlas Research Network, "The Molecular Taxonomy of Primary Prostate Cancer," Cell. 163(4):1011-25 (2015) (16 pages).
Carell et al., "A novel procedure for the synthesis of libraries containing small organic molecules," Angew Chem Int Ed Engl. 33(20):2059-2061 (1994).
Carell et al., "A Solution-Phase Screening Procedure for the Isolation of Active Compounds from a Library of Molecules," Angewandte Chemie International Edition in English. 33(20): 2061-2064 (1994).
CAS RN: 1223164-86-0; STN entry date: May 14, 2010; N-[2-[[4-(3-Fluoro-4-methoxyphenyl)-2-thiazolyl]amino]-2-oxoethyl]-2-methyl-3-furancarboxamide (1page).
CAS RN: 1300403-14-8; STN entry date May 25, 2011; 5-Methyl-N-[2-oxo-2-[ (5-phenyl-2-pyridinyl)amino]ethyl]-2-thiophenecarboxamide (1 page).
CAS RN: 924410-17-3; STN entry date: Mar. 2, 2007; 5-Methyl-N-[2-oxo-2-[ (4-phenyl-2-thiazolyl)amino]ethyl]-2-thiophenecarboxamide (1 page).
CAS RN: 924420-04-2; STN entry date: Mar. 2, 2007; 5-Methyl-N-[2-oxo-2-[[4-(4-pyridinyl)-2-thiazolyl]amino]ethyl]-2-thiophenecarboxamide (1 page).
Centore et al., "Abstract 1224: Discovery of novel BAF inhibitors for the treatment of transcription factor-driven cancers," Poster Presentations—Proffered abstracts, Cancer Research 81(13_ Supplement):1224 (Jul. 1, 2021) (2 pages).
Chandler et al., "ARID1a-DNA interactions are required for promoter occupancy by SWI/SNF," Mol Cell Biol. 33(2):265-80 (Jan. 2013).
Chattopahdyay et al., "Uveal melanoma: From diagnosis to treatment and the science in between," Cancer. 122(15):2299-2312 (26 pages) (Aug. 2016).
Chen et al., "ETS factors reprogram the androgen receptor cistrome and prime prostate tumorigenesis in response to PTEN loss," available in PMC Feb. 1, 2014. Published in final edited form as: Nat Med. 19(8):1023-9 (2013) (21 pages).
Chng et al., "A transcriptional repressor co-regulatory network governing androgen response in prostate cancers," EMBO J. 31(12):2810-23 (2012).
Cho et al., "An unnatural biopolymer," Science. 261(5126):1303-1305 (1993).
Coban et al., "Synthesis, biological activity screening and molecular modeling study of acylaminoacetamide derivatives," Med Chem Res. 24(10):3710-29 (Jul. 25, 2015).
Collins et al., "Abstract 2122: The dual BRM/BRG1 (SMARCA2/4) inhibitor FHD-286 induces differentiation in preclinical models of AML," Cancer Res. 83(7_Supplement) (Apr. 2023) (5 pages).
Cull et al., "Screening for receptor ligands using large libraries of peptides linked to the C terminus of the lac repressor," Proc Natl Acad Sci. 89(5):1865-1869. (1992).
Cwirla et al., "Peptides on phage: A vast library of peptides for identifying ligands," Proc Nati Acad Sci. 87:6378-6382 (1990).
Danziger et al., Automated site-directed drug design: a general algorithm for knowledge acquisition about hydrogen-bonding regions at protein surfaces, Proc R Soc Lond B Biol Sci. 236(1283): 101-113 (Mar. 1989) (14 pages).
Database Registry, RN 1004932-80-2, entered Feb. 21, 2008 (1 page).
Database Registry, RN 1175782-23-6, entered Aug. 26, 2009 (1 page).
Database Registry, RN 1315743-98-6, entered Aug. 11, 2011 (1 page).
Database Registry, RN 1323331-37-8, entered Aug. 25, 2011 (1 page).
Database Registry, RN 1323542-96-6, entered Aug. 26, 2011 (1 page).
Database Registry, RN 1324163-01-0, entered Aug. 28, 2011 (1 page).
Database Registry, RN 1327304-26-6, entered Sep. 2, 2011 (1 page).
Database Registry, RN 878254-76-3, entered Mar. 28, 2006 (1 page).
Décor et al., "Design, synthesis and biological evaluation of novel aminothiazoles as antiviral compounds acting against human rhinovirus," Bioorg Med Chem Lett. 23(13):3841-7 (Jul. 1, 2013).
Delattre et al., "Gene fusion with an ETS DNA-binding domain caused by chromosome translocation in human tumours," Nature. 359(6391):162-5 (1992).
Devlin et al., "Random Peptide Libraries: a Source of Specific Protein Binding Molecules," Science. 249(4967):404-406 (1990).
DeWitt et al., "'Diversomers': an approach to nonpeptide, nonoligomeric chemical diversity," Proc Natl Acad Sci. 90(15):6909-6913 (1993).
Dobin et al., "STAR: ultrafast universal RNA-seq aligner," Bioinformatics. 29(1):15-21 (2013).
Dominguez et al. "Beyond editing: Repurposing CRISPR-Cas9 for Precision Genome Regulation and Interrogation," available in PMC Jun. 27, 2016, published in final edited form as: Nat Rev Mol Cell Biol. 17(1):5-15 (Jan. 2016) (24 pages).
Donaldson et al., "Solution structure of the ETS domain from murine Ets-1: a winged helix-turn-helix DNA binding motif," EMBO J. 15(1):125-34 (1996).
Erb et al., "Recursive deconvolution of combinatorial chemical libraries," Proc Natl Acad Sci. 91(24):11422-11426 (1994).
Fadul et al., "EWS/FLI utilizes NKX2-2 to repress mesenchymal features of Ewing sarcoma," Genes Cancer 6(3-4):129-43 (Mar. 2015).
Fathi et al., "Differentiation syndrome with lower-intensity treatments for acute myeloid leukemia," Am J Hematol. 96(6):735-46 (Jun. 1, 2021) (13 Pages).
Felici et al., "Selection of antibody ligands from a large library of oligopeptides expressed on a multivalent exposition vector," J Mol Biol. 222(2):301-10 (1991).
Feng et al., "GFOLD: a generalized fold change for ranking differentially expressed genes from RNA-seq data," Bioinformatics. 28(21):2782-8 (2012).
Fiskus et al., "Pre-Clinical Efficacy of Targeting Baf Complexes through Inhibition of the Dual Atpases BRG1 and BRM by FHD-286 in Cellular Models of AML of Diverse Genetic Background," Blood. 140(Supplement 1):8819-20 (Nov. 2022) (15 pages).
Fodor et al., "Multiplexed biochemical assays with biological chips," Nature. 364:555-556 (1993).
Gaj et al. "ZFN, TALEN and CRISPR/Cas-based Methods for Genome Engineering," available in PMC Jul. 1, 2014, published in final edited form as: Trends Biotechnol. 31(7):397-405 (Jul. 2013) (20 pages).
Gallop et al., "Applications of Combinatorial Technologies to Drug Discovery. 1. Background and Peptide Combinatorial Libraries," J Med Chem 37(9):1233-51 (1994).
Gene Ontology Consortium, "Gene Ontology Consortium: going forward," Nucleic Acids Res. 43(Database issue):D1049-56 (2015).
Gingras et al., "Advances in protein complex analysis using mass spectrometry," J Physiol. 563(Pt 1):11-21 (Feb. 15, 2005).
Godwin et al., "Gemtuzumab ozogamicin in acute myeloid leukemia," Leukemia 31(9):1855-68 (Sep. 2017).
Grohar et al., "Ecteinascidin 743 interferes with the activity of EWS-FLI1 in Ewing sarcoma cells," Neoplasia 13(2):145-53 (Feb. 2011).
Helgeson et al., "Characterization of TMPRSS2:ETV5 and SLC45A3:ETV5 gene fusions in prostate cancer," Cancer Res. 68(1):73-80 (2008).

(56) References Cited

OTHER PUBLICATIONS

Hentemann, "Abstract ND14: Pharmacological profile and anti-tumor properties of FHD-286: A novel BAF inhibitor for the treatment of transcription factor-driven cancers," Cancer Res. 82(12_Supplement): ND14 (Jun. 2022) (4 pages).
Herrero-Martin et al., "Stable interference of EWS-FLI1 in an Ewing sarcoma cell line impairs IGF-1/IGF-1R signalling and reveals TOPK as a new target," Br J Cancer 101(1):80-90 (Jul. 7, 2009).
Ho et al., "An embryonic stem cell chromatin remodeling complex, esBAF, is essential for embryonic stem cell self-renewal and pluripotency," Proc Natl Acad Sci U S A. 106(13):5181-6 (2009).
Hohmann et al., "Sensitivity and engineered resistance of myeloid leukemia cells to BRD9 inhibition," Nat Chem Biol. 12(9): 672-679 (Sep. 2016) (12 pages).
Houghten et al., "The use of synthetic peptide combinatorial libraries for the identification of bioactive peptides," Biotechniques. 13(3):412-21 (1992).
Ichikawa et al., "An RNA-binding protein gene, TLS/FUS, is fused to ERG in human myeloid leukemia with t(16;21) chromosomal translocation," Cancer Res. 54(11):2865-8 (1994).
Jones et al., "A novel series of potent and selective ketone histone deacetylase inhibitors with antitumor activity in vivo," J Med Chem. 51(8):2350-3 (Apr. 24, 2008).
Karim et al., "The ETS-domain: a new DNA-binding motif that recognizes a purine-rich core DNA sequence," Genes Dev. 4(9):1451-3 (1990).
Kedage et al., "An Interaction with Ewing's Sarcoma Breakpoint Protein EWS Defines a Specific Oncogenic Mechanism of ETS Factors Rearranged in Prostate Cancer," Cell Rep. 17(5):1289-301 (Oct. 25, 2016) (14 pages).
Klezovitch et al., "A causal role for ERG in neoplastic transformation of prostate epithelium," Proc Natl Acad Sci U S A. 105(6):2105-10 (2008).
Kumar et al., "Diazanaphthalen-3-yl carboxamides as inhibitors of proteins of the Wnt pathway and their preparation," Database Caplus. (Jan. 2019) (12 pages).
Kumar-Sinha et al., "Recurrent gene fusions in prostate cancer," available in PMC Jul. 16, 2009. Published in final edited form as: Nat Rev Cancer. 8(7):497-511 (2008) (29 pages).
Kunderfranco et al., "ETS transcription factors control transcription of EZH2 and epigenetic silencing of the tumor suppressor gene Nkx3.1 in prostate cancer," PLoS One. 5(5):e10547 (2010) (17 pages).
Lam et al., "A new type of synthetic peptide library for identifying ligand-binding activity," Nature. 354(6348):82-84 (1991).
Lam, "Application of combinatorial library methods in cancer research and drug discovery," Anticancer Drug Des. 12(3):145-67 (1997).
Langmead et al., "Fast gapped-read alignment with Bowtie 2," available in PMC Apr. 1, 2013. Published in final edited form as: Nat Methods. 9(4):357-9 (2012) (8 pages).
Link et al., "Targeting the BAF57 Swi/Snf subunit in prostate cancer: a novel platform to control androgen receptor activity," Cancer Res. 68(12):4551-8 (2008).
Love et al., "Moderated estimation of fold change and dispersion for RNA-seq data with DESeq2," Genome Biol. 15(12):550 (2014) (21 pages).
Lupien et al., "FoxA1 translates epigenetic signatures into enhancer-driven lineage-specific transcription," Cell. 132(6):958-70 (2008).
Machanick et al., "MEME-ChIP: motif analysis of large DNA datasets," Bioinformatics. 27(12):1696-7 (2011).
Mackereth et al., "Diversity in structure and function of the Ets family PNT domains," J Mol Biol. 342(4):1249-64 (2004).
Madura et al., "N-recognin/Ubc2 interactions in the N-end rule pathway," J Biol Chem. 268(16):12046-54 (1993).
McBride et al., "Disruption of mammalian SWI/SNF and polycomb complexes in human sarcomas: mechanisms and therapeutic opportunities," J Pathol. 244(5): 638-649 (Apr. 2018).
Melé et al., "The human transcriptome across tissues and individuals," available in PMC Aug. 24, 2015. Published in final edited form as: Science. 348(6235):660-5 (2015) (12 pages).
Michel et al., "Abstract PR15: BRD9 defines a novel mammalian SWI/SNF (BAF) complex configuration which supports proliferation in AML," Clin Cancer Res. 23(24_Suppl) Abstract PR15 (2017) (4 pages).
Mill et al., "RUNX1-targeted therapy for AML expressing somatic or germline mutation in RUNX1," Blood 134(1):59-73 (Jul. 4, 2019).
Mounir et al., "ERG signaling in prostate cancer is driven through PRMT5-dependent methylation of the Androgen Receptor," Elife. 5:e13964 (2016) (19 pages).
Nagaich et al., "Rapid periodic binding and displacement of the glucocorticoid receptor during chromatin remodeling," Mol Cell. 14(2):163-74 (2004).
Nam et al., "Expression of the TMPRSS2:ERG fusion gene predicts cancer recurrence after surgery for localised prostate cancer," Br J Cancer. 97(12):1690-5 (2007).
Ong et al., "A practical recipe for stable isotope labeling by amino acids in cell culture (SILAC)," Nat Protoc. 1(6):2650-60 (2006).
Papillon et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers," J Med Chem. 61(22):10155-72 (Nov. 2018).
Paulo et al., "FLII is a novel ETS transcription factor involved in gene fusions in prostate cancer," Genes Chromosomes Cancer. 51(3):240-9 (2012).
Pescatore et al., "Optimization of a series of potent and selective ketone histone deacetylase inhibitors," Bioorg Med Chem Lett. 18(20):5528-32 (Oct. 15, 2008).
Petrovics et al., "Frequent overexpression of ETS-related gene-1 (ERG1) in prostate cancer transcriptome," Oncogene. 24(23):3847-52 (2005).
Pomerantz et al., "The androgen receptor cistrome is extensively reprogrammed in human prostate tumorigenesis," available in PMC May 1, 2016. Published in final edited form as: Nat Genet. 47(11):1346-51 (2015) (17 pages).
Prensner et al., "The long noncoding RNA SChLAP1 promotes aggressive prostate cancer and antagonizes the SWI/SNF complex," available in PMC May 1, 2014. Published in final edited form as: Nat Genet. 45(11):1392-8 (2013) (26 pages).
PubChem, "Compound Summary for CID 108452511," <https://pubchem.ncbi.nlm.nih.gov/compound/108452511>, created Jan. 15, 2016, retrieved Jan. 4, 2021 (7 pages).
PubChem, "Compound Summary for CID 2955118," <https://pubchem.ncbi.nlm.nih.gov/compound/2955118>, created Jul. 29, 2005, retrieved Mar. 22, 2017 (13 pages).
PubChem, "Compound Summary for CID 7325930," <https://pubchem.ncbi.nlm.nih.gov/compound/7325930>, created Jul. 29, 2006, retrieved Mar. 22, 2017 (11 pages).
PubChem, "Compound Summary for CID 970466," <https://pubchem.ncbi.nlm.nih.gov/compound/970466>, created Jul. 9, 2005, retrieved Mar. 22, 2017 (11 pages).
Quinlan et al., "BEDTools: a flexible suite of utilities for comparing genomic features," Bioinformatics. 26(6):841-2 (2010).
Rago et al., "Exquisite Sensitivity to Dual BRG1/BRM ATPase Inhibitors Reveals Broad SWI/SNF Dependencies in Acute Myeloid Leukemia," Mol Cancer Res. 20(3):361-72 (Mar. 1, 2022).
Rajput et al., "Frequency of the TMPRSS2:ERG gene fusion is increased in moderate to poorly differentiated prostate cancers," J Clin Pathol. 60(11):1238-43 (2007).
Ramos et al., "Current Approaches in the Treatment of Relapsed and Refractory Acute Myeloid Leukemia," J Clin Med. 4(4):665-95 (Apr. 2015).
Rappsilber et al., Protocol for micro-purification, enrichment, pre-fractionation and storage of peptides for proteomics using StageTips, Nat Protoc. 2(8):1896-906 (2007).
Riggi et al., "EWS-FLI1 utilizes divergent chromatin remodeling mechanisms to directly activate or repress enhancer elements in Ewing sarcoma," Cancer Cell 26(5):668-81 (Nov. 10, 2014) (28 pages).

(56) References Cited

OTHER PUBLICATIONS

Sankar et al., "Promiscuous partnerships in Ewing's sarcoma," Cancer Genet. 204(7):351-65 (Jul. 2011) (28 pages).
Schiefer et al., "Design, synthesis, and optimization of novel epoxide incorporating peptidomimetics as selective calpain inhibitors," J Med Chem. 56(15):6054-68 (Feb. 7, 2013).
Scott et al., "Searching for peptide ligands with an epitope library," Science. 249(4967):386-390 (1990).
Selleck Chemicals, "Safety Data Sheet: FHD-286," <https://www.selleckchem.com/msds/MSDS_E1178.pdf>, revised May 1, 2014 (2 pages).
Shen et al., "The SWI/SNF ATPase Brm is a gatekeeper of proliferative control in prostate cancer," Cancer Res. 68(24):10154-62 (Dec. 2008).
Shi et al., "Role of SWI/SNF in acute leukemia maintenance and enhancer-mediated Myc regulation," Genes Dev. 27(24):2648-62 (Dec. 2013).
Siegel et al., "Cancer statistics, 2015," CA Cancer J Clin. 65(1):5-29 (2015).
Simone, Part XIV: Oncology: Introduction, Textbook of Medicine, Bennett et al., 20(1), 1004-1010 (1997).
Spickler et al., "Phosphatidylinositol 4-kinase III beta is essential for replication of human rhinovirus and its inhibition causes a lethal phenotype in vivo," Antimicrob Agents Chemother. 57(7):3358-68 (Jul. 2013).
STN Registry Database, CAS RN 858073-83-3, Albany Molecular Research, Inc., entered Aug. 3, 2005 (1 page).
STN Registry Database, RN 1010893-05-6, entered Mar. 30, 2008 (2 pages).
STN Registry Database, RN 1049271-26-2, entered Sep. 14, 2008 (2 pages).
STN Registry Database, RN 1081662-32-9, entered Dec. 8, 2008 (2 pages).
STN Registry Database, RN 1209112-42-4, entered Mar. 12, 2010 (2 pages).
STN Registry Database, RN 1246047-75-5, entered Oct. 12, 2010 (2 pages).
STN Registry Database, RN 1308280-67-2, entered Jun. 9, 2011 (2 pages).
STN Registry Database, RN 1351682-19-3, entered Dec. 22, 2011 (2 pages).
STN Registry Database, RN 1401558-47-1, entered Oct. 22, 2012 (2 pages).
STN Registry Database, RN 1455783-72-8, entered Oct. 6, 2013 (2 pages).
STN Registry Database, RN 1576383-94-2, entered Mar. 31, 2014 (2 pages).
STN Registry Database, RN 1586193-45-4, entered Apr. 17, 2014 (2 pages).
STN Registry Database, RN 1827759-12-5, entered Dec. 13, 2015 (2 pages).
STN Registry Database, RN 1831899-24-1, entered Dec. 17, 2015 (2 pages).
STN Registry Database, RN 1839545-15-1, entered Dec. 31, 2015 (2 pages).
STN Registry Database, RN 923768-18-7, entered Feb. 28, 2007 (2 pages).
STN Registry Database, RN 923809-79-4, entered Feb. 28, 2007 (2 pages).
STN Registry Database, RN 931893-54-8, entered Apr. 23, 2007 (2 pages).
STN Registry Database, RN 932130-00-2, entered Apr. 24, 2007 (2 pages).
STN Registry Database, RN 938283-11-5, entered Jun. 22, 2007 (2 pages).
Subramanian et al., "Gene set enrichment analysis: a knowledge-based approach for interpreting genome-wide expression profiles," Proc Natl Acad Sci USA. 102(43):15545-50 (2005).
Sun et al., "TMPRSS2-ERG fusion, a common genomic alteration in prostate cancer activates C-MYC and abrogates prostate epithelial differentiation," available in PMC Oct. 14, 2020. Published in final edited form as: Oncogene. 27(40)5348-53 (2008) (12 pages).
Takigami et al., "Synthetic siRNA targeting the breakpoint of EWS/Fli-1 inhibits growth of Ewing sarcoma xenografts in a mouse model," Int J Cancer 128(1):216-26 (Jan. 1, 2011).
Tikdari et al., "Reaction of 2-Aminothiazoles with 5-Oxazolones," Indian Journal of Chemistry 26B:478-9 (May 1987).
Tomlins et al., "Recurrent fusion of TMPRSS2 and ETS transcription factor genes in prostate cancer," Science.310(5748):644-8 (2005).
Tomlins et al., "Role of the TMPRSS2-ERG gene fusion in prostate cancer," Neoplasia. 10(2):177-88 (2008) (21 pages).
Tomlins et al., "TMPRSS2: ETV4 gene fusions define a third molecular subtype of prostate cancer," Cancer Res. 66(7):3396-400 (2006).
Triandafillidi et al., "tert-Butyl ester or benzylamide of the dipeptide Pro-Gly as organocatalysts for the asymmetric aldol reaction," Tetrahedron 71:932-40 (2015).
Tsai et al. "Dimeric CRISPR RNA-guided FokI Nucleases for Highly Specific Genome Editing," available in PMC Dec. 1, 2014, published in final edited form as: Nat Biotechnol. 32(6):569-576 (Jun. 2014) (22 pages).
Tuoc et al., "Chromatin regulation by BAF170 controls cerebral cortical size and thickness," Dev Cell. 25(3):256-69 (May 2013).
Vachtenheim et al., "SWI/SNF chromatin remodeling complex is critical for the expression of microphthalmia-associated transcription factor in melanoma cells," Biochemical and Biophysical Research Communications. 392(3):454-459 (2010).
Varambally et al., "The polycomb group protein EZH2 is involved in progression of prostate cancer," Nature. 419(6907):624-9 (2002).
Vela et al., "Discovery of Enhancers of the Secretion of Leukemia Inhibitory Factor for the Treatment of Multiple Sclerosis," J Biomol Screen. 21(5):437-45 (Jun. 2016).
Verger et al., "Identification of amino acid residues in the ETS transcription factor Erg that mediate Erg-Jun/Fos-DNA ternary complex formation," J Biol Chem. 276(20):17181-9 (2001).
Wahedy et al., "Facile Synthesis and In-Vitro Antimicrobial Activity of Some Novel 2-Hetroamido-5-Amino Benzimidazoles," Am J PharmTech Res. 3(2):868-82 (2013).
Wollenick et al., "Synthetic transactivation screening reveals ETV4 as broad coactivator of hypoxia-inducible factor signaling," Nucleic Acids Res. 40(5):1928-43 (2012).
Wu et al., "Targeting the chromatin remodeling enzyme BRG1 increases the efficacy of chemotherapy drugs in breast cancer cells," Oncotarget 7(19):27158-75 (May 10, 2016).
Yang et al., "EZH2, an epigenetic driver of prostate cancer," Protein Cell. 4(5):331-41 (2013).
Yildirim et al., "Mbd3/NURD complex regulates expression of 5-hydroxymethylcytosine marked genes in embryonic stem cells," Cell. 147(7):1498-510 (2011).
Yu et al., "An integrated network of androgen receptor, polycomb, and TMPRSS2-ERG gene fusions in prostate cancer progression," Cancer Cell. 17(5):443-54 (2010).
Yu et al., "Direct recruitment of polycomb repressive complex 1 to chromatin by core binding transcription factors," Mol Cell. 45(3):330-43 (2012).
Zervos et al., "Mxi1, a protein that specifically interacts with Max to bind Myc-Max recognition sites," Cell. 72(2):223-32 (1993).
Zhang et al., "Discovery of novel dual-action antidiabetic agents that inhibit glycogen phosphorylase and activate glucokinase," Eur J Med Chem. 58:624-39 (Dec. 2012).
Zhang et al., "Model-based analysis of ChIP-Seq (MACS)," Genome Biol. 9(9):R137 (2008) (9 pages).
Zong et al., "ETS family transcription factors collaborate with alternative signaling pathways to induce carcinoma from adult murine prostate cells," Proc Natl Acad Sci U S A. 106(30):12465-70 (Jul. 2009).
Zuckermann et al., "Discovery of Nanomolar Ligands for 7-Transmembrane G-Protein-Coupled Receptors from a Diverse N-(Substituted)glycine Peptoid Library," J Med Chem. 37(17):2678-2685 (1994).
U.S. Appl. No. 19/121,614, Wan et al.
U.S. Appl. No. 19/474,359, Adam et al.

(56) References Cited

OTHER PUBLICATIONS

Adam et al., International Application No. PCT/US25/51009, filed by Foghorn Therapeutics Inc. (65 pages).
CAS, "FHD-286 CAS registration information," dated Feb. 19, 2025 (6 pages).

* cited by examiner

COMPOUNDS AND USES THEREOF

BACKGROUND

The invention relates to compounds useful for modulating BRG1- or BRM-associated factors (BAF) complexes. In particular, the invention relates to compounds useful for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY

The present invention features compounds useful for modulating a BAF complex. In some embodiments, the compounds are useful for the treatment of disorders associated with an alteration in a BAF complex, e.g., a disorder associated with an alteration in one or both of the BRG1 and BRM proteins. The compounds of the invention, alone or in combination with other pharmaceutically active agents, can be used for treating such disorders.

In an aspect, the invention features a compound having the structure:

Formula I

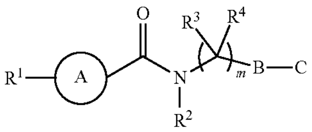

wherein $R^1$ is H, optionally substituted $C_1$-$C_6$ acyl, optionally substituted $C_1$-$C_6$ alkyl, optionally substituted $C_1$-$C_6$ heteroalkyl, optionally substituted $C_3$-$C_8$ cycloalkyl, optionally substituted $C_2$-$C_9$ heterocyclyl, optionally substituted amino, or —$SO_2R^5$;

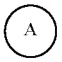

is optionally substituted arylene, optionally substituted 5-membered heteroarylene, or optionally substituted 6-membered heteroarylene;

m is 0, 1, 2, or 3;

B is an optionally substituted 6- to 10-membered bicyclic heteroarylene;

C is optionally substituted 3- to 10-membered cycloalkyl; optionally substituted 6- to 10-membered aryl; optionally substituted 5- to 10-membered heteroaryl; or optionally substituted 5- to 10-membered heterocyclyl;

$R^2$ is hydrogen or optionally substituted $C_1$-$C_6$ alkyl;

each of $R^3$ and $R^4$ is, independently, hydrogen, optionally substituted $C_1$-$C_6$ alkyl, or optionally substituted $C_1$-$C_6$ heteroalkyl;

$R^5$ is optionally substituted $C_1$-$C_6$ alkyl or —$NR^6R^7$; and each of $R^6$ and $R^7$ is, independently, optionally substituted $C_1$-$C_6$ alkyl, or a pharmaceutically acceptable salt thereof.

In some embodiments, B is a 9- or 10-membered heteroarylene

In some embodiments,

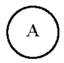

is optionally substituted 6-membered heteroarylene.

In some embodiments,

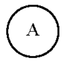

is optionally substituted 5-membered heteroarylene.

In some embodiments,

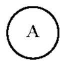

is

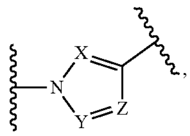

wherein each X, Y, and Z is, independently, N or $CR^8$, wherein each $R^8$ is H, halo, or $C_1$-$C_6$ alkyl (e.g., each of X, Y, and Z is CH; X is N, and each of Y and Z is CH; or X is CH, Y is $C(CH_3)$, and Z is CH); or both $R^8$, together with the carbon atoms to which they are attached, form a 5- or 6-membered ring. In some embodiments, X is N and each of Y and Z is CH. In some embodiments, Z is N and each of X and Y is CH. In some embodiments, Y is N and each of X and Z is CH.

In some embodiments,

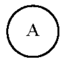

is arylene.

In some embodiments, $R^2$ is hydrogen.

In some embodiments, m is 1.

In some embodiments, $R^4$ is hydrogen.

In some embodiments, $R^3$ is hydrogen.

In some embodiments, $R^3$ is optionally substituted $C_1$-$C_6$ alkyl (e.g., methyl).

In some embodiments, $R^3$ is optionally substituted $C_1$-$C_6$ heteroalkyl (e.g., is $—CH_2OCH_3$ or $—(CH_2)_2SCH_3$).

In some embodiments, B is optionally substituted 9-membered bicyclic heteroarylene.

In some embodiments, B has the structure:

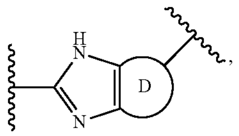

wherein D is an optionally substituted 5- or 6-membered heteroaryl or optionally substituted 5- or 6-membered heterocyclyl. In some embodiments, B is

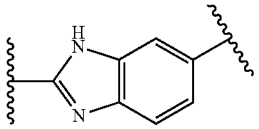 or 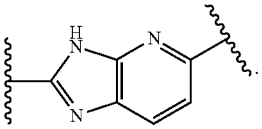

In some embodiments, B has the structure:

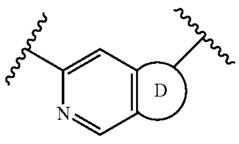

wherein D is an optionally substituted 5- or 6-membered heteroaryl or optionally substituted 5- or 6-membered heterocyclyl. In some embodiments, B is

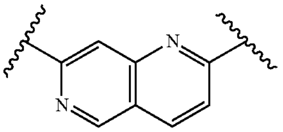 or

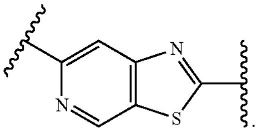

In some embodiments, C is optionally substituted $C_3$-$C_{10}$ cycloalkyl (e.g., cyclopropyl).

In some embodiments, C is optionally substituted $C_6$-$C_{10}$ aryl. In some embodiments, C is optionally substituted phenyl (e.g., 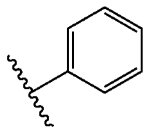, 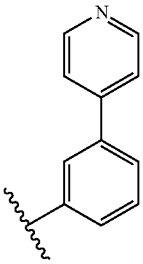,

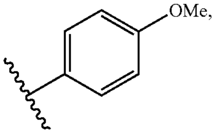, 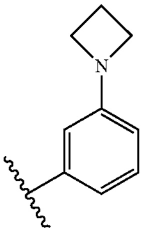,

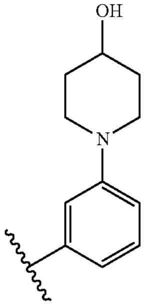, 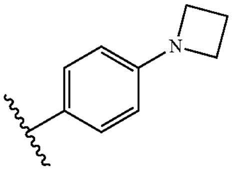,

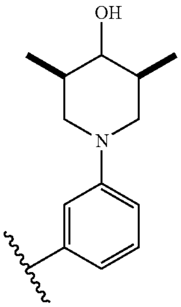,

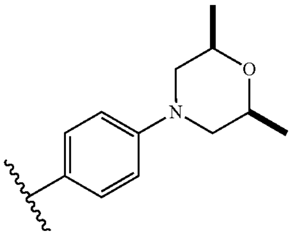,

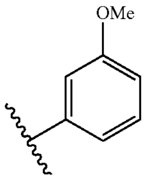, 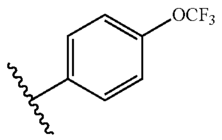,

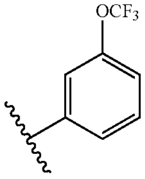, 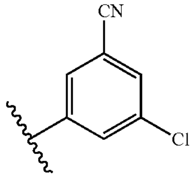,

-continued
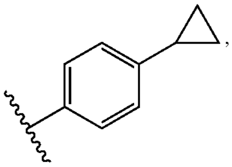,
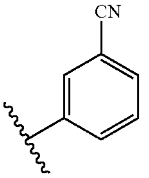,
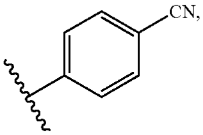,
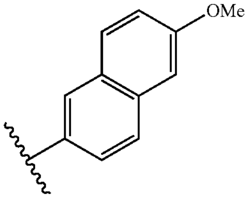,
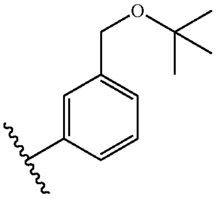,
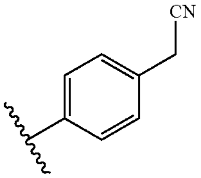,
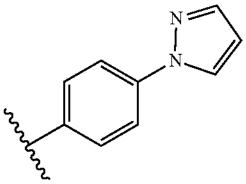,
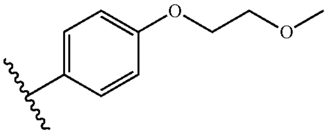,
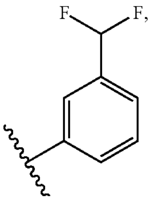,
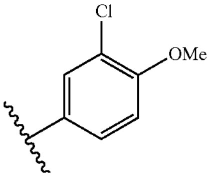,
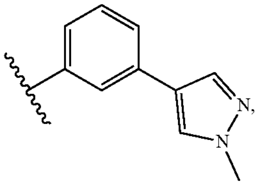 or
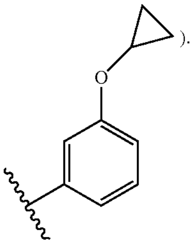).
In some embodiments, C is optionally substituted 5- to 10-membered heteroaryl (e.g.,
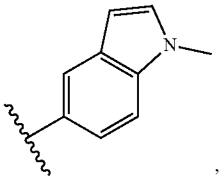,
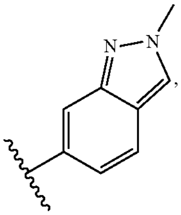,
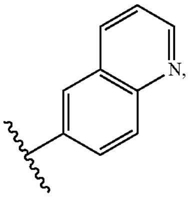,
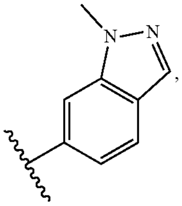,
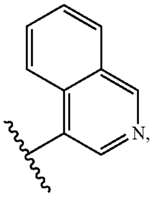,
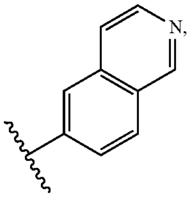,
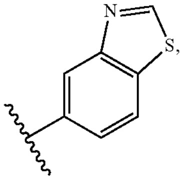,
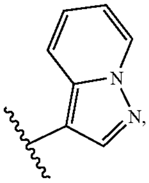,
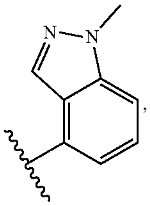,
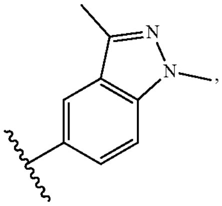,
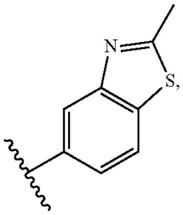,
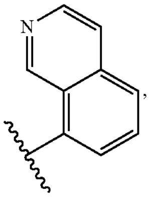,
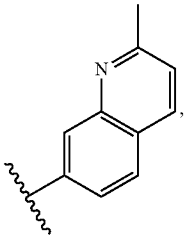,
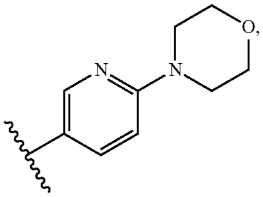

-continued
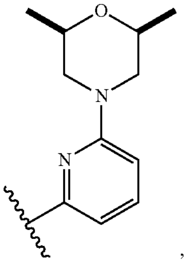,
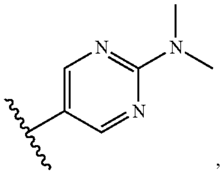,
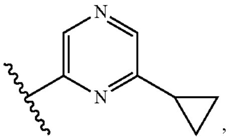,
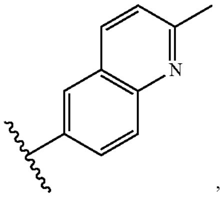, or
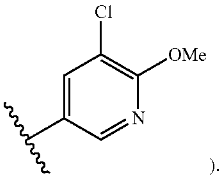).
In some embodiments, C is
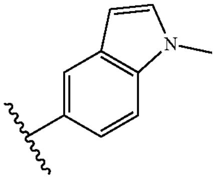,
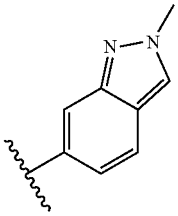,
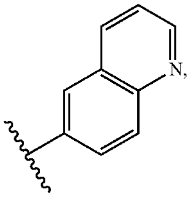
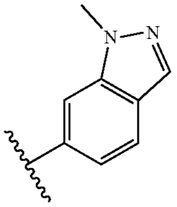,
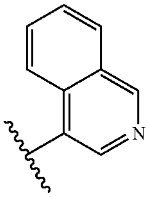,
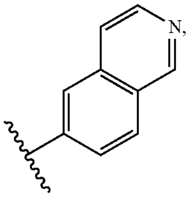
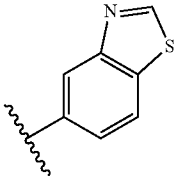,
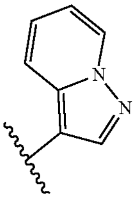,
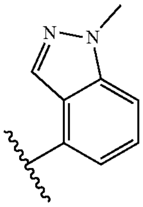,
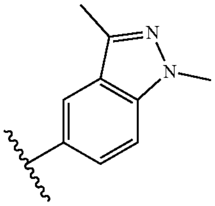,
-continued
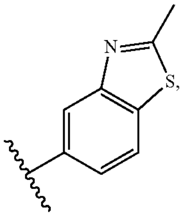
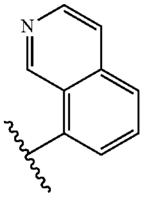,
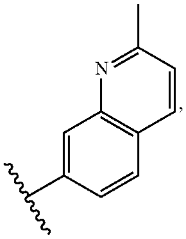
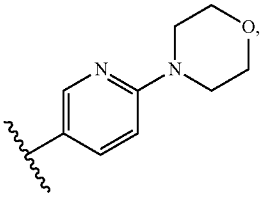
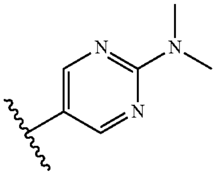,
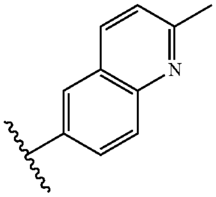, or
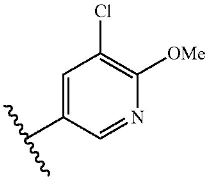.
In some embodiments, C is optionally substituted 5- to 10-membered heterocyclyl
(e.g., C is 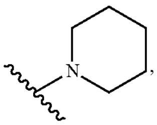, 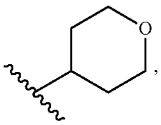, or 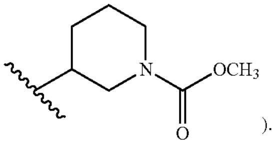).
In some embodiments, C is optionally substituted 5- to 10-membered heterocyclyl
(e.g., 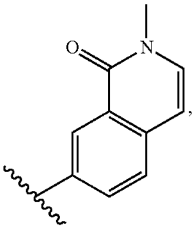, 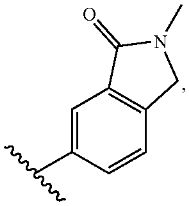, 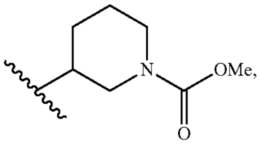 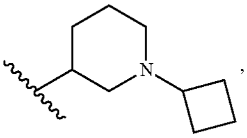, 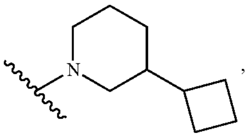, 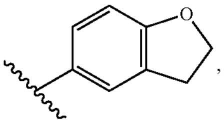, -continued
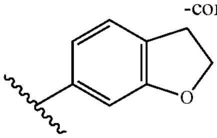, 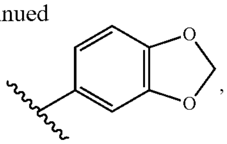,
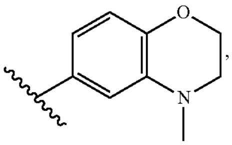, or 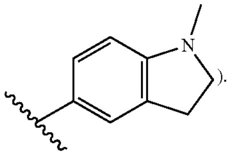).
In some embodiments, C is
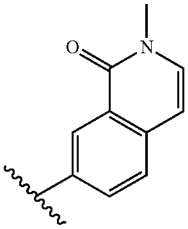, 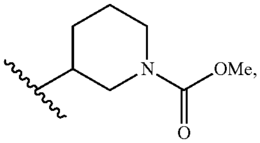
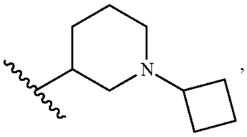, 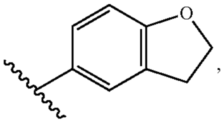,
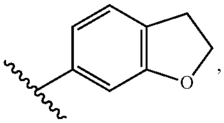, 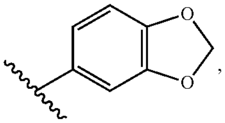,
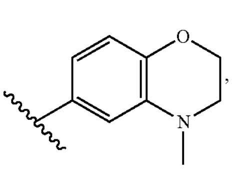, or 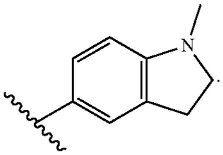.
In some embodiments, the compound is any one of compounds 1-82 in Table 1. In some embodiments, the compound is any one of compounds 1-74 in Table 1.
TABLE 1
Exemplary Compounds of the Invention
| # | Compound |
|---|---|
| 1 | 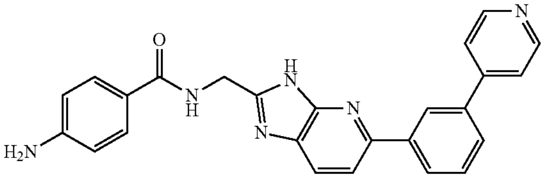 [SMILES: Nc1ccc(C(=O)NCc2nc3ccc(-c4cccc(-c5ccncc5)c4)nc3[nH]2)cc1] |
| 2 | 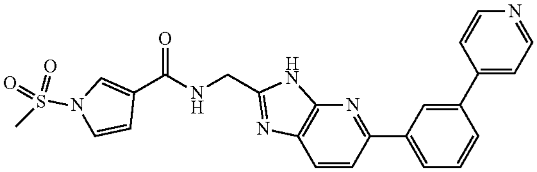 |
TABLE 1-continued
Exemplary Compounds of the Invention
| # | Compound |
|---|---|
| 3 | 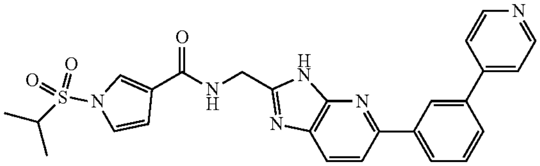 [SMILES: CC(C)S(=O)(=O)n1ccc(C(=O)NCc2nc3ccc(-c4cccc(-c5ccncc5)c4)nc3[nH]2)c1] |
| 4 | 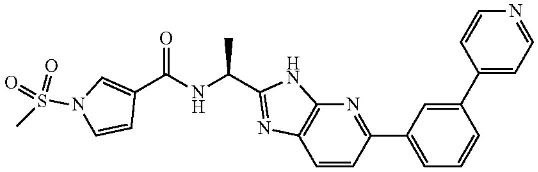 [SMILES: C[C@H](NC(=O)c1ccn(S(C)(=O)=O)c1)c1nc2ccc(-c3cccc(-c4ccncc4)c3)nc2[nH]1] |
| 5 | 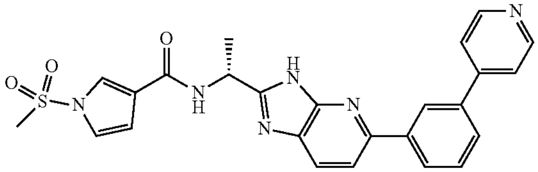 [SMILES: C[C@@H](NC(=O)c1ccn(S(C)(=O)=O)c1)c1nc2ccc(-c3cccc(-c4ccncc4)c3)nc2[nH]1] |
| 6 | 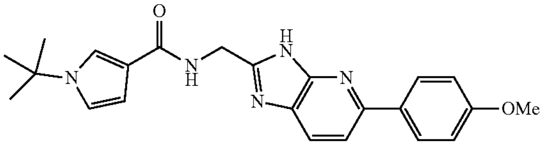 [SMILES: COc1ccc(-c2ccc3nc(CNC(=O)c4ccn(C(C)(C)C)c4)[nH]c3n2)cc1] |
| 7 | 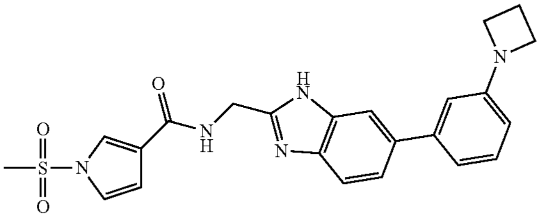 [SMILES: CS(=O)(=O)n1ccc(C(=O)NCc2nc3ccc(-c4cccc(N5CCC5)c4)cc3[nH]2)c1] |
| 8 | 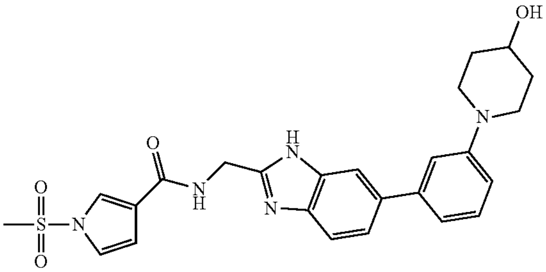 [SMILES: CS(=O)(=O)n1ccc(C(=O)NCc2nc3ccc(-c4cccc(N5CCC(O)CC5)c4)cc3[nH]2)c1] |
| 9 | 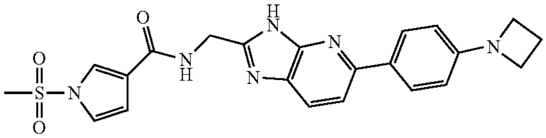 [SMILES: CS(=O)(=O)n1ccc(C(=O)NCc2nc3ccc(-c4ccc(N5CCC5)cc4)nc3[nH]2)c1] |

TABLE 1-continued
| Exemplary Compounds of the Invention | |
|---|---|
| # | Compound |
| 10 | 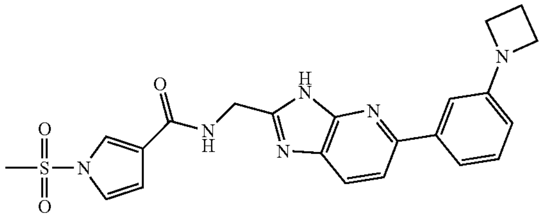 [SMILES: CS(=O)(=O)n1ccc(C(=O)NCc2nc3ccc(-c4cccc(N5CCC5)c4)nc3[nH]2)c1] |
| 11 | 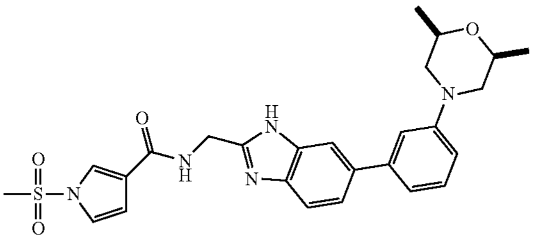 |
| 12 | 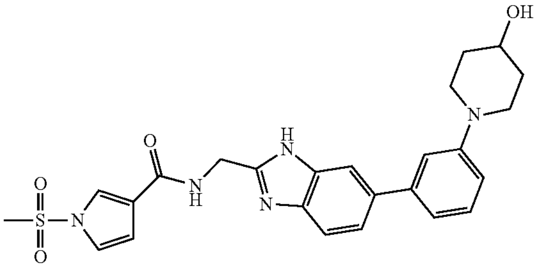 [SMILES: CS(=O)(=O)n1ccc(C(=O)NCc2nc3ccc(-c4cccc(N5CCC(O)CC5)c4)cc3[nH]2)c1] |
| 13 | 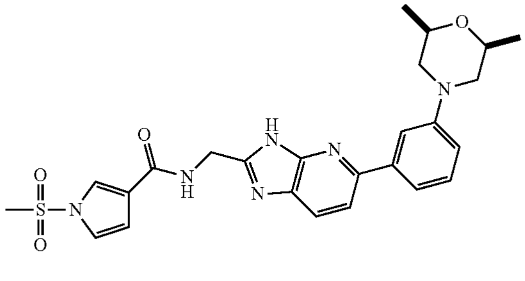 |
| 14 | 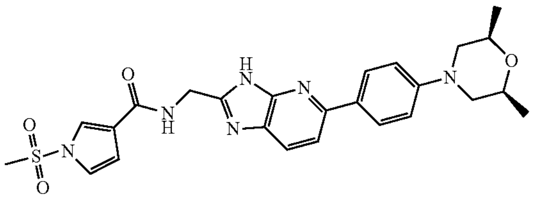 |
| 15 | 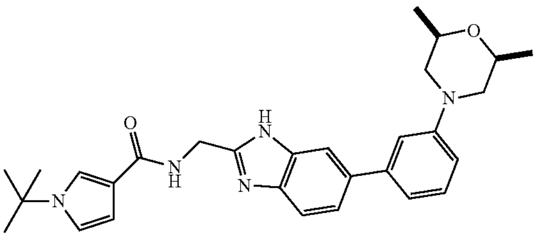 [SMILES: C[C@@H]1CN(c2cccc(-c3ccc4nc(CNC(=O)c5ccn(C(C)(C)C)c5)[nH]c4c3)c2)C[C@H](C)O1] |
TABLE 1-continued
| Exemplary Compounds of the Invention | |
|---|---|
| # | Compound |
| 16 | 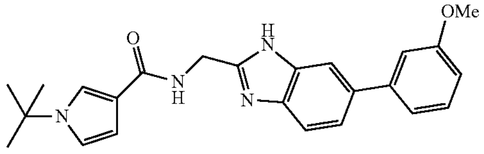 [SMILES: COc1cccc(-c2ccc3nc(CNC(=O)c4ccn(C(C)(C)C)c4)[nH]c3c2)c1] |
| 17 | 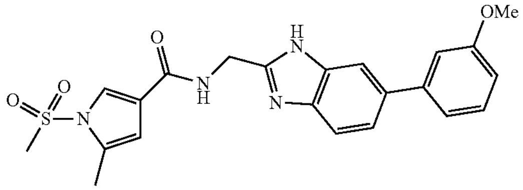 [SMILES: COc1cccc(-c2ccc3nc(CNC(=O)c4cc(C)n(S(C)(=O)=O)c4)[nH]c3c2)c1] |
| 18 | 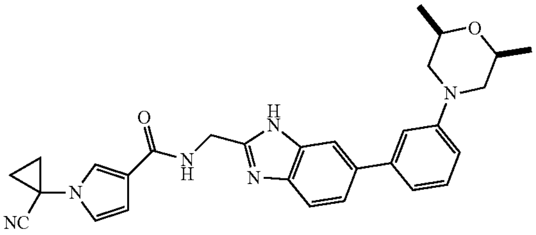 [SMILES: C[C@@H]1CN(c2cccc(-c3ccc4nc(CNC(=O)c5ccn(C6(C#N)CC6)c5)[nH]c4c3)c2)C[C@H](C)O1] |
| 19 | 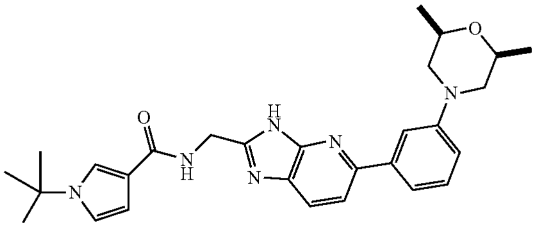 [SMILES: C[C@@H]1CN(c2cccc(-c3ccc4nc(CNC(=O)c5ccn(C(C)(C)C)c5)[nH]c4n3)c2)C[C@H](C)O1] |
| 20 | 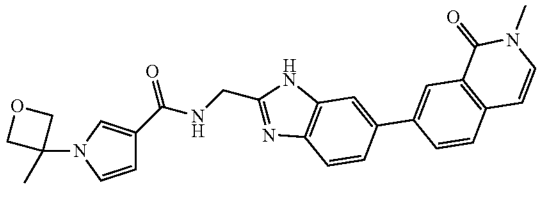 [SMILES: Cn1ccc2ccc(-c3ccc4nc(CNC(=O)c5ccn(C6(C)COC6)c5)[nH]c4c3)cc2c1=O] |
| 21 | 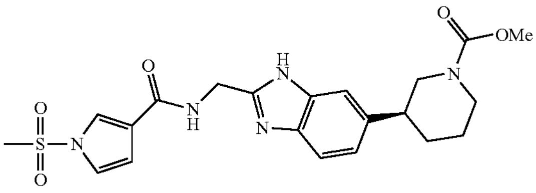 [SMILES: COC(=O)N1CCC[C@@H](c2ccc3nc(CNC(=O)c4ccn(S(C)(=O)=O)c4)[nH]c3c2)C1] |
| 22 | 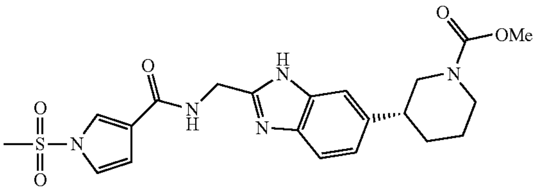 [SMILES: COC(=O)N1CCC[C@H](c2ccc3nc(CNC(=O)c4ccn(S(C)(=O)=O)c4)[nH]c3c2)C1] |

TABLE 1-continued
Exemplary Compounds of the Invention
| # | Compound |
|---|---|
| 23 | 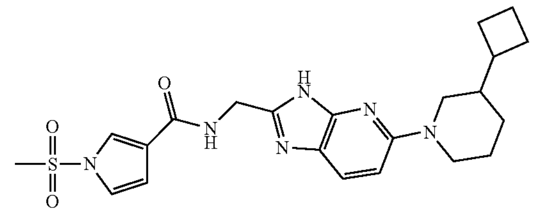 [SMILES: CS(=O)(=O)n1ccc(C(=O)NCc2nc3ccc(N4CCCC(C5CCC5)C4)nc3[nH]2)c1] |
| 24 | 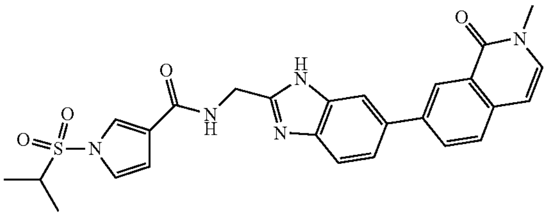 [SMILES: CC(C)S(=O)(=O)n1ccc(C(=O)NCc2nc3ccc(-c4ccc5ccn(C)c(=O)c5c4)cc3[nH]2)c1] |
| 25 | 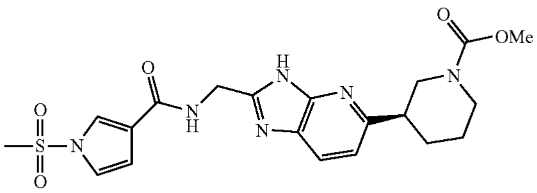 [SMILES: COC(=O)N1CCC[C@@H](c2ccc3nc(CNC(=O)c4ccn(S(C)(=O)=O)c4)[nH]c3n2)C1] |
| 26 | 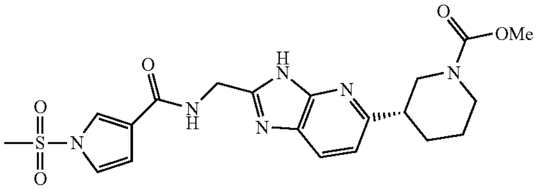 |
| 27 | 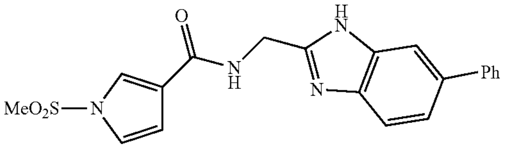 [SMILES: CS(=O)(=O)n1ccc(C(=O)NCc2nc3ccc(-c4ccccc4)cc3[nH]2)c1] |
| 28 | 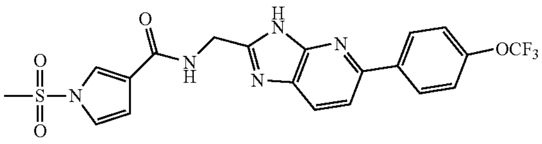 [SMILES: CS(=O)(=O)n1ccc(C(=O)NCc2nc3ccc(-c4ccc(OC(F)(F)F)cc4)nc3[nH]2)c1] |
| 29 | 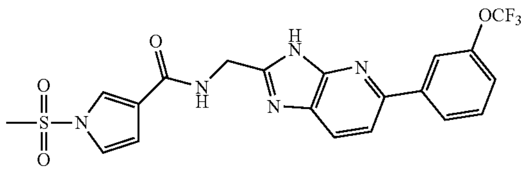 [SMILES: CS(=O)(=O)n1ccc(C(=O)NCc2nc3ccc(-c4cccc(OC(F)(F)F)c4)nc3[nH]2)c1] |
| 30 | 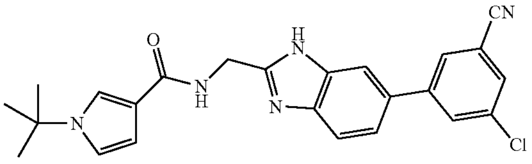 [SMILES: CC(C)(C)n1ccc(C(=O)NCc2nc3ccc(-c4cc(Cl)cc(C#N)c4)cc3[nH]2)c1] |
| 31 | 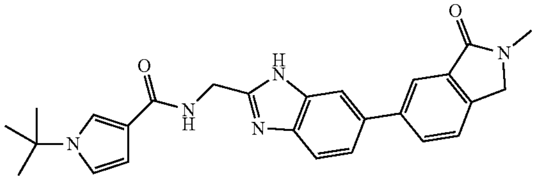 [SMILES: CN1Cc2ccc(-c3ccc4nc(CNC(=O)c5ccn(C(C)(C)C)c5)[nH]c4c3)cc2C1=O] |
| 32 | 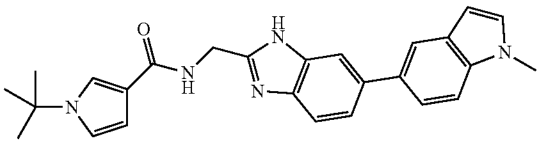 [SMILES: Cn1ccc2cc(-c3ccc4nc(CNC(=O)c5ccn(C(C)(C)C)c5)[nH]c4c3)ccc21] |
| 33 | 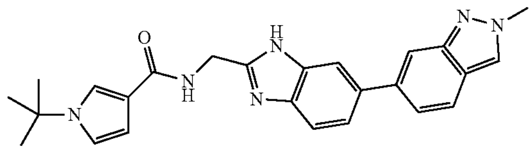 |
| 34 | 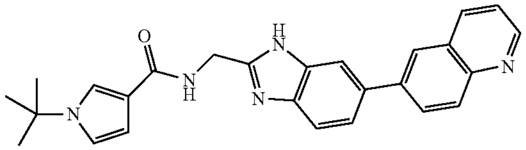 [SMILES: CC(C)(C)n1ccc(C(=O)NCc2nc3ccc(-c4ccc5ncccc5c4)cc3[nH]2)c1] |
| 35 | 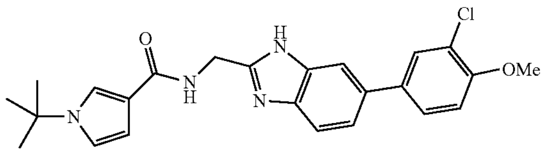 [SMILES: COc1ccc(-c2ccc3nc(CNC(=O)c4ccn(C(C)(C)C)c4)[nH]c3c2)cc1Cl] |
| 36 | 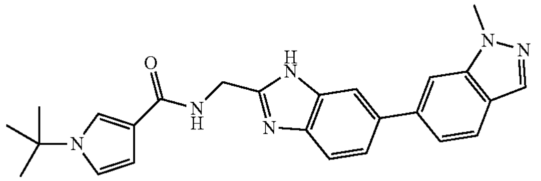 [SMILES: Cn1ncc2ccc(-c3ccc4nc(CNC(=O)c5ccn(C(C)(C)C)c5)[nH]c4c3)cc21] |
| 37 | 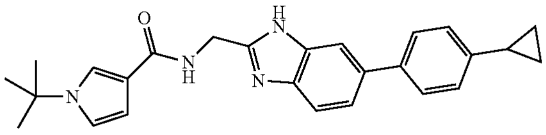 [SMILES: CC(C)(C)n1ccc(C(=O)NCc2nc3ccc(-c4ccc(C5CC5)cc4)cc3[nH]2)c1] |
| 38 | 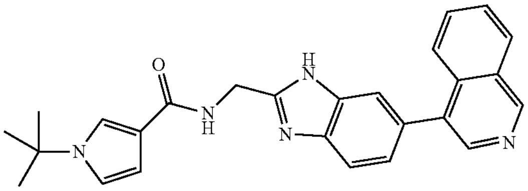 [SMILES: CC(C)(C)n1ccc(C(=O)NCc2nc3ccc(-c4cncc5ccccc45)cc3[nH]2)c1] |
| 39 | 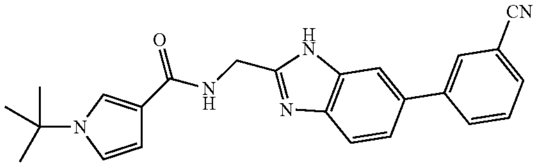 [SMILES: CC(C)(C)n1ccc(C(=O)NCc2nc3ccc(-c4cccc(C#N)c4)cc3[nH]2)c1] |

TABLE 1-continued
| Exemplary Compounds of the Invention | |
|---|---|
| # | Compound |
| 40 | 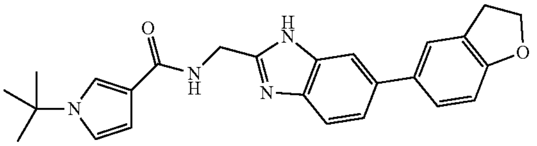 [SMILES: CC(C)(C)n1ccc(C(=O)NCc2nc3ccc(-c4ccc5c(c4)CCO5)cc3[nH]2)c1] |
| 41 | 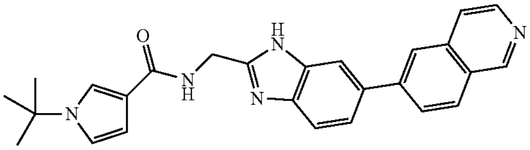 [SMILES: CC(C)(C)n1ccc(C(=O)NCc2nc3ccc(-c4ccc5cnccc5c4)cc3[nH]2)c1] |
| 42 | 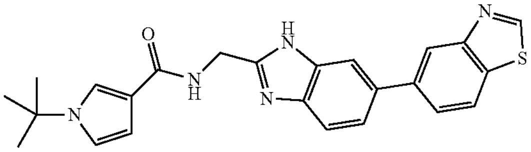 [SMILES: CC(C)(C)n1ccc(C(=O)NCc2nc3ccc(-c4ccc5scnc5c4)cc3[nH]2)c1] |
| 43 | 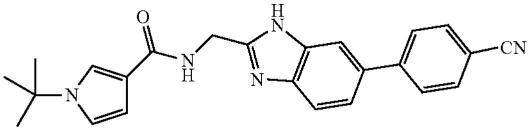 [SMILES: CC(C)(C)n1ccc(C(=O)NCc2nc3ccc(-c4ccc(C#N)cc4)cc3[nH]2)c1] |
| 44 | 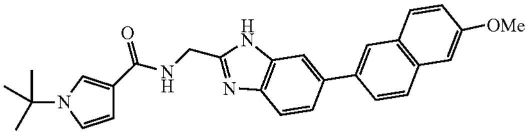 [SMILES: COc1ccc2cc(-c3ccc4nc(CNC(=O)c5ccn(C(C)(C)C)c5)[nH]c4c3)ccc2c1] |
| 45 | 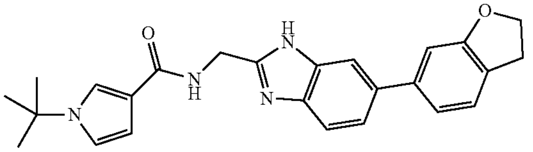 [SMILES: CC(C)(C)n1ccc(C(=O)NCc2nc3ccc(-c4ccc5c(c4)OCC5)cc3[nH]2)c1] |
| 46 | 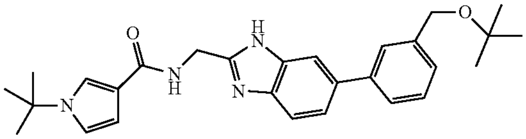 [SMILES: CC(C)(C)OCc1cccc(-c2ccc3nc(CNC(=O)c4ccn(C(C)(C)C)c4)[nH]c3c2)c1] |
| 47 | 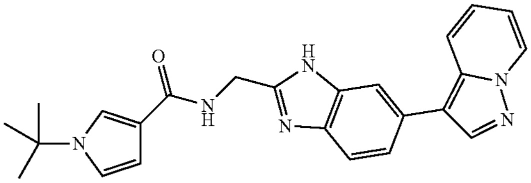 [SMILES: CC(C)(C)n1ccc(C(=O)NCc2nc3ccc(-c4cnn5ccccc45)cc3[nH]2)c1] |
| 48 | 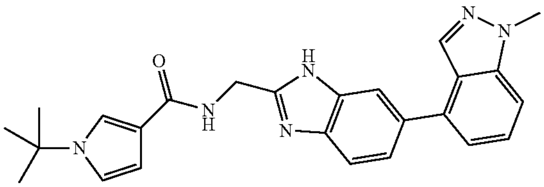 [SMILES: Cn1ncc2c(-c3ccc4nc(CNC(=O)c5ccn(C(C)(C)C)c5)[nH]c4c3)cccc21] |
TABLE 1-continued
| Exemplary Compounds of the Invention | |
|---|---|
| # | Compound |
| 49 | 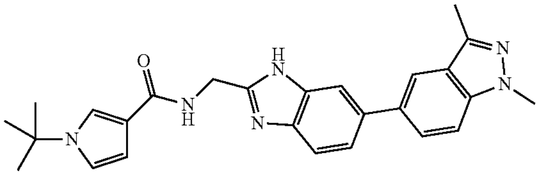 [SMILES: Cc1nn(C)c2ccc(-c3ccc4nc(CNC(=O)c5ccn(C(C)(C)C)c5)[nH]c4c3)cc12] |
| 50 | 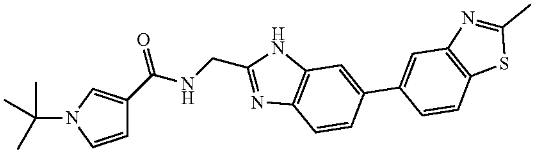 [SMILES: Cc1nc2cc(-c3ccc4nc(CNC(=O)c5ccn(C(C)(C)C)c5)[nH]c4c3)ccc2s1] |
| 51 | 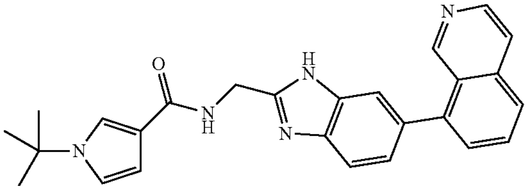 [SMILES: CC(C)(C)n1ccc(C(=O)NCc2nc3ccc(-c4cccc5ccncc45)cc3[nH]2)c1] |
| 52 | 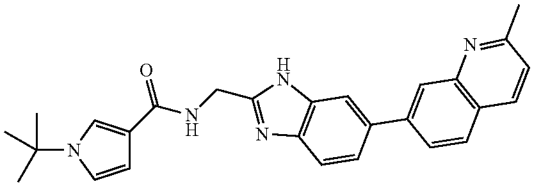 [SMILES: Cc1ccc2ccc(-c3ccc4nc(CNC(=O)c5ccn(C(C)(C)C)c5)[nH]c4c3)cc2n1] |
| 53 | 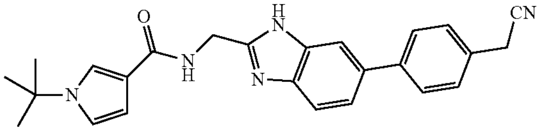 [SMILES: CC(C)(C)n1ccc(C(=O)NCc2nc3ccc(-c4ccc(CC#N)cc4)cc3[nH]2)c1] |
| 54 | 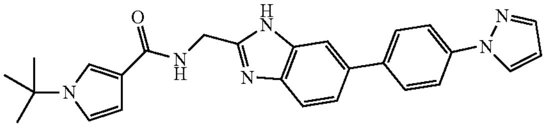 [SMILES: CC(C)(C)n1ccc(C(=O)NCc2nc3ccc(-c4ccc(-n5cccn5)cc4)cc3[nH]2)c1] |
| 55 | 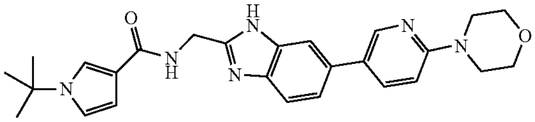 [SMILES: CC(C)(C)n1ccc(C(=O)NCc2nc3ccc(-c4ccc(N5CCOCC5)nc4)cc3[nH]2)c1] |
| 56 | 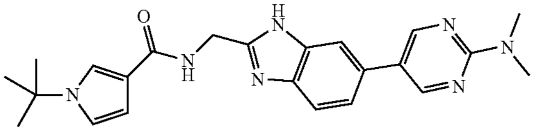 [SMILES: CN(C)c1ncc(-c2ccc3nc(CNC(=O)c4ccn(C(C)(C)C)c4)[nH]c3c2)cn1] |
| 57 | 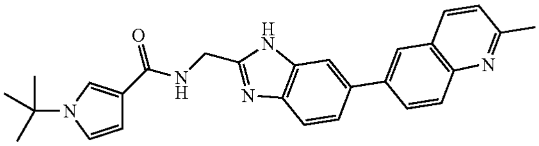 [SMILES: Cc1ccc2cc(-c3ccc4nc(CNC(=O)c5ccn(C(C)(C)C)c5)[nH]c4c3)ccc2n1] |

TABLE 1-continued
| Exemplary Compounds of the Invention | |
|---|---|
| # | Compound |
| 58 | 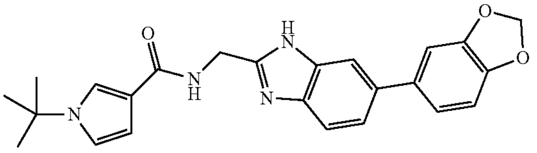 [SMILES: CC(C)(C)n1ccc(C(=O)NCc2nc3ccc(-c4ccc5c(c4)OCO5)cc3[nH]2)c1] |
| 59 | 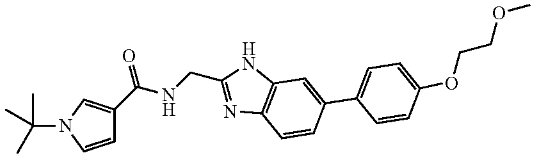 [SMILES: COCCOc1ccc(-c2ccc3nc(CNC(=O)c4ccn(C(C)(C)C)c4)[nH]c3c2)cc1] |
| 60 | 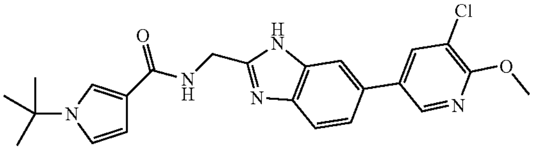 [SMILES: COc1ncc(-c2ccc3nc(CNC(=O)c4ccn(C(C)(C)C)c4)[nH]c3c2)cc1Cl] |
| 61 | 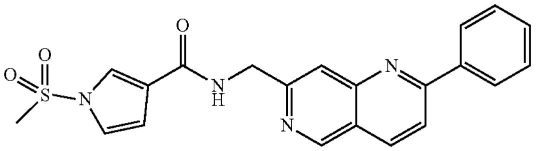 [SMILES: CS(=O)(=O)n1ccc(C(=O)NCc2cc3nc(-c4ccccc4)ccc3cn2)c1] |
| 62 | 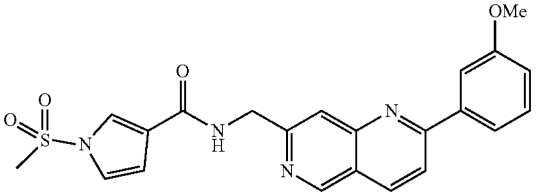 [SMILES: COc1cccc(-c2ccc3cnc(CNC(=O)c4ccn(S(C)(=O)=O)c4)cc3n2)c1] |
| 63 | 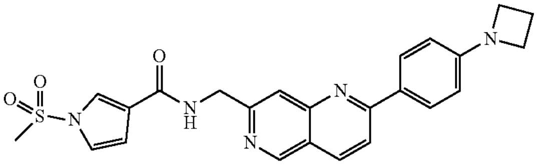 [SMILES: CS(=O)(=O)n1ccc(C(=O)NCc2cc3nc(-c4ccc(N5CCC5)cc4)ccc3cn2)c1] |
| 64 | 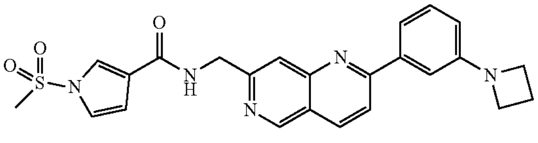 [SMILES: CS(=O)(=O)n1ccc(C(=O)NCc2cc3nc(-c4cccc(N5CCC5)c4)ccc3cn2)c1] |
| 65 | 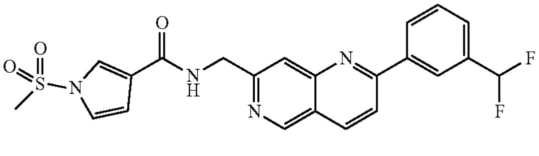 [SMILES: CS(=O)(=O)n1ccc(C(=O)NCc2cc3nc(-c4cccc(C(F)F)c4)ccc3cn2)c1] |
| 66 | 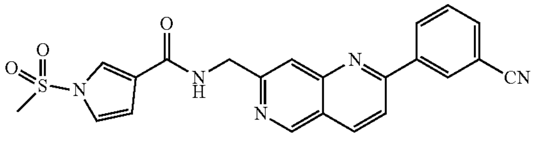 [SMILES: CS(=O)(=O)n1ccc(C(=O)NCc2cc3nc(-c4cccc(C#N)c4)ccc3cn2)c1] |
TABLE 1-continued
| Exemplary Compounds of the Invention | |
|---|---|
| # | Compound |
| 67 | 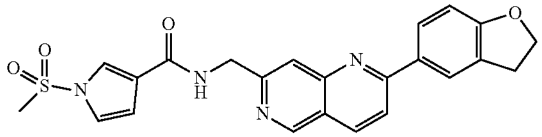 [SMILES: CS(=O)(=O)n1ccc(C(=O)NCc2cc3nc(-c4ccc5c(c4)CCO5)ccc3cn2)c1] |
| 68 | 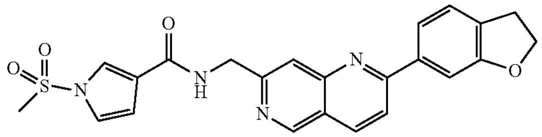 [SMILES: CS(=O)(=O)n1ccc(C(=O)NCc2cc3nc(-c4ccc5c(c4)OCC5)ccc3cn2)c1] |
| 69 | 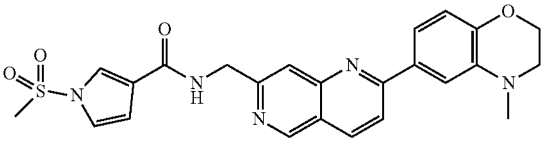 [SMILES: CN1CCOc2ccc(-c3ccc4cnc(CNC(=O)c5ccn(S(C)(=O)=O)c5)cc4n3)cc21] |
| 70 | 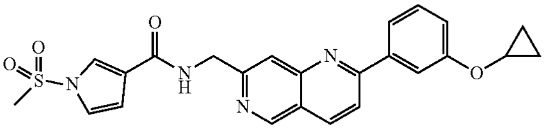 [SMILES: CS(=O)(=O)n1ccc(C(=O)NCc2cc3nc(-c4cccc(OC5CC5)c4)ccc3cn2)c1] |
| 71 | 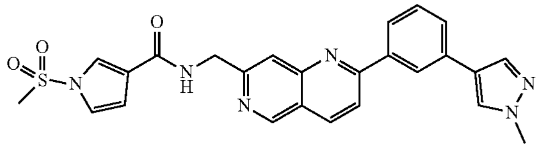 [SMILES: Cn1cc(-c2cccc(-c3ccc4cnc(CNC(=O)c5ccn(S(C)(=O)=O)c5)cc4n3)c2)cn1] |
| 72 | 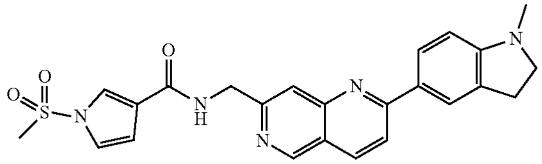 [SMILES: CN1CCc2cc(-c3ccc4cnc(CNC(=O)c5ccn(S(C)(=O)=O)c5)cc4n3)ccc21] |
| 73 | 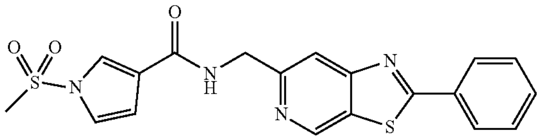 [SMILES: CS(=O)(=O)n1ccc(C(=O)NCc2cc3nc(-c4ccccc4)sc3cn2)c1] |
| 74 | 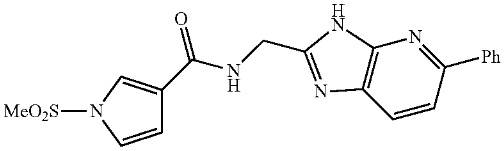 [SMILES: CS(=O)(=O)n1ccc(C(=O)NCc2nc3ccc(-c4ccccc4)nc3[nH]2)c1] |
| 75 | 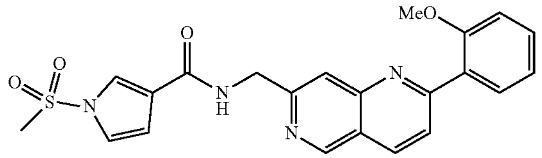 [SMILES: COc1ccccc1-c1ccc2cnc(CNC(=O)c3ccn(S(C)(=O)=O)c3)cc2n1] |

TABLE 1-continued

Exemplary Compounds of the Invention

| # | Compound |
|---|---|
| 76 | 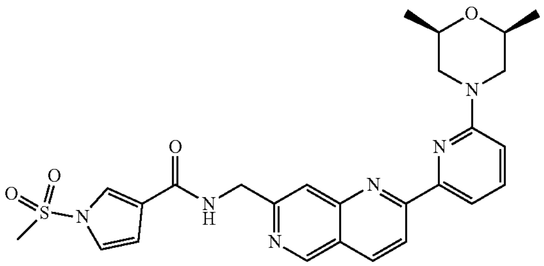 [SMILES: C[C@@H]1CN(c2cccc(-c3ccc4cnc(CNC(=O)c5ccn(S(C)(=O)=O)c5)cc4n3)n2)C[C@H](C)O1] |
| 77 | 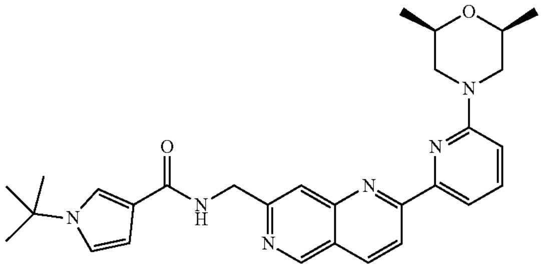 [SMILES: C[C@@H]1CN(c2cccc(-c3ccc4cnc(CNC(=O)c5ccn(C(C)(C)C)c5)cc4n3)n2)C[C@H](C)O1] |
| 78 | 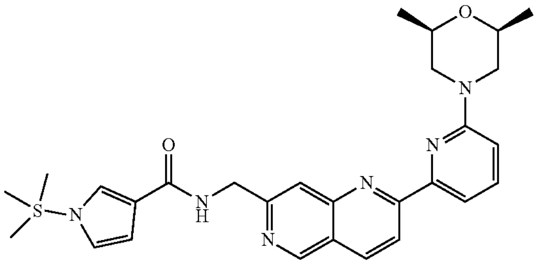 |
| 79 | 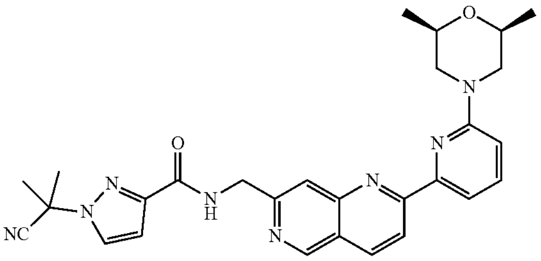 [SMILES: C[C@@H]1CN(c2cccc(-c3ccc4cnc(CNC(=O)c5ccn(C(C)(C)C#N)n5)cc4n3)n2)C[C@H](C)O1] |
| 80 | 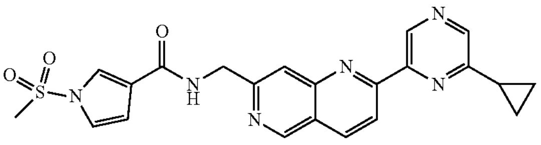 [SMILES: CS(=O)(=O)n1ccc(C(=O)NCc2cc3nc(-c4cncc(C5CC5)n4)ccc3cn2)c1] |
| 81 | 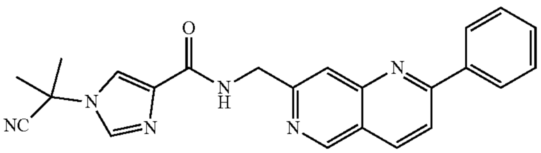 [SMILES: CC(C)(C#N)n1cnc(C(=O)NCc2cc3nc(-c4ccccc4)ccc3cn2)c1] |

TABLE 1-continued

Exemplary Compounds of the Invention

| # | Compound |
|---|---|
| 82 | 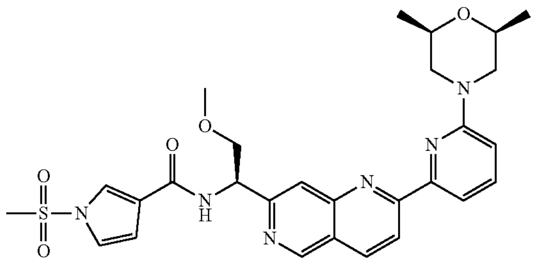 |

In another aspect, the invention features a pharmaceutical composition including any one of the above compounds and a pharmaceutically acceptable excipient.

In another aspect, the invention features a method of decreasing the activity of a BAF complex in a cell, the method involving contacting the cell with an effective amount of any of the foregoing compounds or a pharmaceutical composition thereof.

In some embodiments, the cell is a cancer cell.

In another aspect, the invention features a method of treating a BAF complex-related disorder in a subject in need thereof, the method involving administering to the subject an effective amount of any of the foregoing compounds or a pharmaceutical composition thereof.

In some embodiments, the BAF complex-related disorder is cancer or a viral infection.

In a further aspect, the invention features a method of inhibiting BRM, the method involving contacting a cell with an effective amount of any of the foregoing compounds or a pharmaceutical composition thereof. In some embodiments, the cell is a cancer cell.

In another aspect, the invention features a method of inhibiting BRG1, the method involving contacting the cell with an effective amount of any of the foregoing compounds or a pharmaceutical composition thereof. In some embodiments, the cell is a cancer cell.

In a further aspect, the invention features a method of inhibiting BRM and BRG1, the method involving contacting the cell with an effective amount of any of the foregoing compounds or a pharmaceutical composition thereof. In some embodiments, the cell is a cancer cell.

In another aspect, the invention features a method of treating a disorder related to a BRG1 loss of function mutation in a subject in need thereof, the method involving administering to the subject an effective amount of any of the foregoing compounds or a pharmaceutical composition thereof.

In some embodiments, the disorder related to a BRG1 loss of function mutation is cancer. In other embodiments, the subject is determined to have a BRG1 loss of function disorder, for example, is determined to have a BRG1 loss of function cancer (for example, the cancer has been determined to include cancer cells with loss of BRG1 function).

In another aspect, the invention features a method of inducing apoptosis in a cell, the method involving contacting the cell with an effective amount of any of the foregoing compounds or a pharmaceutical composition thereof. In some embodiments, the cell is a cancer cell.

In a further aspect, the invention features a method of treating cancer in a subject in need thereof, the method including administering to the subject an effective amount of any of the foregoing compounds or a pharmaceutical composition thereof.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, or penile cancer.

In some embodiments of any of the foregoing methods, the cancer is a drug resistant cancer or has failed to respond to a prior therapy (e.g., vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inihibitors, alimta, abraxane, Adriamycin®, gemcitabine, avastin, halaven, neratinib, a PARP inhibitor, ARN810, an mTOR inhibitor, topotecan, gemzar, a VEGFR2 inhibitor, a folate receptor antagonist, demcizumab, fosbretabulin, or a PDL1 inhibitor).

In some embodiments of any of the foregoing methods, the cancer has or has been determined to have BRG1 mutations. In some embodiments of any of the foregoing methods, the BRG1 mutations are homozygous. In some embodiments of any of the foregoing methods, the cancer does not have, or has been determined not to have, an epidermal growth factor receptor (EGFR) mutation. In some embodiments of any of the foregoing methods, the cancer does not have, or has been determined not to have, an anaplastic lymphoma kinase (ALK) driver mutation. In some embodiments of any of the foregoing methods, the cancer has, or has been determined to have, a KRAS mutation. In some embodiments of any of the foregoing methods, the BRG1 mutation is in the ATPase catalytic domain of the protein. In some embodiments of any of the foregoing methods, the BRG1 mutation is a deletion at the C-terminus of BRG1.

In another aspect, the disclosure provides a method treating a disorder related to BAF (e.g., cancer or viral infections) in a subject in need thereof. This method includes contacting a cell with an effective amount of any of the foregoing compounds, or pharmaceutically acceptable salts thereof, or any of the foregoing pharmaceutical compositions. In some embodiments, the disorder is a viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), Togaviridae family (e.g., Rubella virus). In some embodiments, the disorder is Coffin Siris, Neurofibromatosis (e.g., NF-1, NF-2, or Schwannomatosis), or Multiple Meningioma.

In another aspect, the disclosure provides a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), or Togaviridae family (e.g., Rubella virus).

In another aspect, the invention features a method of treating melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of reducing tumor growth of melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of suppressing metastatic progression of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of suppressing metastatic colonization of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of reducing the level and/or activity of BRG1 and/or BRM in a melanoma, prostate cancer, breast cancer, bone cancer, renal cell carcinoma, or hematologic cancer cell, the method including contacting the cell with an effective amount of any of the foregoing compounds or pharmaceutical compositions thereof.

In some embodiments of any of the above aspects, the melanoma, prostate cancer, breast cancer, bone cancer, renal cell carcinoma, or hematologic cell is in a subject.

In some embodiments of any of the above aspects, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRG1 by at least 50% (e.g., 55%, 60%, 65%, 70%, 75%, 80%, 85%, 90%, or 95%) as compared to a reference. In some embodiments, the effective amount of the compound that reduces the level and/or activity of BRG1 by at least 90% (e.g., 91%, 92%, 93%, 94%, 95%, 96%, 97%, 98%, or 99%).

In some embodiments, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments of any of the above aspects, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRM by at least 50% (e.g., 55%, 60%, 65%, 70%, 75%, 80%, 85%, 90%, or 95%) as compared to a reference. In some embodiments, the effective amount of the compound that reduces the level and/or activity of BRM by at least 90% (e.g., 91%, 92%, 93%, 94%, 95%, 96%, 97%, 98%, or 99%).

In some embodiments, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the subject has cancer. In some embodiments, the cancer expresses BRG1 and/or BRM protein and/or the cell or subject has been identified as expressing BRG1 and/or BRM. In some embodiments, the cancer expresses BRG1 protein and/or the cell or subject has been identified as expressing BRG1. In some embodiments, the cancer expresses BRM protein and/or the cell or subject has been identified as expressing BRM. In some embodiments, the cancer is melanoma (e.g., uveal melanoma, mucosal melanoma, or cutaneous melanoma). In some embodiments, the cancer is prostate cancer. In some embodiments, the cancer is a hematologic cancer, e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia (e.g., T-cell acute lymphoblastic leukemia or B-cell acute lymphoblastic leukemia), diffuse large cell lymphoma, or non-Hodgkin's lymphoma. In some embodiments, the cancer is breast cancer (e.g., an ER positive breast cancer, an ER negative breast cancer, triple positive breast cancer, or triple negative breast cancer). In some embodiments, the cancer is a bone cancer (e.g., Ewing's sarcoma). In some embodiments, the cancer is a renal cell carcinoma (e.g., a Microphthalmia Transcription Factor (MITF) family translocation renal cell carcinoma (tRCC)). In some embodiments, the cancer is metastatic (e.g., the cancer has spread to the liver). The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer. The metastatic cancer can be a cancer spread via seeding the surface of the peritoneal, pleural, pericardial, or subarachnoid spaces. Alternatively, the metastatic cancer can be a cancer spread via the lymphatic system, or a cancer spread hematogenously. In some embodiments, the effective amount of an agent that reduces the level and/or activity of BRG1 and/or BRM is an amount effective to inhibit metastatic colonization of the cancer to the liver.

In some embodiments the cancer harbors a mutation in GNAQ. In some embodiments the cancer harbors a mutation in GNA11. In some embodiments the cancer harbors a mutation in PLCB4. In some embodiments the cancer harbors a mutation in CYSLTR2. In some embodiments the cancer harbors a mutation in BAP1. In some embodiments the cancer harbors a mutation in SF3B1. In some embodiments the cancer harbors a mutation in EIF1AX. In some embodiments the cancer harbors a TFE3 translocation. In some embodiments the cancer harbors a TFEB translocation. In some embodiments the cancer harbors a MITF translocation. In some embodiments the cancer harbors an EZH2 mutation. In some embodiments the cancer harbors a SUZ12 mutation. In some embodiments the cancer harbors an EED mutation.

In some embodiments of any of the foregoing methods, the method further includes administering to the subject or contacting the cell with an anticancer therapy, e.g., a chemotherapeutic or cytotoxic agent, immunotherapy, surgery, radiotherapy, thermotherapy, or photocoagulation, or a combination thereof. In some embodiments, the anticancer therapy is a chemotherapeutic or cytotoxic agent, e.g., an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor, or a combination thereof.

In some embodiments of any of the foregoing methods, the compound of the invention is used in combination with another anti-cancer therapy used for the treatment of uveal melanoma such as surgery, a MEK inhibitor, and/or a PKC inhibitor. For example, in some embodiments, the method further comprises performing surgery prior to, subsequent to, or at the same time as administration of the compound of the invention. In some embodiments, the method further comprises administration of a MEK inhibitor and/or a PKC inhibitor prior to, subsequent to, or at the same time as administration of the compound of the invention.

In some embodiments, the anticancer therapy and the compound of the invention are administered within 28 days of each other and each in an amount that together are effective to treat the subject.

In some embodiments, the subject or cancer has and/or has been identified as having a BRG1 loss of function mutation. In some embodiments, the subject or cancer has and/or has been identified as having a BRM loss of function mutation.

In some embodiments, the cancer is resistant to one or more chemotherapeutic or cytotoxic agents (e.g., the cancer has been determined to be resistant to chemotherapeutic or cytotoxic agents such as by genetic markers, or is likely to be resistant, to chemotherapeutic or cytotoxic agents such as a cancer that has failed to respond to a chemotherapeutic or cytotoxic agent). In some embodiments, the cancer has failed to respond to one or more chemotherapeutic or cytotoxic agents. In some embodiments, the cancer is resistant or has failed to respond to dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or IDE196).

In some embodiments, the cancer is resistant to or failed to respond to a previously administered therapeutic used for the treatment of uveal melanoma such as a MEK inhibitor or PKC inhibitor. For example, in some embodiments, the cancer is resistant to or failed to respond to a mitogen-activated protein kinase (MEK) inhibitor (e.g., selumetinib, binimetinib, or tametinib), and/or a protein kinase C (PKC) inhibitor (e.g., sotrastaurin or IDE196).

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as H atoms, or substituent groups, as described herein, may be present, as necessary, to satisfy the valences of the atoms. For example, an unsubstituted $C_2$ alkyl group has the formula $—CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a H or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms). An "alkylene" is a divalent alkyl group.

The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6 carbon atoms, or 2 carbon atoms).

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6 carbon atoms, or 2 carbon atoms).

The term "amino," as used herein, represents $—N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., $—NH_2$) or a substituted amino (i.e., $—N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl. An "arylene" is a divalent aryl group.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a $—N_3$ group.

The term "cyano," as used herein, represents a —CN group.

The term "cycloalkyl," as used herein, refers to a saturated, non-aromatic, and monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A "heteroalkylene" is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

The term "heteroaryl," as used herein, refers to an aromatic mono- or polycyclic radical of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl. A "heteroarylene" is a divalent heteroaryl group.

The term "heterocyclyl," as used herein, refers to a mono- or polycyclic radical having 3 to 12 atoms having at least one non-aromatic ring containing 1, 2, 3, or 4 ring atoms selected from N, O or S and no aromatic ring containing any N, O, or S atoms. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an $—NO_2$ group.

The term "oxo," as used herein, represents an =O group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, oxo, acyl, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{11}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "comprising" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1- or HBRM-associated factors complex in a human cell.

As used herein, the term "BAF complex-related disorder" refers to a disorder that is caused or affected by the level of activity of a BAF complex.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

By "determining the level" of a protein or RNA is meant the detection of a protein or an RNA, by methods known in the art, either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure RNA levels are known in the art and include, but are not limited to, quantitative polymerase chain reaction (qPCR) and Northern blot analyses.

By a "decreased level" or an "increased level" of a protein or RNA is meant a decrease or increase, respectively, in a protein or RNA level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein in a sample.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

As used herein, the term "inhibiting BRM" refers to blocking or reducing the level or activity of the ATPase catalytic binding domain or the bromodomain of the protein. BRM inhibition may be determined using methods known in the art, e.g., a BRM ATPase assay, a Nano DSF assay, or a BRM Luciferase cell assay.

As used herein, the term "LXS196," also known as IDE196, refers to the PKC inhibitor having the structure:

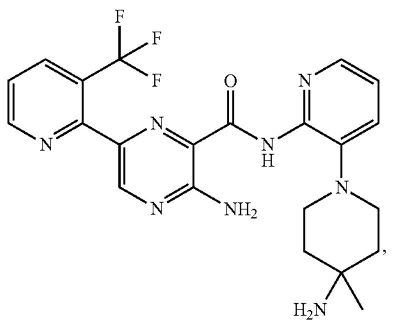 [SMILES: CC1(N)CCN(c2cccnc2NC(=O)c2nc(-c3ncccc3C(F)(F)F)cnc2N)CC1]

or a pharmaceutically acceptable salt thereof.

The term "pharmaceutical composition," as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of a compound, for example, any compound of Formula I. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

By a "reference" is meant any useful reference used to compare protein or RNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean therapeutic treatment or any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

The present disclosure features compounds useful for the inhibition of BRG1 and/or BRM. These compounds may be used to modulate the activity of a BAF complex, for example, for the treatment of a BAF-related disorder, such as cancer. Exemplary compounds described herein include compounds having a structure according to Formula I:

Formula I

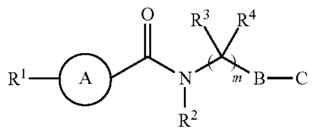

wherein $R^1$ is H, optionally substituted $C_1$-$C_6$ acyl, optionally substituted $C_1$-$C_6$ alkyl, optionally substituted $C_1$-$C_6$ heteroalkyl, optionally substituted $C_3$-$C_8$ cycloalkyl, optionally substituted $C_2$-$C_9$ heterocyclyl, optionally substituted amino, or —$SO_2R^6$;

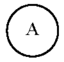

is optionally substituted arylene, optionally substituted 5-membered heteroarylene, or optionally substituted 6-membered heteroarylene;

m is 0, 1, 2, or 3;

B is an optionally substituted 9- or 10-membered bicyclic heteroarylene;

C is optionally substituted 3- to 10-membered cycloalkyl; optionally substituted 6- to 10-membered aryl; optionally substituted 5- to 10-membered heteroaryl; or optionally substituted 5- to 10-membered heterocyclyl;

$R^2$ is hydrogen or optionally substituted $C_1$-$C_6$ alkyl;

each of $R^3$ and $R^4$ is, independently, hydrogen, optionally substituted $C_1$-$C_6$ alkyl, or optionally substituted $C_1$-$C_6$ heteroalkyl;

$R^5$ is optionally substituted $C_1$-$C_6$ alkyl or —$NR^6R^7$; and each of $R^6$ and $R^7$ is, independently, optionally substituted $C_1$-$C_6$ alkyl, or a pharmaceutically acceptable salt thereof.

In some embodiments, the compound, or pharmaceutically acceptable salt thereof, has the structure of any one of Compounds 1-82 in Table 1.

Other embodiments, as well as exemplary methods for the synthesis of production of these compounds, are described herein.

Pharmaceutical Uses

The compounds described herein are useful in the methods of the invention and, while not bound by theory, are believed to exert their ability to modulate the level, status, and/or activity of a BAF complex, i.e., by inhibiting the activity of the BRG1 and/or BRM proteins within the BAF complex in a mammal. BAF complex-related disorders include, but are not limited to, BRG1 loss of function mutation-related disorders.

An aspect of the present invention relates to methods of treating disorders related to BRG1 loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. In some embodiments, the present invention relates to methods of treating melanoma (e.g., uveal melanoma), prostate cancer, breast cancer, bone cancer, renal cell carcinoma, or a hematologic cancer.

In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, hematologic cancer, and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chlorambucil; Gemzar® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (Ibritumomab tiuxetan); Humira (Adalimumab); Xolair (Omalizumab); Bexxar (Tositumomab-1-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab/Yervoy or tremelimumab). In some embodiments, the inhibitor of checkpoint is an inhibitor (e.g., an inhibitory antibody or small molecule inhibitor) of PD-1 (e.g., nivolumab/Opdivo®; pembrolizumab/Keytruda®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MED14736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK1, CHK2, A2aR, B-7 family ligands, or a combination thereof.

In some embodiments, the compound of the invention is used in combination with another anti-cancer therapy used for the treatment of uveal melanoma such as surgery, a MEK inhibitor, and/or a PKC inhibitor, or a combination thereof. For example, in some embodiments, the method further comprises performing surgery prior to, subsequent to, or at the same time as administration of the compound of the invention. In some embodiments, the method further comprises administration of a MEK inhibitor (e.g., selumetinib, binimetinib, or tametinib) and/or a PKC inhibitor (e.g., sotrastaurin or IDE196) prior to, subsequent to, or at the same time as administration of the compound of the invention.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The compounds of the invention are preferably formulated into pharmaceutical compositions for administration to a mammal, preferably, a human, in a biologically compatible form suitable for administration in vivo. Accordingly, in an aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, ortransdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard- or soft-shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Alternatively, the dosage amount can be calculated using the body weight of the patient. For example, the dose of a compound, or pharmaceutical composition thereof, administered to a patient may range from 0.1-100 mg/kg.

EXAMPLES

Definitions Used in the Following Schemes and Elsewhere Herein are

ACN acetonitrile
AcOH or HOAc acetic acid
aq. aqueous
Boc tert-butoxycarbonyl
$B_2pin_2$ 4,4,5,5-tetramethyl-2-(4,4,5,5-tetramethyl-1,3,2-dioxaborolan-2-yl)-1,3,2-dioxaborolane
t-BuONa or NaOt-Bu sodium tert-butoxide
Cbz benzyloxy carbonyl
DCE dichloroethane
DCM dichloromethane
DIBAL-H diisobutylaluminum hydride
DIEA or DIPEA N,N-diisopropylethylamine
DMA N,N-dimethylacetamide
DME 1,2-dimethoxyethane
DMF N,N-dimethylformamide
DMSO dimethylsulfoxide
EDCI or EDCI.HCl 1-ethyl-(3-dimethylaminopropyl)carbodiimide hydrochloride
ES electrospray ionization
$Et_3N$ or TEA triethylamine
EtOAc ethyl acetate
EtOH ethyl alcohol
FA formic acid
h hour
HATU 2-(3H-[1,2,3]triazolo[4,5-b]pyridin-3-yl)-1,1,3,3-tetramethylisouronium
HBTU N,N,N',N'-tetramethyl-O-(1H-benzotriazol-1-yl)uronium hexafluorophosphate
HCl hydrochloric acid
HOAc acetic acid
HOBt or HOBT hydroxybenzotriazole hydrate
KOAc potassium acetate
KHMDS potassium hexamethyldisilazide
LED light-emitting diode
Me methyl
MeOH methyl alcohol
MsCl methanesulfonyl chloride
NaHMDS sodium hexamethyldisilazide
NIS N-iodosuccinimide
OAc acetate
Pd/C palladium on carbon
$Pd_2(dba)_3$ tris(dibenzylideneacetone)dipalladium(0)
$Pd(dppf)Cl_2$ or $(DPPF)PdCl_2$ [1,1'-bis(diphenylphosphino)ferrocene]dichloropalladium(II)
$Pd(dtbpf)Cl_2$ dichloro[1,1'-bis(di-t-butylphosphino)ferrocene]palladium(II)
Ph phenyl
PhMe toluene
PTFE poly(tetrafluoroethylene)
SFC supercritical fluid chromatography
SPhos Pd G3 (2-dicyclohexylphosphino-2',6'-dimethoxybiphenyl) [2-(2'-amino-1,1'-biphenyl)]palladium(II) methanesulfonate
THF tetrahydrofuran
Xantphos 9,9-dimethyl-4,5-bis(diphenylphosphino)xanthene Materials Unless otherwise noted, all materials were obtained from commercial suppliers and were used without further purification. All reactions involving air- or moisture-sensitive reagents were performed under a nitrogen atmosphere.

Example 1. Preparation of tert-butyl ((5-(3-(pyridine-4-yl)phenyl-1H-imiadzo[4,5-b]pyridine-2-yl)methyl)carbamate, (S)-tert-butyl (1-(5-(3-(pyridin-4-yl)phenyl)-1H-imidazo[4,5-b]pyridin-2-yl)ethyl)carbamate, and (R)-tert-butyl (1-(5-(3-(pyridin-4-yl)phenyl)-1H-imidazo[4,5-b]pyridin-2-yl)ethyl)carbamate (Intermediate 1-3)

Intermediate 1: tert-butyl ((5-(3-(pyridine-4-yl)phenyl-1H-imiadzo[4,5-b]pyridine-2-yl)methyl)carbamate

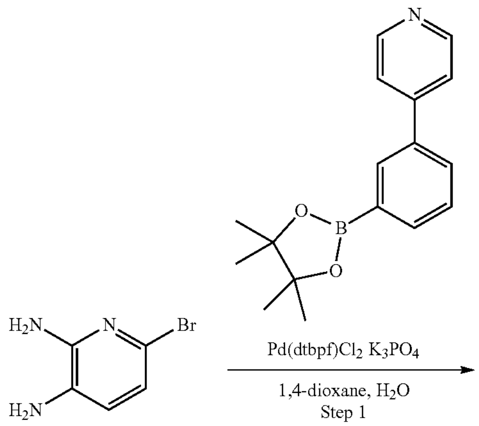

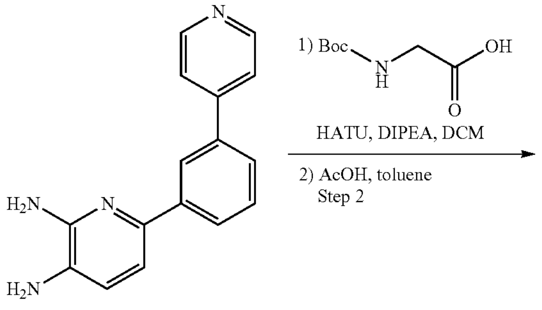

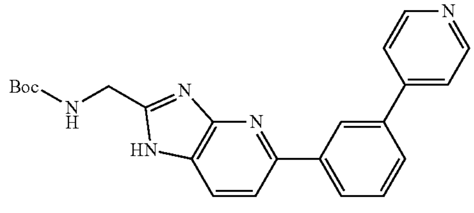

Intermediate 1

Step 1: Preparation of 6-(3-(pyridin-4-yl)phenyl)pyridine-2,3-diamine

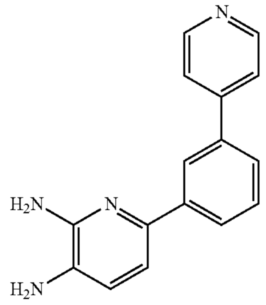 [SMILES: Nc1ccc(-c2cccc(-c3ccncc3)c2)nc1N]

To a solution of 6-bromopyridine-2,3-diamine (500 mg, 2.66 mmol) in 1,4-dioxane (4 mL) was added water (1 mL), 4-[3-(4,4,5,5-tetramethyl-1,3,2-dioxaborolan-2-yl)phenyl]pyridine (2.24 g, 7.98 mmol), $K_3PO_4$ (1.69 g, 7.98 mmol) and [1,1'-bis(di-tert-butylphosphino)ferrocene]dichloropalladium (173 mg, 0.266 mmol). After stirring at 120° C. for 17 h, the reaction mixture was poured into water, then extracted four times with ethyl acetate. The combined organic layer was washed with brine, dried over anhydrous sodium sulfate, filtered and concentrated to give residue. The residue was purified by reversed-phase prep-HPLC ($NH_3$—$H_2O$) to afford the title compound (470 mg, 1.68 mmol, 63.3% yield) as a white solid. LCMS (ESI) m/z: [M+H]+=263.3. $^1$H NMR (400 MHz, DMSO-$d_6$) δ 8.68-8.61 (m, 2H), 8.26-8.25 (m, 1H), 7.96-7.95 (m, 1H), 7.77-7.70 (m, 2H), 7.65-7.60 (m, 1H), 7.54-7.47 (m, 1H), 7.13 (d, J=7.6 Hz, 1H), 6.80 (d, J=7.6 Hz, 1H), 5.53 (s, 2H), 4.90 (s, 2H).

Step 2: Preparation of tert-butyl ((5-(3-(pyridine-4-yl)phenyl-1H-imiadzo[4,5-b]pyridine-2-yl)methyl)carbamate (Intermediate 1)

Intermediate 1

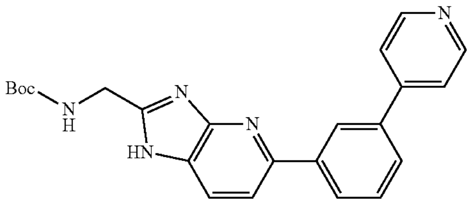

To a solution of 2-(tert-butoxycarbonylamino)acetic acid (330 mg, 1.88 mmol) in DMF (5 mL) was added HATU (1.02 g, 2.69 mmol), DIPEA (695 mg, 5.38 mmol) and 6-(3-(pyridin-4-yl)phenyl)pyridine-2,3-diamine (470 mg, 1.79 mmol). After stirring at room temperature for 0.5 h, the reaction mixture was poured into water, then extracted twice with ethyl acetate. The combined organic layer was washed with brine, dried over anhydrous sodium sulfate, filtered and concentrated to give residue. The residue was purified by reversed-phase prep-HPLC ($NH_3 \cdot H_2O$) to afford an intermediate (600 mg, 1.40 mmol, 78.2% yield) as a white solid. The solid was dissolved in toluene (6 mL) and acetic acid (85.9 mg, 1.43 mmol) was added to the mixture. After stirring at 120° C. for 12 h, the reaction mixture was poured into water, then extracted three times with ethyl acetate. The combined organic layer was washed with brine, dried over anhydrous sodium sulfate, filtered and concentrated to afford Intermediate 1 (500 mg, 1.15 mmol, 80.1% yield) as yellow oil. LCMS (ESI) m/z: [M+H]+=402.4. $^{1}$H NMR (400 MHz, DMSO-$d_6$) δ 13.10-12.46 (m, 1H), 8.69 (d, J=6.0 Hz, 2H), 8.47 (s, 1H), 8.21 (d, J=8.0 Hz, 1H), 8.05 (br d, J=8.0 Hz, 1H), 7.95 (br s, 2H), 7.85-7.80 (m, 3H), 7.69-7.59 (m, 1H), 4.41 (br s, 2H), 1.43 (s, 9H).

Intermediates 2 and 3: (S)-tert-butyl (1-(5-(3-(pyridin-4-yl)phenyl)-1H-imidazo[4,5-b]pyridin-2-yl)ethyl)carbamate and (R)-tert-butyl (1-(5-(3-(pyridin-4-yl)phenyl)-1H-imidazo[4,5-b]pyridin-2-yl)ethyl)carbamate Intermediate 2

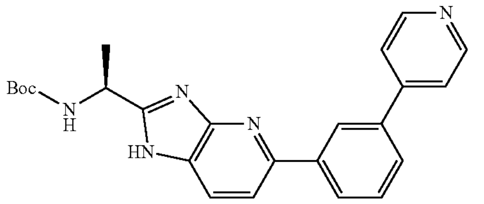

Intermediate 3

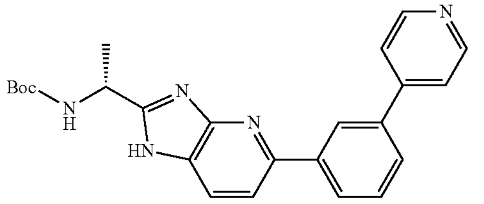

Intermediates 2 and 3 were synthesized starting from the common intermediate 6-(3-(pyridin-4-yl)phenyl)pyridine-2,3-diamine and corresponding racemic N-Boc amino acid utilizing the above-described synthetic protocol for preparing Intermediate 1, followed by a chiral SFC separation.

Intermediate 2: LCMS (ESI) m/z: [M+H]+=416.1.

Intermediate 3: LCMS (ESI) m/z: [M+H]+=416.2.

Example 2. Preparation of tert-butyl ((5-(3-cyclobutylpiperidin-1-yl)-3H-imidazo[4,5-b]pyridin-2-yl)methyl)carbamate (Intermediate 4)

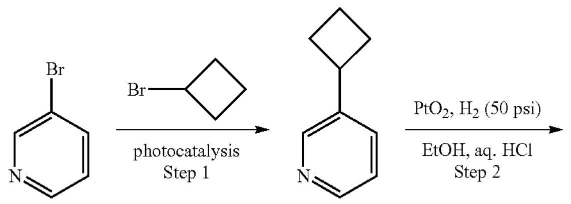

-continued

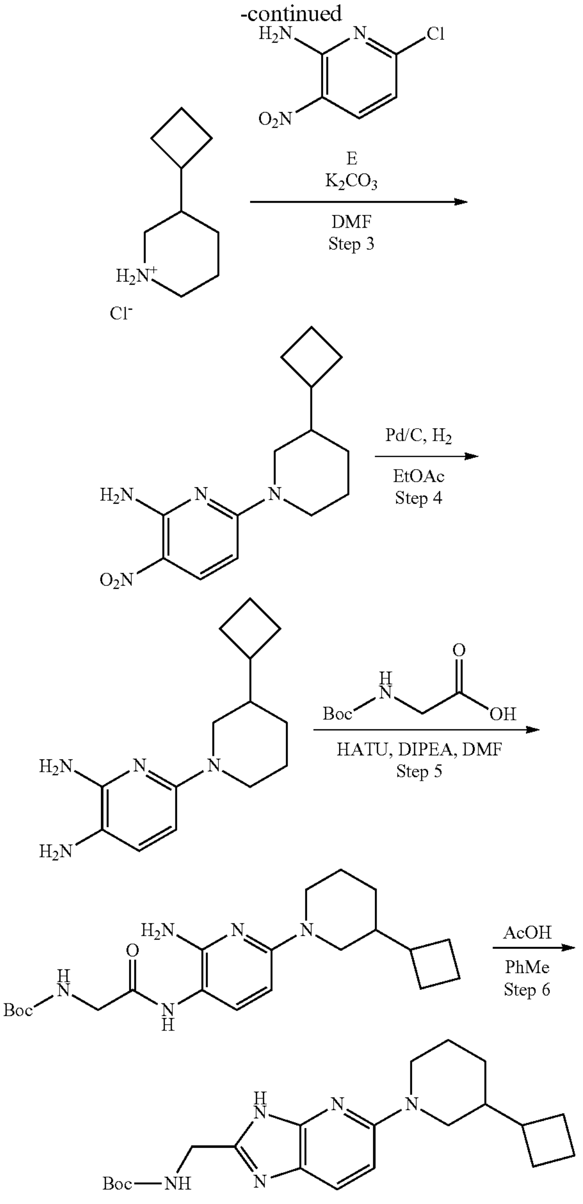

Intermediate 4

Step 1: Preparation of 3-cyclobutylpyridine

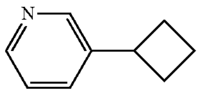

To a vial was added 3-bromopyridine (6.10 mL, 63.3 mmol), bromocyclobutane (7.77 mL, 82.3 mmol), (4,4'-di-t-butyl-2,2'-bipyridine)bis[3,5-difluoro-2-[5-trifluoromethyl-2-pyridinyl-κN)phenyl-κC]iridium(III) hexafluorophosphate (710 mg, 0.633 mmol), nickel(II) chloride, dimethoxyethane adduct (69.5 mg, 0.316 mmol), 4-tert-butyl-2-(4-tert-butyl-2-pyridyl)pyridine (102 mg, 0.380 mmol), bis(trimethylsilyl)silyl-trimethyl-silane (19.5 mL, 63.3 mmol) and $K_2CO_3$ (17.5 g, 127 mmol) in acetonitrile (240 mL). The vial was sealed and placed under a nitrogen atmosphere and irradiated with a 34 W blue LED lamp (7 cm away) at room temperature. After 14 h, the reaction mixture was diluted with water and extracted three times with ethyl acetate, and the combined organic layers were dried over anhydrous $Na_2SO_4$ and concentrated to afford a yellow oil. The oil was purified by flash silica gel chromatography (0-50% ethyl acetate/petroleum ether gradient) to afford the title compound (1.6 g, 12.0 mmol, 17.1% yield) as a yellow oil. LCMS (ESI) m/z: $[M+H]^+$=134.1. $^1H$ NMR (400 MHz, $CDCl_3$) δ 8.36-8.31 (m, 2H), 7.45-7.42 (m, 1H), 7.13-7.10 (m, 1H), 3.50-3.41 (m, 1H), 2.44-2.26 (m, 2H), 2.06-1.96 (m, 3H), 1.86-1.81 (m, 1H).

Step 2: Preparation of methyl 3-cyclobutylpiperidin-1-ium chloride

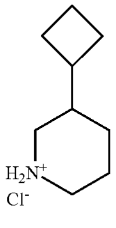

To a mixture of 3-cyclobutylpyridine (1.6 g, 12.0 mmol) in ethanol (16 mL) was added $PtO_2$ (327 mg, 1.44 mmol) and an aqueous concentrated HCl solution (1.60 mL) at room temperature. The mixture was degassed and purged with $H_2$ three times, then stirred at 60° C. under $H_2$ atmosphere (50 psi). After 18 h, the reaction mixture was diluted with methanol and filtered. The filtrate was concentrated to afford the title compound (2.00 g, 11.4 mmol, 94.2% yield) as a yellow oil. LCMS (ESI) m/z: $[M+H]^+$=140.3. $^1H$ NMR (400 MHz, DMSO-$d_6$) δ 9.20 (br s, 1H), 8.98 (s, 1H), 3.11-3.01 (m, 2H), 2.72-2.63 (m, 1H), 2.40-2.31 (m, 1H), 2.06-2.02 (m, 1H), 1.95-1.90 (m, 2H), 1.79-1.58 (m, 8H), 1.01-0.91 (m, 1H).

Step 3: Preparation of 6-(3-cyclobutylpiperidin-1-yl)-3-nitropyridin-2-amine

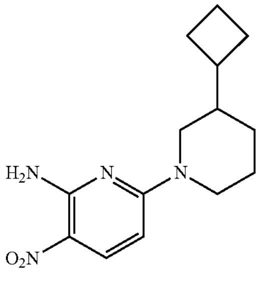 [SMILES: Nc1nc(N2CCCC(C3CCC3)C2)ccc1[N+](=O)[O-]]

To a mixture of methyl 3-cyclobutylpipderdin-1-ium chloride (2 g, 11.4 mmol) and $K_2CO_3$ (6.29 g, 45.5 mmol) in DMF (20 mL) was added 6-chloro-3-nitro-pyridin-2-amine (2.17 g, 12.5 mmol) at room temperature. After stirring at 80° C. for 2 h, the reaction mixture was diluted with water and extracted three times with ethyl acetate; the combined organic layers were concentrated to afford a yellow oil. The oil was purified by reversed-phase prep-HPLC ($NH_3 \cdot H_2O$), concentrated to remove acetonitrile and the mixture was extracted twice with ethyl acetate. The combined organic layers were dried over anhydrous $Na_2SO_4$, filtered and concentrated under vacuum to afford the title compound (2.2 g, 7.96 mmol, 69.8% yield) as a yellow solid. LCMS (ESI) m/z: $[M+H]^+$=277.2. $^1H$ NMR (400 MHz, DMSO-$d_6$) δ 8.05-7.68 (m, 3H), 6.34 (d, J=9.6 Hz, 1H), 4.25-4.16 (m, 1H), 3.15-3.09 (m, 1H), 2.76-2.75 (m, 1H), 2.07-2.03 (m, 2H), 1.99-1.95 (m, 1H), 1.80-1.72 (m, 6H), 1.43-1.40 (m, 3H), 1.15-1.10 (m, 1H).

Step 4: Preparation of 6-(3-cyclobutylpiperidin-1-yl)pyridine-2,3-diamine

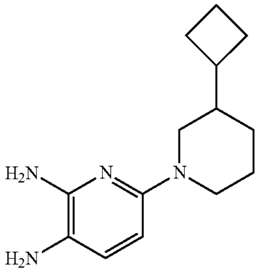 [SMILES: Nc1ccc(N2CCCC(C3CCC3)C2)nc1N]

A mixture of 6-(3-cyclobutylpiperidin-1-yl)-3-nitro-pyridine-2-diamine (500 mg, 1.81 mmol) and 10% Pd/C (250 mg, 1.81 mmol) in ethyl acetate (5 mL) was degassed and purged with $H_2$ (15 psi) three times. After stirring at room temperature under a $H_2$ atmosphere for 12 h, the reaction mixture was filtered and the filtrate was concentrated under vacuum to afford the title compound (420 mg, 1.70 mmol, 94.2% yield) as a black oil which was used to the next step without further purification. LCMS (ESI) m/z; $[M+H]^+$=247.3. $^1H$ NMR (400 MHz, DMSO-$d_6$) δ 6.68 (d, J=8.0 Hz, 1H), 5.80 (d, J=8.0 Hz, 1H), 5.09 (s, 2H), 3.93 (br s, 2H), 3.84-3.77 (m, 2H), 2.47-2.44 (m, 1H), 2.06-2.06 (m, 1H), 2.05-1.93 (m, 3H), 1.86-1.61 (m, 6H), 1.47-1.37 (m, 2H), 0.91-0.86 (m, 1H).

Step 5: Preparation of tert-butyl (2-((2-amino-6-(3-cyclobutylpiperidin-1-yl)pyridin-3-yl)amino)-2-oxo-ethyl)carbamate

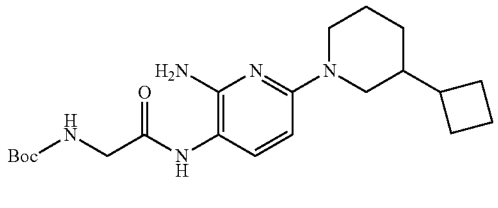 [SMILES: CC(C)(C)OC(=O)NCC(=O)Nc1ccc(N2CCCC(C3CCC3)C2)nc1N]

To a mixture of 2-(tert-butoxycarbonylamino)acetic acid (219 mg, 1.25 mmol) and HATU (713 mg, 1.88 mmol) in DMF (4 mL) was added DIPEA (0.653 mL, 3.75 mmol). After stirring at room temperature for 15 minutes, 6-(3-cyclobutylpiperidin-1-yl)pyridine-2,3-diamine (370 mg, 1.50 mmol) was added the mixture. After stirring an addition 2 h, the reaction mixture was diluted with water and extracted three times with ethyl acetate; the combined organic layers were concentrated to afford a black brown oil. The oil was purified by flash silica gel chromatography (0-80% ethyl acetate/petroleum ether gradient) to afford the title compound (280 mg, 694 μmol, 55.5% yield) as a black oil. LCMS (ESI) m/z: $[M+H]^+$=404.1. $^1H$ NMR (400 MHz, DMSO-$d_6$) δ 8.84 (s, 1H), 7.13 (d, J=8.4 Hz, 1H), 7.01-8.98 (m, 1H), 5.92 (d, J=8.4 Hz, 1H), 5.33 (s, 2H), 3.97-3.94 (m, 1H), 3.68 (br d, J=5.6 Hz, 2H), 2.69-2.67 (m, 1H), 2.34-2.31 (m, 1H), 2.14-2.00 (m, 2H), 1.97-1.96 (m, 1H), 1.74-1.59 (m, 7H), 1.39 (s, 11H), 0.98-0.97 (m, 1H).

Step 6: Preparation of tert-butyl ((5-(3-cyclobutylpiperidin-1-yl)-3H-imidazo[4,5-b]pyridin-2-yl)methyl)carbamate (Intermediate 4)

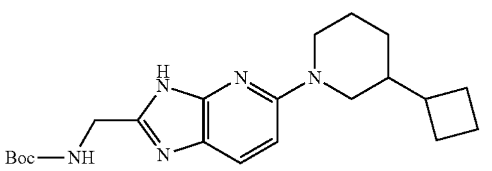 [SMILES: CC(C)(C)OC(=O)NCc1nc2ccc(N3CCCC(C4CCC4)C3)nc2[nH]1]

To a mixture of tert-butyl (2-((2-amino-6-(3-cyclobutylpiperidin-1-yl)pyridin-3-yl)amino)-2-oxoethyl)carbamate (280 mg, 694 μmol) in toluene (3 mL) was added acetic acid (0.061 mL, 1.07 mmol) at room temperature. After stirring at 100° C. for 12 h, the reaction mixture was diluted with water and extracted four times with ethyl acetate; the combined organic layers were concentrated to afford a black brown oil. The oil was purified by silica gel flash chromatography (0-100% ethyl acetate/petroleum ether gradient) to afford Intermediate 4 (130 mg, 0.337 mmol, 48.6% yield) as a brown oil. LCMS (ESI) m/z: $[M+H]^+$=386.2. $^1H$ NMR (400 MHz, DMSO-$d_6$) δ 12.26 (s, 1H), 7.67-7.65 (m, 1H), 7.23-7.21 (m, 1H), 6.68-6.64 (m, 1H), 4.24 (d, J=5.6 Hz, 2H), 4.09 (d, J=1.6 Hz, 1H), 2.79-2.77 (m, 1H), 2.41-2.38 (m, 1H), 2.08-2.02 (m, 3H), 1.82-1.65 (m, 7H), 1.39 (s, 11H), 1.02-0.96 (m, 1H).

Example 3. Preparation of 4-amino-N-((5-(3-(pyridin-4-yl)phenyl)-3H-imidazo[4,5-b]pyridin-2-yl)methyl)benzamide (Compound 1)

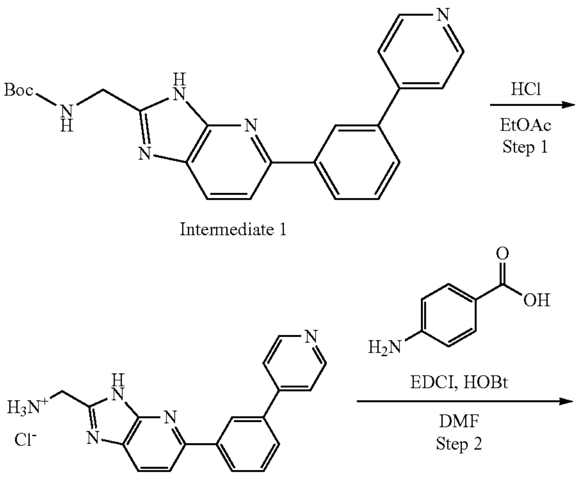

-continued

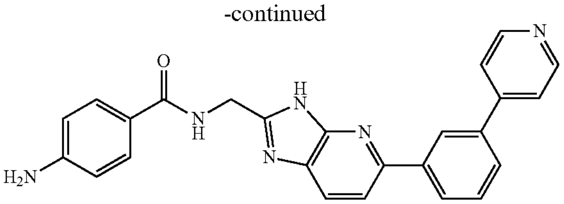

Compound 1

Step 1: Preparation of (5-(3-(pyridin-4-yl)phenyl)-3H-imidazo[4,5-b]pyridin-2-yl)methanaminium chloride

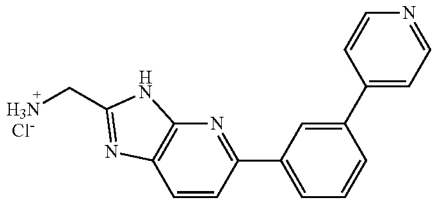 [SMILES: [Cl-] ; NCc1nc2ccc(-c3cccc(-c4ccncc4)c3)nc2[nH]1]

A solution of Intermediate 1 (500 mg, 1.25 mmol) in a solution of 4 M HCl in ethyl acetate (10 mL, 40 mmol) was stirred at room temperature. After 1 h, the reaction mixture was concentrated to afford the title compound (400 mg, 1.13 mmol, 91.0% yield) as a gray solid, which was used for next step without further purification. LCMS (ESI) m/z: $[M+H]^+$=302.1. $^1H$ NMR (400 MHz, DMSO-$d_6$) δ 9.03 (br d, J=6.6 Hz, 3H), 8.96 (br s, 2H), 8.68 (s, 1H), 8.56 (d, J=6.6 Hz, 2H), 8.39 (br d, J=7.8 Hz, 1H), 8.25-8.18 (m, 1H), 8.17-8.07 (m, 2H), 7.85-7.71 (m, 1H), 4.43 (br s, 2H).

Step 2: Preparation of 4-amino-N-((5-(3-(pyridin-4-yl)phenyl)-3H-imidazo[4,5-b]pyridin-2-yl)methyl) benzamide (Compound 1)

Compound 1

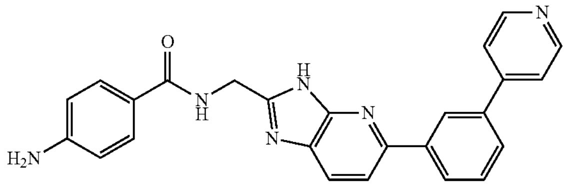

To a solution of (5-(3-(pyridin-4-yl)phenyl)-3H-imidazo[4,5-b]pyridin-2-yl)methanaminium chloride (60 mg, 0.178 mmol), 4-aminobenzoic acid (24.4 mg, 0.178 mmol), EDCI (68.1 mg, 0.355 mmol), HOBt (48.0 mg, 0.355 mmol) in dichloromethane (1 mL) was added DIPEA (0.155 mL, 0.888 mmol). After stirring at room temperature for 16 h, the reaction mixture was concentrated to afford the crude product. The crude product was purified by reversed-phase prep-HPLC (water:ACN;FA) to afford Compound 1 (7.98 mg, 17.11 μmol, 9.63% yield, formic acid salt) as a yellow solid. LCMS (ESI) m/z: $[M+H]^+$=421.2. $^1H$ NMR (400 MHz, DMSO-$d_6$) δ 8.92 (br d, J=4.6 Hz, 2H), 8.85 (s, 1H), 8.61 (s, 1H), 8.38-8.26 (m, 3H), 8.13 (d, J=4.8 Hz, 2H), 8.02 (br d, J=7.6 Hz, 1H), 7.80-7.64 (m, 3H), 6.63 (d, J=8.4 Hz, 2H), 4.77 (br d, J=5.4 Hz, 2H).

Example 4. Preparation of Compounds 2 to 5 and 23

Compounds 2 to 5 and 23, shown in Table 2 below, were each synthesized from Intermediate 1, 2, 3, or 4 and the corresponding carboxylic acid following the synthetic protocol described in Example 3.

TABLE 2

| # | LC-MS (m/z) | $^1$H NMR |
|---|---|---|
| 2 | 473.1 | $^1$H NMR (400 MHz, DMSO-$d_6$) δ 9.02-9.01 (m, 1H), 8.89 (br d, J = 5.6 Hz, 2H), 8.60 (s, 1H), 8.31 (br d, J = 8.0 Hz, 1H), 8.25 (br d, J = 6.0 Hz, 2H), 8.09-8.08 (m, 2H), 7.99 (br d, J = 7.6 Hz, 1H), 7.89 (s, 1H), 7.75-7.74 (m, 1H), 7.34 (br s, 1H), 6.82 (br d, J = 1.2 Hz, 1H), 4.73 (br d, J = 5.6 Hz, 2H), 3.58 (s, 3H) |
| 3 | 501.2 | $^1$H NMR (400 MHz, DMSO-$d_6$) δ 8.99 (br s, 1H), 8.69 (d, J = 4.8 Hz, 2H), 8.48 (s, 1H), 8.21 (d, J = 7.6 Hz, 1H), 8.09-7.93 (m, 2H), 7.89-7.76 (m, 4H), 7.66-7.65 (m, 1H), 7.30 (d, J = 2.0 Hz, 1H), 6.91-6.77 (m, 1H), 4.69 (br d, J = 5.6 Hz, 2H), 3.96-3.80 (m, 1H), 1.24 (d, J = 6.8 Hz, 6H) |
| 4 | 487.2 | $^1$H NMR (400 MHz, DMSO-$d_6$) δ 8.90 (d, J = 6.8 Hz, 2H), 8.82 (d, J = 7.2 Hz, 1H), 8.62-8.61 (m, 1H), 8.33-8.29 (m, 3H), 8.10-8.04 (m, 2H), 8.00-7.98 (m, 1H), 7.96-7.95 (m, 1H), 7.75-7.71 (m, 1H), 7.32-7.31 (m, 1H), 6.81-6.80 (m, 1H), 5.40-5.33 (m, 1H), 3.56 (s, 3H), 1.65 (d, J = 7.2 Hz, 3H) |
| 5 | 487.2 | $^1$H NMR (400 MHz, DMSO-$d_6$) δ 8.91 (br d, J = 4.4 Hz, 2H), 8.80 (br d, J = 7.2 Hz, 1H), 8.61 (s, 1H), 8.33-8.31 (m, 3H), 8.10-8.04 (m, 2H), 8.00 (br d, J = 7.6 Hz, 1H), 7.96-7.95 (m, 1H), 7.75-7.71 (m, 1H), 7.31-7.30 (m, 1H), 6.81-6.80 (m, 1H), 5.40-5.33 (m, 1H), 3.56 (s, 3H), 1.65 (d, J = 7.2 Hz, 3H) |
| 23 | 457.1 | $^1$H NMR (400 MHz, methanol-$d_4$) δ 7.83-7.82 (m, 1H), 7.68 (d, J = 8.8 Hz, 1H), 7.25-7.24 (m, 1H), 6.80-6.79 (m, 1H), 6.73 (d, J = 8.8 Hz, 1H), 4.69 (s, 2H), 4.17-4.09 (m, 2H), 3.35 (s, 3H), 2.90-2.86 (m, 1H), 2.46-2.43 (m, 1H), 2.15-2.00 (m, 3H), 1.92-1.71 (m, 6H), 1.60-1.45 (m, 2H), 1.09-0.99 (m, 1H) |

Example 5. Preparation of N-((6-(3-(4-hydroxypiperidin-1-yl)phenyl)-1H-benzo[d]imidazol-2-yl)methyl)-1-(methylsulfonyl)-1H-pyrrole-3-carboxamide (Compound 8)

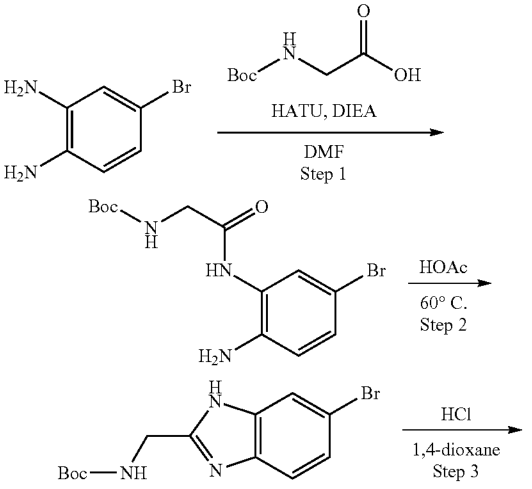

Intermediate 5

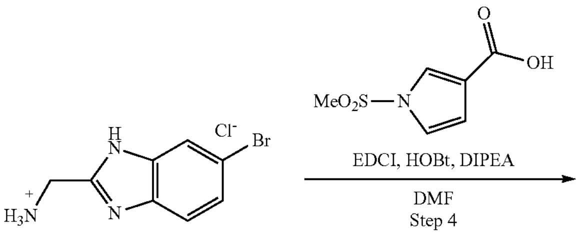

-continued

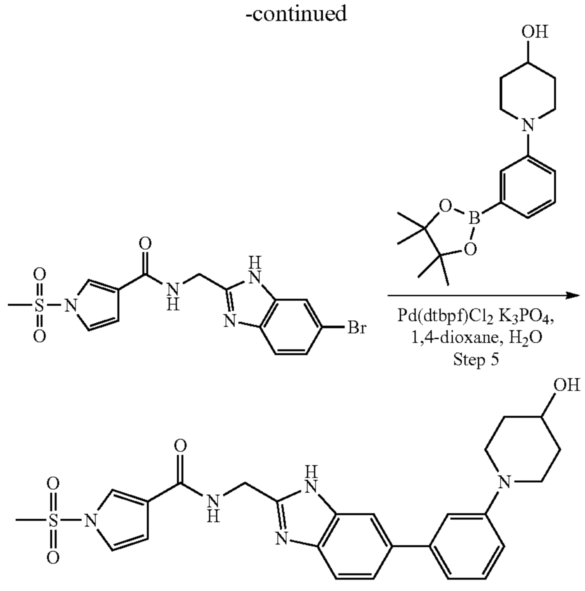

Compound 8

Step 1: Preparation of tert-butyl (2-((2-amino-5-bromophenyl)amino)-2-oxoethyl)carbamate

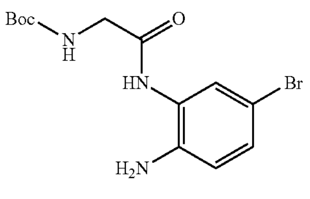 [SMILES: CC(C)(C)OC(=O)NCC(=O)Nc1cc(Br)ccc1N]

To a solution of 4-bromo-1,2-benzenediamine (2.0 g, 10.6 mmol), N-(tert-butoxycarbonyl)glycine (1.5 g, 8.8 mmol) and HATU (3.4 g, 8.8 mmol) in DMF (100 mL) was added DIPEA (3.5 mL, 35.3 mmol). After stirring overnight at room temperature, the reaction was quenched with saturated aqueous sodium bicarbonate resulting in a light brown precipitate. The precipitate was filtered off and washed with a small amount of water. The precipitate was collected and dried in vacuo, affording the title compound as a light brown powder (2.3 g, 76% yield) and used without further purification.

Step 2: Preparation of tert-butyl ((6-bromo-1H-benzo[d]imidazole-2-yl)methyl)carbamate (Intermediate 5)

Intermediate 5

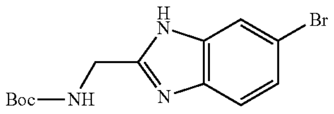

tert-Butyl (2-((2-amino-5-bromophenyl)amino)-2-oxoethyl)carbamate (2.0 g, 5.81 mmol) was dissolved in acetic acid (20 mL) and the reaction solution was heated at 60° C. After 1.5 h, the reaction was cooled to room temperature and concentrated in vacuo resulting in a dark red solid. The crude product was dissolved in ethyl acetate and washed with saturated aqueous sodium bicarbonate and brine. The organic layer was dried over sodium sulfate, filtered and concentrated in vacuo affording Intermediate 5 as a light brown powder (1.9 g, 5.82 mmol, 100%).

Step 3: Preparation of (6-bromo-1H-benzo[d]imidazol-2-yl)methanaminium chloride

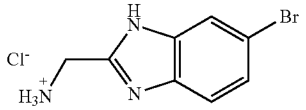

tert-Butyl ((6-bromo-1H-benzo[d]imidazole-2-yl)methyl) carbamate (1.9 g, 5.8 mmol) was suspended in a solution of 4 N HCl in 1,4-dioxane (14.5 mL, 58 mmol). After stirring overnight at room temperature, the reaction mixture was diluted with ether resulting in a white precipitate. The precipitate was filtered off and dried in vacuo affording the title compound as a white powder (1.6 g, 5.8 mmol, 100%).

Step 4: Preparation of N-((6-bromo-1H-benzo[d]imidazol-2-yl)methyl)-1-(methylsulfonyl)-1H-pyrrole-3-carboxamide

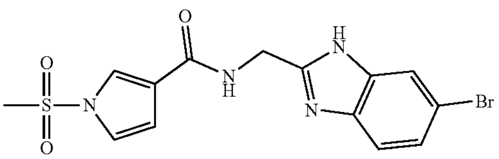 [SMILES: CS(=O)(=O)n1ccc(C(=O)NCc2nc3ccc(Br)cc3[nH]2)c1]

To a solution of 1-methylsulfonylpyrrole-3-carboxylic acid (216 mg, 1.14 mmol), EDCI (438 mg, 2.29 mmol), HOBt (309 mg, 2.29 mmol) and DIPEA (0.995 mL, 5.71 mmol) in DMF (3 mL) was added (6-bromo-1H-benzo[d]imidazol-2-yl)methanaminium chloride (300 mg, 1.14 mmol). After stirring at room temperature for 3 h, the reaction mixture was diluted with water and extracted three times with ethyl acetate; the combined organic layers were concentrated to afford a yellow oil. The oil was purified by reversed-phase HPLC to afford the title compound (280 mg, 658 μmol, 57.6% yield) as a white solid. LCMS (ESI) m/z: $[M+H]^+$=397.1. $^1$H NMR (400 MHz, DMSO-$d_6$) δ 12.45-12.37 (m, 1H), 8.95-8.93 (m, 1H), 7.86-7.85 (m, 1H), 7.73-7.61 (m, 1H), 7.51-7.40 (m, 1H), 7.32-7.25 (m, 2H), 6.80-6.79 (m, 1H), 4.62 (d, J=5.2 Hz, 2H), 3.56 (s, 3H).

Step 5: Preparation of N-((6-(3-(4-hydroxypiperidin-1-yl)phenyl)-1H-benzo[d]imidazol-2-yl)methyl)-1-(methylsulfonyl)-1H-pyrrole-3-carboxamide (Compound 8)

Compound 8

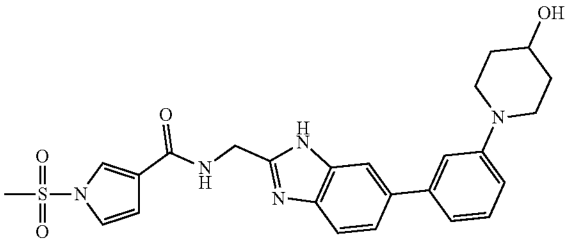

To a solution of N-((6-bromo-1H-benzo[d]imidazole-2-yl)methyl)-1-(methylsulfonyl)-1H-pyrrole-3-carboxamide (60 mg, 0.151 mmol), 1-[3-(4,4,5,5-tetramethyl-1,3,2-dioxaborolan-2-yl)phenyl]piperidin-4-ol (55.0 mg, 0.181 mmol) and $K_3PO_4$ (96.2 mg, 0.453 mmol) in 1,4-dioxane (0.4 mL) and water (0.1 mL) was added [1,1'-bis(di-tert-butylphosphino)ferrocene]dichloropalladium (9.84 mg, 0.0151 μmol) at room temperature. After stirring at 80° C. for 2 h, the reaction mixture was diluted with water and extracted three times with ethyl acetate, the combined organic layers were concentrated to afford a black brown residue. The residue was purified by reversed-phase prep-HPLC to afford Compound 8 (41.36 mg, 74.16 μmol, 49.10% yield, formic acid salt) as an off-white solid. LCMS (ESI) m/z: $[M+H]^+$=494.3. $^1$H NMR (400 MHz, DMSO-$d_6$) δ 12.26-12.19 (m, 1H), 8.93-8.90 (m, 1H), 7.87 (s, 1H), 7.75-7.61 (m, 1H), 7.57-7.47 (m, 1H), 7.42-7.41 (m, 1H), 7.32-7.23 (m, 1H), 7.27-7.23 (m, 1H), 7.13 (s, 1H), 7.02 (d, J=7.2 Hz, 1H), 6.90-6.88 (m, 1H), 6.81 (d, J=2.4 Hz, 1H), 4.65 (d, J=5.6 Hz, 2H), 3.63-3.58 (m, 3H), 3.55 (s, 3H), 2.92-2.87 (m, 2H), 1.84-1.81 (m, 2H), 1.53-1.44 (m, 2H).

Example 6. Preparation of tert-butyl ((5-bromo-3H-imidazo[4,5-b]pyridin-2-yl)methyl)carbamate (Intermediate 6)

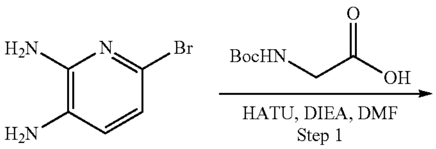

-continued

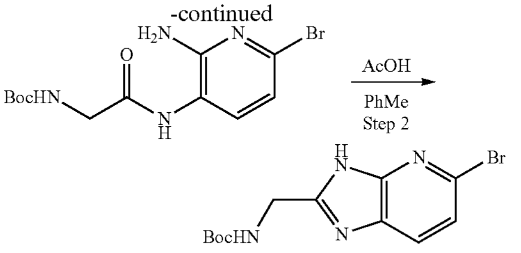

Intermediate 6

Step 1: Preparation of tert-butyl (2-((2-amino-6-bromopyridin-3-yl)amino)-2-oxoethyl)carbamate

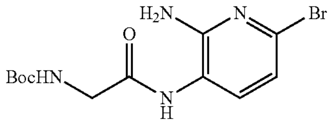 [SMILES: CC(C)(C)OC(=O)NCC(=O)Nc1ccc(Br)nc1N]

To a mixture of 2-(tert-butoxycarbonylamino)acetic acid (9.32 g, 53.2 mmol) in DMF (100 mL) was added HATU (30.3 g, 79.8 mmol), DIPEA (13.9 mL, 79.8 mmol) followed by 6-bromopyridine-2,3-diamine (10 g, 53.2 mmol). After stirring at room temperature for 2 h, the reaction mixture was added to water, and then extracted three times with ethyl acetate. The combined organic layers were washed twice with brine, filtered and concentrated under reduced pressure to give a residue. The residue was dissolved in ethyl acetate and recrystallized with petroleum ether at room temperature and washed with petroleum ether: ethyl acetate (5:1) to afford the title compound (11 g, 31.8 mmol, 59.8% yield) as a light yellow solid. LCMS (ESI) m/z: [$^{79}$BrM+H]$^+$=345.1. $^1$H NMR (400 MHz, DMSO-$d_6$) δ 9.15 (s, 1H), 7.45 (d, J=7.6 Hz, 1H), 7.07-7.03 (m, 1H), 6.69 (d, J=8.0 Hz, 1H), 6.27 (s, 2H), 3.73 (d, J=6.0 Hz, 2H), 1.38 (s, 9H).

Step 2: Preparation of tert-butyl ((5-bromo-3H-imidazo[4,5-b]pyridin-2-yl)methyl)carbamate (Intermediate 6)

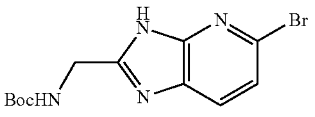

To a solution of tert-butyl (2-((2-amino-6-bromopyridin-3-yl)amino)-2-oxoethyl)carbamate (11 g, 31.9 mmol) in toluene (110 mL) was added acetic acid (40 mL). After stirring at 100° C. for 12 h, the reaction mixture was quenched by the addition of water at room temperature and extracted three times with ethyl acetate. The combined organic layers were washed twice with brine, dried over $Na_2SO_4$, filtered, and concentrated under reduced pressure to afford a residue. The residue was purified by flash silica gel chromatography (50-100% ethyl acetate/petroleum ether gradient) to afford Intermediate 5 (5 g, 15.3 mmol, 48.0% yield) as a yellow solid. LCMS (ESI) m/z: [$^{79}$BrM+H]$^+$ =327.1. $^1$H NMR (400 MHz, DMSO-$d_6$) δ 13.16-12.65 (m, 1H), 7.86 (d, J=6.0 Hz, 1H), 7.48 (s, 1H), 7.37 (d, J=8.4 Hz, 1H), 4.39 (d, J=5.2 Hz, 2H), 1.41 (s, 9H).

Example 7: Preparation of Compounds 6, 7, 9, 10, 11, 15, and 30-60

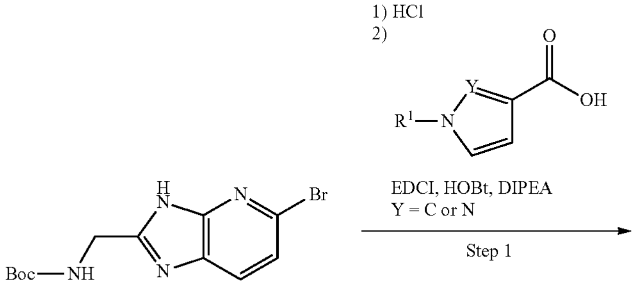

Z = CH (Intermediate 5)
Z = N (Intermediate 6)

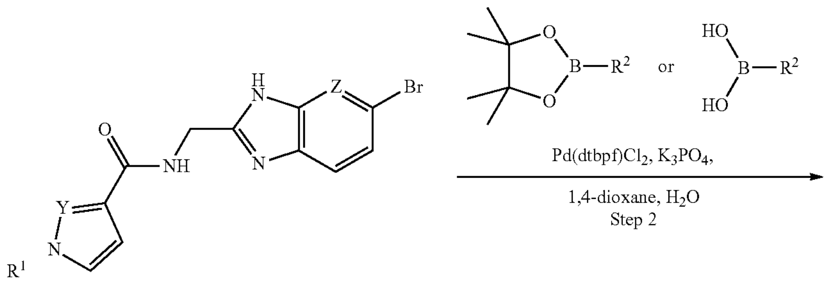

-continued

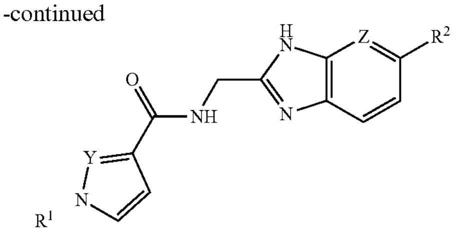

Compounds 6, 7, 9, 10, 11, 15, and 30-60, shown in Table 3 below, were synthesized starting from Intermediate 5 or 6, the corresponding carboxylic acid, and the corresponding boronic acid or ester utilizing the synthetic protocol shown the schemea above.

TABLE 3

| # | LC-MS (m/z) | $^1$H NMR |
|---|---|---|
| 6 | 403.7 | $^1$H NMR (400 MHz, DMSO-d$_6$) δ 12.17 (br s, 1H), 8.55 (br t, 1H), 7.92 (d, J = 2.4 Hz, 1H), 7.60-7.54 (m, 3H), 7.46 (d, J = 8.2 Hz, 1H), 7.40-7.33 (m, 1H), 7.02-6.97 (m, 2H), 6.67 (d, J = 2.4 Hz, 1H), 4.65, (d, J = 5.9 Hz, 2H), 3.77 (s, 3H), 1.56, (s, 9H) |
| 7 | 450.3 | $^1$H NMR (400 MHz, DMSO-d$_6$) δ 12.28-12.24 (m, 1 H), 8.93-8.90 (m, 1 H), 7.87 (s, 1 H), 7.80-7.62 (m, 1 H), 7.59-7.48 (m, 1 H), 7.41-7.39 (m, 1 H), 7.32-7.30 (m, 1 H), 7.24-7.20 (m, 1 H), 8.95 (d, J = 7.6 Hz, 1 H), 6.81 (d, J = 1.2 Hz, 1 H), 6.61 (s, 1 H), 6.38 (d, J = 8.0 Hz, 1 H), 4.64 (d, J = 5.6 Hz, 2 H), 3.86-3.83 (m, 4 H), 3.56 (s, 3 H), 2.35-2.28 (m, 2 H) |
| 9 | 451.0 | $^1$H NMR (400 MHz, DMSO-d$_6$) δ 13.27-12.10 (m, 1H), 9.05-8.80 (m, 1H), 7.99-7.83 (m, 4H), 7.64 (d, J = 8.4 Hz, 1H), 7.32 (d, J = 2.8 Hz, 1H), 6.81 (s, 1H), 6.50 (d, J = 8.8 Hz, 2H), 4.64 (s, 2H), 3.87 (d, J = 7.2 Hz, 4H), 3.57 (s, 3H), 2.37-2.31 (m, 2H) |
| 10 | 451.0 | $^1$H NMR (400 MHz, DMSO-d$_6$, 80° C.) δ 8.61-8.46 (m, 1H), 7.99-7.83 (m, 2H), 7.69 (d, J = 8.4 Hz, 1H), 7.41-7.22 (m, 3H), 7.14 (s, 1H), 6.86-6.76 (m, 1H), 6.51-6.38 (m, 1H), 4.70 (d, J = 5.6 Hz, 2H), 3.91 (d, J = 7.2 Hz, 3H), 3.87-3.74 (m, 1H), 3.49 (s, 3H), 2.42-2.30 (m, 2H) ppm |
| 11 | 508.3 | $^1$H NMR (400 MHz, DMSO-d$_6$) δ 9.21-9.19 (m, 1 H), 7.91-7.90 (m, 2 H), 7.77 (s, 2 H), 7.37-7.32 (m, 2 H), 7.21 (s, 1 H), 7.12 (d, J = 7.6 Hz, 1 H), 7.01-6.98 (m, 1H), 6.81-6.80 (m, 1 H), 4.86 (d, J = 4.8 Hz, 2 H), 3.74-3.68 (m, 4 H), 3.59 (s, 3 H), 2.33-2.27 (m, 2 H), 1.17 (d, J = 6.0 Hz, 6 H) |
| 15 | 486.2 | $^1$H NMR (400 MHz, DMSO-d$_6$) δ 8.47-8.43 (m, 1H), 7.72 (s, 1H), 7.58-7.52 (m, 2H), 7.45-7.41 (m, 1H), 7.31-7.26 (m, 1H), 7.17 (s, 1H), 7.07 (d, J = 8.0 Hz, 1H), 7.00-6.97 (m, 1H), 6.93-6.90 (m, 1H), 6.54-6.52 (m, 1H), 4.61 (d, J = 5.6 Hz, 2H), 3.75-3.66 (m, 4H), 2.34-2.27 (m, 2H), 1.49 (s, 9H), 1.17 (d, J = 6.4 Hz, 6H) |
| 30 | 432.1 | |
| 31 | 442.2 | |
| 32 | 426.2 | |
| 33 | 427.2 | |
| 34 | 424.2 | |
| 35 | 437.2 | |
| 36 | 427.2 | |
| 37 | 413.2 | |
| 38 | 424.3 | |
| 39 | 398.2 | |
| 40 | 415.2 | |
| 41 | 424.2 | |
| 42 | 430.2 | |
| 43 | 398.2 | |
| 44 | 453.2 | |
| 45 | 415.2 | |
| 46 | 459.3 | |
| 47 | 413.2 | |
| 48 | 427.2 | |
| 49 | 441.2 | |
| 50 | 444.2 | |
| 51 | 424.2 | |
| 52 | 438.2 | |
| 53 | 412.2 | |
| 54 | 439.2 | |
| 55 | 459.3 | |
| 56 | 418.2 | |
| 57 | 438.2 | |
| 58 | 417.2 | |
| 59 | 447.2 | |
| 60 | 438.1 | |

Example 8. Preparation of N-((5-(3-(4-hydroxypiperidin-1-yl)phenyl)-3H-imidazo[4,5-b]pyridin-2-yl)methyl)-1-(methylsulfonyl)-1H-pyrrole-3-carboxamide (Compound 12)

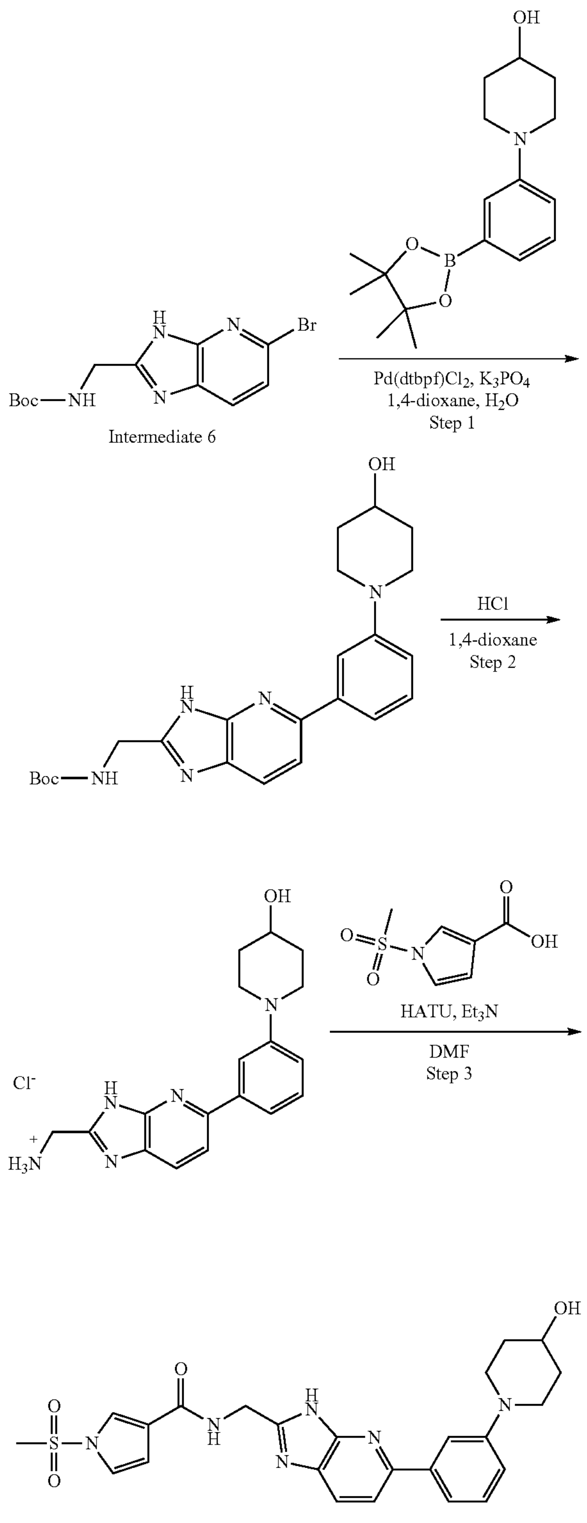

Compound 12

Step 1: Preparation of tert-butyl ((5-(3-(4-hydroxypiperidin-1-yl)phenyl)-3H-imidazo[4,5-b]pyridin-2-yl)methyl)carbamate

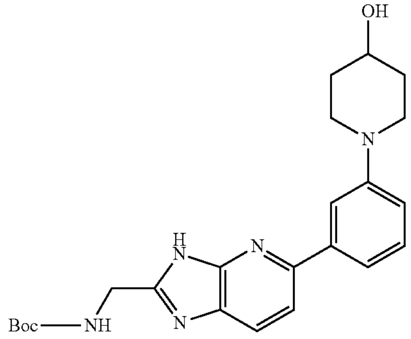 [SMILES: CC(C)(C)OC(=O)NCc1nc2ccc(-c3cccc(N4CCC(O)CC4)c3)nc2[nH]1]

To a mixture of Intermediate 6 (200 mg, 0.611 mmol) and 1-[3-(4,4,5,5-tetramethyl-1,3,2-dioxaborolan-2-yl)phenyl]piperidin-4-ol (204 mg, 0.672 mmol) in 1,4-dioxane (3 mL) and water (0.5 mL) was added $K_3PO_4$ (324 mg, 1.53 mmol) and [1,1'-bis(di-tert-butylphosphino)ferrocene]dichloropalladium (199 mg, 0.305 mmol) at 10° C. After stirring at 80° C. for 15 h, the mixture was added to water and then extracted three times with ethyl acetate; the combined organic layer was washed with brine, dried over $Na_2SO_4$, filtered and concentrated to get the crude product. The crude product was purified by reversed-phase prep-HPLC (0.1% FA condition). The solution was concentrated to afford the title compound (90 mg, 162 μmol, 26.4% yield) as a white solid. LCMS (ESI) m/z: $[M+H]^+$=424.2. $^1$H NMR (400 MHz, Methanol-$d_4$) δ 7.97-7.95 (m, 1H), 7.78-7.67 (m, 2H), 7.47-7.45 (m, 1H), 7.35-7.33 (m, 1H), 7.05-7.03 (m, 1H), 4.54 (s, 2H), 3.83-3.75 (m, 1H), 3.68-3.65 (m, 2H), 3.03-2.90 (m, 2H), 2.07-1.93 (m, 2H), 1.77-1.61 (m, 2H), 1.48 (s, 9H).

Step 2: Preparation of (5-(3-(4-hydroxypiperidin-1-yl)phenyl)-3H-imidazo[4,5-b]pyridin-2-yl)methanaminium chloride

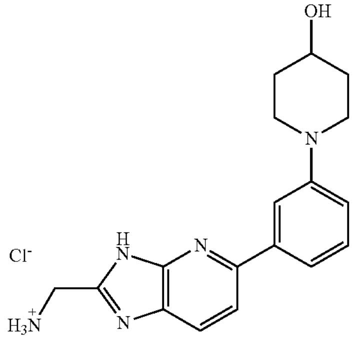 [SMILES: [Cl-] ; NCc1nc2ccc(-c3cccc(N4CCC(O)CC4)c3)nc2[nH]1]

A mixture of tert-butyl ((5-(3-(4-hydroxypiperidin-1-yl)phenyl)-3H-imidazo[4,5-b]pyridin-2-yl)methyl)carbamate (90 mg, 0.213 mmol) in a solution of 4 M HCl in 1,4-dioxane (2 mL, 8 mmol) was stirred at 15° C. After 2 h, the mixture was concentrated to afford the title compound (60 mg) as a brown solid. LCMS (ESI) m/z: $[M+H]^+$=324.1.

Step 3: Preparation of N-((5-(3-(4-hydroxypiperidin-1-yl)phenyl)-3H-imidazo[4,5-b]pyridin-2-yl)methyl)-1-(methylsulfonyl)-1H-pyrrole-3-carboxamide (Compound 12)

Compound 12

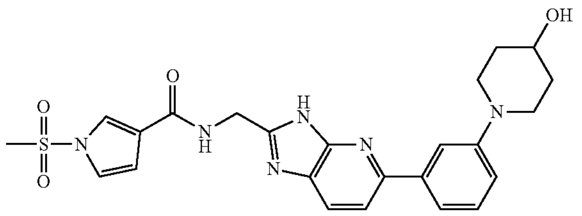

A mixture of 1-methylsulfonylpyrrole-3-carboxylic acid (35 mg, 0.185 mmol), HATU (106 mg, 0.278 mmol), and $Et_3N$ (0.0773 mL, 0.555 mmol) in DMF (1 mL) was stirred at 10° C. After 10 min, (5-(3-(4-hydroxypiperidin-1-yl)phenyl)-3H-imidazo[4,5-b]pyridin-2-yl)methanaminium chloride (60 mg) was added to the reaction mixture. After stirring at at 15° C. for 2 h, the mixture was filtered off and the filtrate was purified by reversed-phase prep-HPLC (water:ACN:FA) to afford Compound 12 (22.1 mg, 40.8 μmol, 22.1% yield, formic acid salt) as a white solid. LCMS (ESI) m/z: $[M+H]^+$=495.2 $^1$H NMR (400 MHz, DMSO-$d_6$) δ 8.91 (br s, 1H), 7.94 (d, J=8.0 Hz, 1H), 7.87-7.86 (m, 1H), 7.76 (d, J=8.4 Hz, 1H), 7.66 (s, 1H), 7.44 (d, J=6.8 Hz, 1H), 7.34-7.24 (m, 2H), 6.98 (d, J=7.2 Hz, 1H), 6.80-6.79 (m, 1H), 4.66 (d, J=5.6 Hz, 2H), 3.68-3.53 (m, 6H), 2.94-2.89 (m, 2H), 1.86-1.83 (m, 2H), 1.58-1.43 (m, 2H).

Example 9. Preparation of Compounds 13, 14, and 16

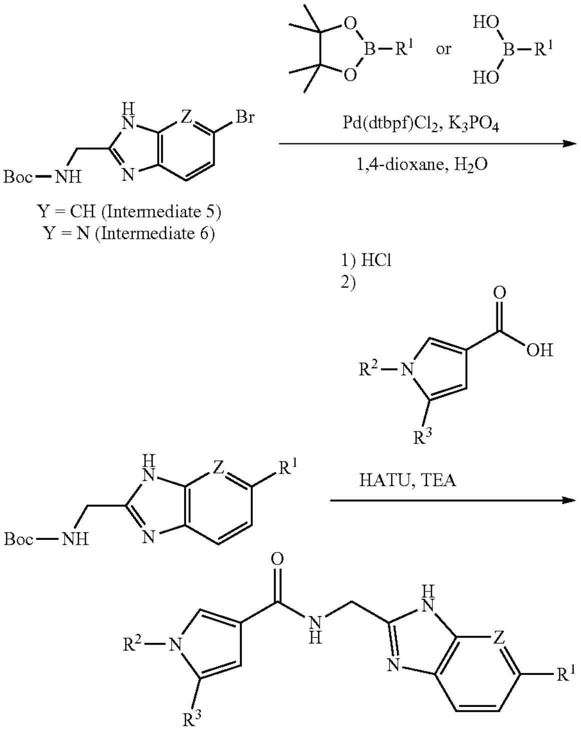

Compounds 13, 14, and 16 to 19, shown in Table 4 below, were synthesized starting from Intermediate 5 or 6, the appropriate boronic ester, and the corresponding carboxylic acid utilizing the synthetic protocol shown in the scheme above.

TABLE 4

| # | LC-MS (m/z) | $^1$H NMR |
|---|---|---|
| 13 | 509.2 | 1H NMR (400 MHz, DMSO-$d_6$) δ 8.95 (s, 1H), 8.00 (d, J = 8.4 Hz, 1H), 7.89-7.88 (m, 1H), 7.83 (d, J = 8.4 Hz, 1H), 7.65 (s, 1H),7.50 (d, J = 7.6 Hz, 1H), 7.38-7.29 (m, 2H), 7.02 (d, J = 8.0 Hz, 1H), 6.81-6.80 (m, 1H), 4.69 (d, J = 5.6 Hz, 2H), 3.77-3.71 (m, 2H), 3.69-3.66 (m, 2H), 3.57 (s, 3H), 2.35-2.30 (m, 2H), 1.19-1.18 (m, 6H) |
| 14 | 509.3 | $^1$H NMR (400 MHz, DMSO-$d_6$) δ 12.96 (br s, 1H), 8.91 (s, 1H), 7.97 (d, J = 8.8 Hz, 2H), 7.89-7.88 (m, 2H), 7.69 (d, J = 8.4 Hz, 1H), 7.38-7.29 (m, 1H), 7.04 (d, J = 8.8 Hz, 2H), 6.82-6.81 (m, 1H), 4.65 (d, J = 5.6 Hz, 2H), 3.75-3.65 (m, 4H), 3.60-3.56 (m, 3H), 2.31-2.29 (m, 2H), 1.18 (d, J = 6.0 Hz, 6H) |
| 16 | 403.2 | $^1$H NMR (400 MHz, DMSO-$d_6$) δ 12.19 (s, 1H), 8.47-8.43 (m, 1H), 7.81-7.65 (m, 1H), 7.60-7.43 (m, 3H), 7.39-7.34 (m, 1H), 7.25-7.18 (m, 2H), 6.99-6.97 (m, 1H), 6.92-6.89 (m, 1H), 6.54-6.52 (m, 1H), 4.62 (d, J = 6.0 Hz, 2H), 3.83 (s, 3H), 1.49 (s, 9H) |
| 17 | 439.1 | $^1$H NMR (400 MHz, DMSO-$d_6$) δ 12.36-12.23 (m, 1H), 8.86-8.85 (m, 1H), 7.77-7.73 (m, 2H), 7.56 (d, J = 7.2 Hz, 1H), 7.46-7.43 (m, 1H), 7.38-7.34 (m, 1H), 7.23-7.17 (m, 2H), 6.91-6.88 (m, 1H), 6.52 (s, 1H), 4.62 (d, J = 5.6 Hz, 2H), 3.82 (s, 3H), 3.52 (s, 3H), 2.40 (s, 3H) |
| 18 | 496.2 | $^1$H NMR (400 MHz, methanol-$d_4$) δ 7.96 (d, J = 8.4 Hz, 1H), 7.76 (d, J = 8.4 Hz, 1H), 7.68 (s, 1H), 7.59-7.58 (m, 1H), 7.48 (d, J = 7.6 Hz, 1H), 7.35-7.34 (m, 1H), 7.05-6.98 (m, 2H), 6.65-6.64 (m, 1H), 4.81 (s, 2H), 3.88-3.78 (m, 2H), 3.63 (d, J = 10.8 Hz, 2H), 2.42-2.37 (m, 2H), 1.82-1.72 (m, 4H), 1.25 (d, J = 6.0 Hz, 6H) |
| 19 | 487.2 | $^1$H NMR (400 MHz, methanol-$d_4$) δ 7.96 (d, J = 8.4 Hz, 1H), 7.74 (d, J = 8.4 Hz, 1H), 7.68 (d, J = 1.6 Hz, 1H), 7.60-7.59 (m, 1H), 7.47 (d, J = 8.0 Hz, 1H), 7.35-7.34 (m, 1H), 7.02-7.01 (m, 1H), 6.95-6.93 (m, 1H), 6.59-6.58 (m, 1H), 4.80 (s, 2H), 3.89-3.77 (m, 2H), 3.63 (d, J = 10.8 Hz, 2H), 2.44-2.35 (m, 2H), 1.55 (s, 9H), 1.25 (d, J = 6.4 Hz, 6H) |

Example 10. Preparation of N-((6-(2-methyl-1-oxo-1,2-dihydroisoquinolin-7-yl)-1H-benzo[d]imidazol-2-yl)methyl)-1-(3-methyloxetan-3-yl)-1H-pyrrole-3-carboxamide (Compound 20)

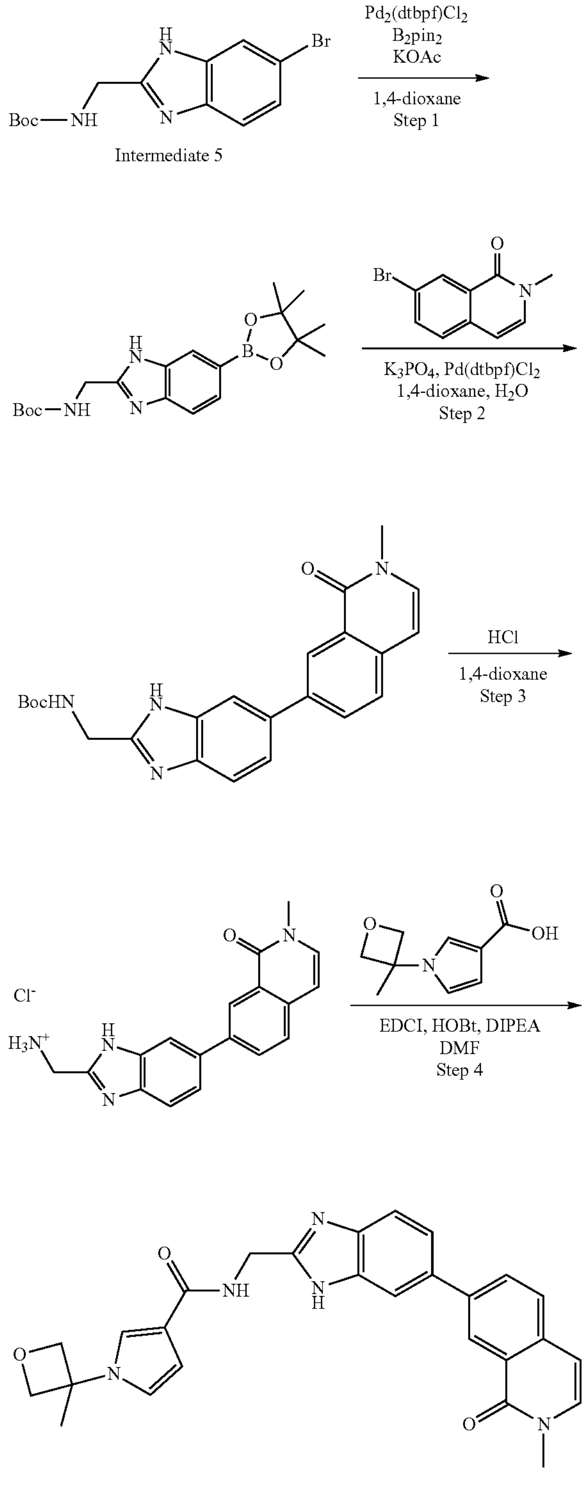

Compound 20

Step 1: Preparation of tert-butyl N-[[5-(4,4,5,5-tetramethyl-1,3,2-dioxaborolan-2-yl)-1H-benzimidazol-2-yl]methyl]carbamate

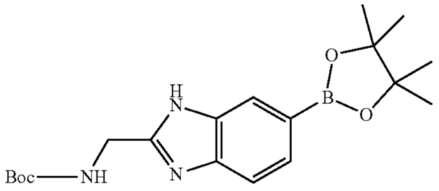 [SMILES: CC(C)(C)OC(=O)NCc1nc2ccc(B3OC(C)(C)C(C)(C)O3)cc2[nH]1]

To a mixture of tert-butyl ((6-bromo-1H-benzo[d]imidazol-2-yl)methyl)carbamate (5 g, 15.33 mmol), 4,4,5,5-tetramethyl-2-(4,4,5,5-tetramethyl-1,3,2-dioxaborolan-2-yl)-1,3,2-dioxaborolane (9.73 g, 38.3 mmol) in 1,2-dimethoxyethane (100 mL) was added $Pd(dppf)Cl_2$ (2.80 g, 3.83 mmol) and KOAc (4.51 g, 46.0 mmol) at room temperature and the mixture was stirred at 100° C. After 15 h, the mixture was added to water and then extracted three times with ethyl acetate. The combined organic layer was washed with brine, dried over $Na_2SO_4$, filtered, and concentrated to afford the crude product. The residue was purified by silica gel column chromatography (petroleum ether/ethyl acetate=5/1 to 1/1) to afford the title compound (5.5 g, 11.2 mmol, 73.1% yield) as a yellow solid. LCMS (ESI) m/z: $[M+H]^+=374.1$.

Step 2: Preparation of tert-butyl ((6-(2-methyl-1-oxo-1,2-dihydroisoquinolin-7-yl)-1H-benzo[d]imidazol-2-yl)methyl)carbamate

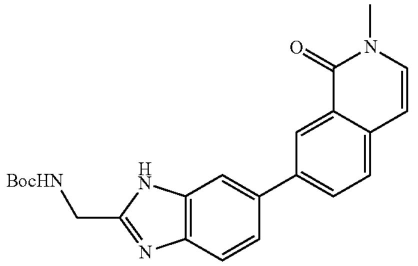 [SMILES: Cn1ccc2ccc(-c3ccc4nc(CNC(=O)OC(C)(C)C)[nH]c4c3)cc2c1=O]

A mixture of 7-bromo-2-methyl-1(2H)-isoquinolinone (1 g, 4.20 mmol), tert-butyl ((6-(2-methyl-1-oxo-1,2-dihydroisoquinolin-7-yl)-1H-benzo[d]imidazol-2-yl)methyl)carbamate (1.57 g, 4.20 mmol), $K_3PO_4$ (2.67 g, 12.6 mmol) and [1,1'-bis(di-tert-butylphosphino)ferrocene]dichloropalladium (274 mg, 0.420 mmol) in 1,4-dioxane (10 mL) and water (4 mL) was stirred at 80° C. under a $N_2$ atmosphere. After 12 h, the reaction mixture was poured into water and extracted three times with ethyl acetate. The combined organic layers were dried over anhydrous $Na_2SO_4$, filtered and concentrated under reduced pressure to give a residue. The residue was purified by flash silica gel chromatography (0-44% methanol/ethyl acetate) to afford the title compound (800 mg, 1.98 mmol, 47.1% yield) as a yellow solid. LCMS (ESI) m/z: $[M+H]^+=405.1$. $^1H$ NMR (400 MHz, DMSO-$d_6$) δ 12.25 (d, J=6.4 Hz, 1H), 8.42 (s, 1H), 8.03-7.99 (m, 1H), 7.84-7.69 (m, 2H), 7.63-7.47 (m, 2H), 7.46-7.43 (m, 2H), 6.64-6.61 (m, 1H), 4.35 (d, J=6.0 Hz, 2H), 3.50 (s, 3H), 1.39 (s, 9H).

Step 3: Preparation of (6-(2-methyl-1-oxo-1,2-dihydroisoquinolin-7-yl)-1H-benzo[d]imidazol-2-yl) methanaminium chloride

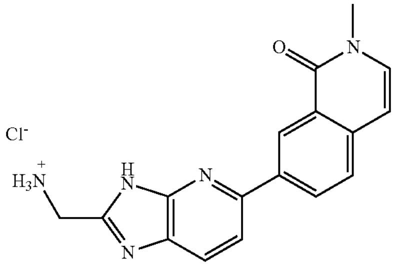 [SMILES: [Cl-] ; Cn1ccc2ccc(-c3ccc4nc(CN)[nH]c4n3)cc2c1=O]

and methanol. The solution was purified by reversed-phase prep-HPLC (water:ACN:$NH_4OH$) to afford Compound 20 (23.2 mg, 0.0497 mmol, 33.9% yield) as a colorless oil. LCMS (ESI) m/z: $[M+H]^+$=468.0. $^1H$ NMR (400 MHz, DMSO-$d_6$) δ 12.27 (s, 1H), 8.58-8.55 (m, 1H), 8.46 (d, J=2.0 Hz, 1H), 8.07-8.02 (m, 1H), 7.89-7.73 (m, 2H), 7.65-7.52 (m, 3H), 7.50-7.47 (m, 1H), 7.04-7.02 (m, 1H), 6.66 (d, J=7.2 Hz, 1H), 6.63-6.61 (m, 1H), 4.84 (d, J=6.4 Hz, 2H), 4.66-4.62 (m, 4H), 3.54 (s, 3H), 1.79 (s, 3H).

Example 11. Preparation of Compound 24

Compound 24, shown in Table 5 below, was synthesized starting from the appropriate common intermediate (6-(2-methyl-1-oxo-1,2-dihydroisoquinolin-7-yl)-1H-benzo[d]imidazol-2-yl)methanaminium chloride and 1-(isopropylsulfonyl)-1H-pyrrole-3-carboxylic acid utilizing the synthetic protocol described in Example 10 above.

TABLE 5

| # | LC-MS (m/z) | $^1H$ NMR |
|---|---|---|
| 24 | 504.0 | $^1H$ NMR (400 MHz, DMSO-$d_6$) δ 12.41-12.32 (m, 1H), 8.99-8.96 (m, 1H), 8.45 (d, J = 2.0 Hz, 1H), 8.16 (s, 1H), 8.06-8.03 (m, 1H), 7.86-7.73 (m, 3H), 7.63-7.60 (m, 1H), 7.58-7.53 (m, 1H), 7.48 (d, J = 7.2 Hz, 1H), 7.29-7.28 (m, 1H), 6.84-6.83 (m, 1H), 6.65 (d, J = 7.2 Hz, 1H), 4.67 (d, J = 6.0 Hz, 2H), 3.90-3.83 (m, 1H), 3.54 (s, 3H), 1.24-1.21 (m, 6H) |

To a mixture of tert-butyl ((6-(2-methyl-1-oxo-1,2-dihydroisoquinolin-7-yl)-1H-benzo[d]imidazol-2-yl)methyl)carbamate (800 mg, 1.98 mmol) in 1,4-dioxane (8 mL) was added a solution of 4 M HCl in 1,4-dioxane (8 mL, 32 mmol). After stirring at room temperature for 12 h, the reaction mixture was concentrated under reduced pressure to give a residue. The residue was poured into dimethyl sulfoxide, stirred for 30 min and filtered to afford the title compound (450 mg, 1.32 mmol, 66.8% yield) as a yellow solid. LCMS (ESI) m/z: $[M+H]^+$=305.1.

Step 4: Preparation of N-((6-(2-methyl-1-oxo-1,2-dihydroisoquinolin-7-yl)-1H-benzo[d]imidazol-2-yl) methyl)-1-(3-methyloxetan-3-yl)-1H-pyrrole-3-carboxamide (Compound 20)

Compound 20

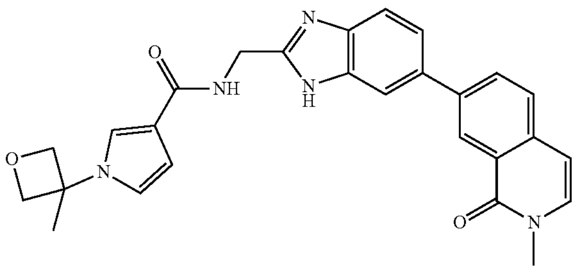

A mixture of (6-(2-methyl-1-oxo-1,2-dihydroisoquinolin-7-yl)-1H-benzo[d]imidazol-2-yl)methanaminium chloride (50 mg, 0.147 mmol), 1-(3-methyloxetan-3-yl)pyrrole-3-carboxylic acid (26.6 mg, 0.147 mmol), HOBt (29.7 mg, 0.220 mmol), EDCI (42.2 mg, 0.220 mmol) and DIPEA (0.128 mL, 0.734 mmol) in DMF (1 mL) was stirred at room temperature. After 12 h, the mixture was poured into water Example 12: Preparation of (S)-methyl 3-(2-((1-(methylsulfonyl)-1H-pyrrole-3-carboxamido) methyl)-1H-benzo[d]imidazol-6-yl)piperidine-1-carboxylate (Compound 21) and (R)-methyl 3-(2-((1-(methylsulfonyl)-1H-pyrrole-3-carboxamido) methyl)-1H-benzo[d]imidazol-6-yl)piperidine-1-carboxylate (Compound 22)

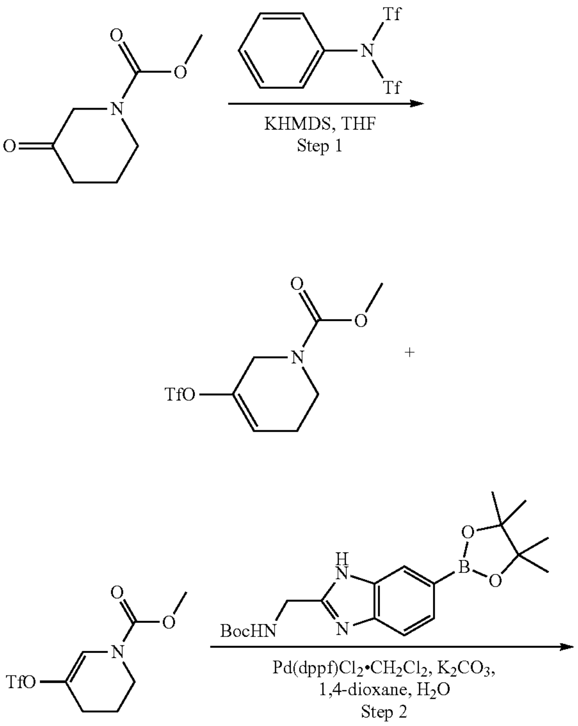

-continued

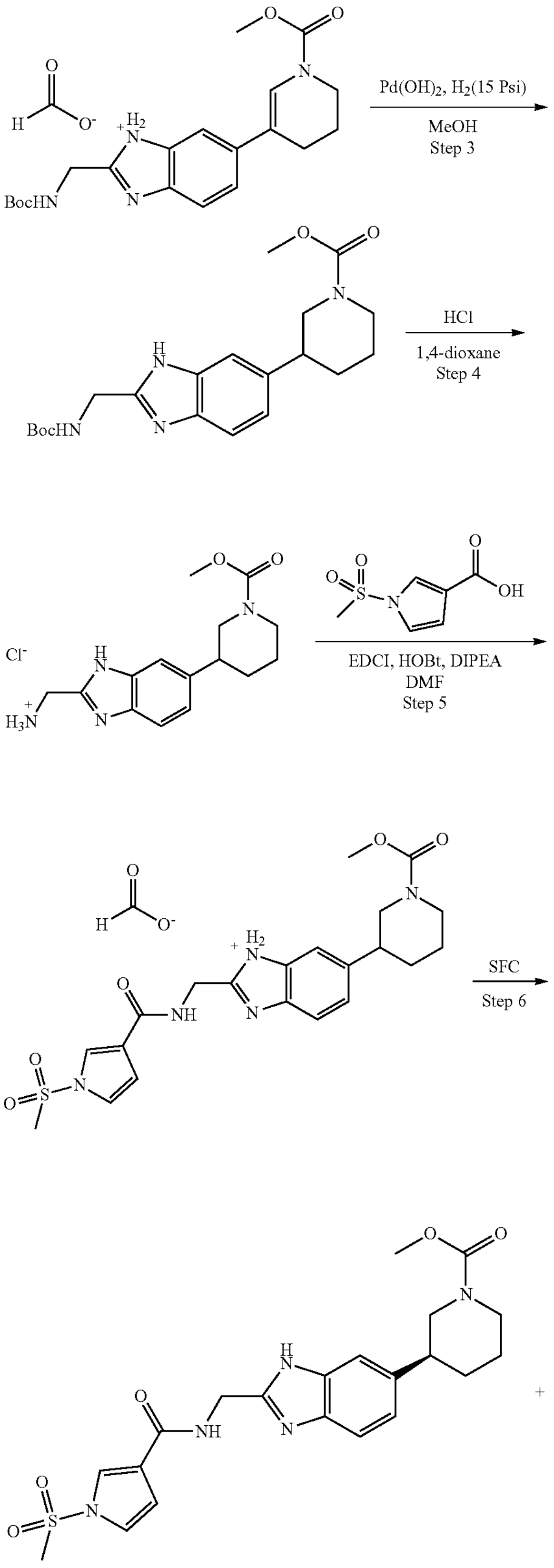

Compound 21

-continued

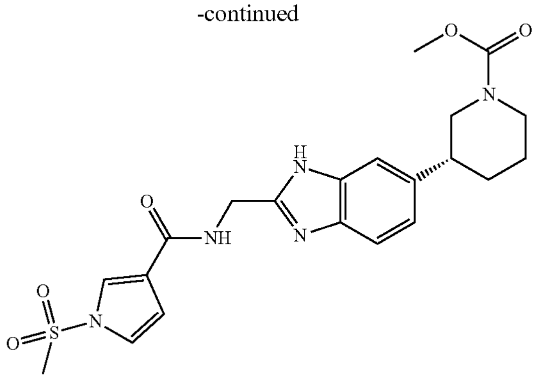

Compound 22

Step 1: methyl 5-(((trifluoromethyl)sulfonyl)oxy)-3,6-dihydropyridine-1(2H)-carboxylate and methyl 5-(((trifluoromethyl)sulfonyl)oxy-3,4-dihydropyridine-1(2H)-carboxylate

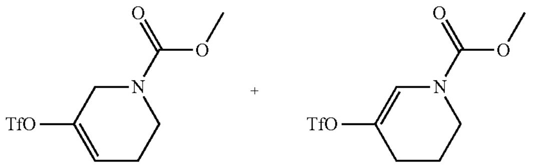 [SMILES: COC(=O)N1CCC=C(OS(=O)(=O)C(F)(F)F)C1 ; COC(=O)N1C=C(OS(=O)(=O)C(F)(F)F)CCC1]

To a cooled solution (−78° C.) of 1 M KHMDS (350 mL, 350 mmol) in THE (400 mL) was added a solution of methyl 3-oxopiperidine-1-carboxylate (44 g, 280 mmol) dissolved in THF (400 mL) dropwise. After stirring at −78° C. for 0.5 h, a solution of 1,1,1-trifluoro-N-phenyl-N-(trifluoromethylsulfonyl)-methanesulfonamide (125 g, 350 mmol) dissolved in THE (500 mL) was added drop wise to the reaction mixture and the mixture was warmed to room temperature. After 2 h, the mixture was washed with water and extracted three times with dichloromethane. The combined organic phase was washed three times with brine, dried over anhydrous $Na_2SO_4$, filtered and concentrated under reduced pressure to give a residue. The residue was purified by silica gel column chromatography (petroleum ether/ethyl acetate=20/1 to 10/1) to afford a mixture of title compounds (80.4 g, 144 mmol, 51.6% yield, 52% purity) as a yellow oil. LCMS (ESI) m/z: $[M+H]^+$=290.0.

Step 2: Preparation of 2-(((tert-butoxycarbonyl)amino)methyl)-6-(1-(methoxycarbonyl)-1,4,5,6-tetrahydropyridin-3-yl)-1H-benzo[d]imidazol-1-ium formate

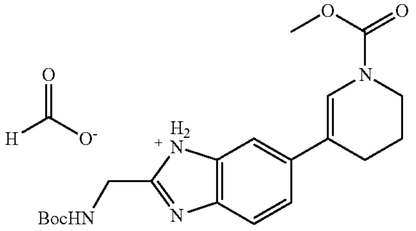

A mixture of methyl 5-(((trifluoromethyl)sulfonyl)oxy)-3,6-dihydropyridine-1(2H)-carboxylate and methyl 5-(((trifluoromethyl)sulfonyl)oxy)-3,4-dihydropyridine-1(2H)-carboxylate (1.12 g, 2.01 mmol), tert-butyl N-[[5-(4,4,5,5-tetramethyl-1,3,2-dioxaborolan-2-yl)-1H-benzimidazol-2-yl]methyl]carbamate (500 mg, 1.34 mmol), $K_2CO_3$ (555 mg, 4.02 mmol) and bis(diphenylphosphino)ferrocene palladium dichloromethane (109 mg, 0.134 mmol) in 1,4-dioxane (10 mL) and water (2 mL) was degassed and purged with $N_2$ for 3 times, and then the mixture was stirred at 80° C. under a $N_2$ atmosphere. After for 12 h, the reaction mixture was poured into water and extracted three times with ethyl acetate. The combined organic layers dried over anhydrous $Na_2SO_4$, filtered and concentrated under reduced pressure to give a residue. The residue was purified by flash silica gel chromatography (0-20% methanol/dichloromethane). The crude product was further purified by reversed phase chromatography and concentrated under reduced pressure to remove acetonitrile. The solution was extracted three times with ethyl acetate and the combined organic layers were dried over anhydrous $Na_2SO_4$, filtered and concentrated under reduced pressure to afford the title compound (150 mg, 0.347 mmol, 25.9% yield) as a black brown oil. LCMS (ESI) m/z: $[M+H]^+$=387.1. $^1$H NMR (400 MHz, DMSO-$d_6$) δ 12.91-12.48 (m, 1H), 8.13 (s, 1H), 7.49-7.42 (m, 3H), 7.30-7.21 (m, 1H), 6.25 (s, 1H), 4.37-4.30 (m, 4H), 3.65 (s, 3H), 3.55-3.51 (m, 2H), 2.29 (d, J=3.6 Hz, 2H), 1.42 (s, 9H).

Step 3: Preparation of 2-(((tert-butoxycarbonyl)amino)methyl)-6-(1-(methoxycarbonyl)-piperidin-3-yl)-1H-benzo[d]imidazol-1-ium formate

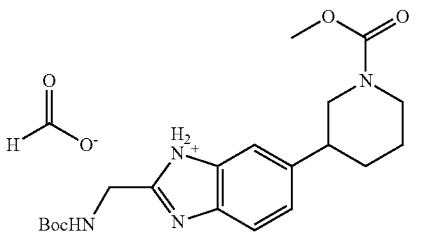

To a solution of 2-(((tert-butoxycarbonyl)amino)methyl)-6-(1-(methoxycarbonyl)-1,4,5,6-tetrahydropyridin-3-yl)-1H-benzo[d]imidazol-1-ium formate (130 mg, 0.301 mmol) in methanol (0.5 mL) was added 50% $Pd(OH)_2$ (50 mg, 0.178 mmol) under $N_2$. The suspension was degassed under vacuum and purged with $H_2$ several times and stirred under $H_2$ (15 psi) at room temperature. After 16 h, the mixture combined with another batch was filtered with celatom and washed three times with methanol and ethyl acetate. The filtrate was concentrated under reduced pressure to afford the title compound (130 mg) as a brown solid. LCMS (ESI) m/z: $[M+H]^+$=389.1. $^1$H NMR (400 MHz, DMSO-$d_6$) δ 12.66-12.61 (m, 1H), 8.13 (s, 1H), 7.52-7.38 (m, 2H), 7.36 (s, 1H), 7.18-7.04 (m, 1H), 4.33 (d, J=6.0 Hz, 2H), 4.10-3.71 (m, 3H), 3.67-3.56 (m, 4H), 2.71-2.66 (m, 1H), 1.92 (d, J=10.8 Hz, 1H), 1.76-1.68 (m, 2H), 1.56-1.46 (m, 1H), 1.44-1.39 (m, 9H).

Step 4: Preparation of (6-(1-(methoxycarbonyl)piperidin-3-yl)-1H-benzo[d]imidazol-2-yl)-methanaminium chloride

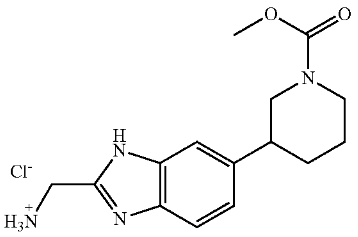 [SMILES: [Cl-] ; COC(=O)N1CCCC(c2ccc3nc(CN)[nH]c3c2)C1]

A mixture of 2-(((tert-butoxycarbonyl)amino)methyl)-6-(1-(methoxycarbonyl)piperidin-3-yl)-1H-benzo[d]imidazol-1-ium formate (110 mg, 0.253 mmol) in a solution of 4 M HCl in 1,4-dioxane (2 mL, 8 mmol) was stirred at room temperature. After 0.5 h, the reaction mixture concentrated under reduced pressure to afford the title compound (110 mg) as a yellow solid which was used in the next step directly. LCMS (ESI) m/z: $[M+H]^+$=289.1.

Step 5: Preparation of 6-(1-(methoxycarbonyl)piperidin-3-yl)-2-((1-(methylsulfonyl)-1H-pyrrole-3-carboxamido)methyl)-1H-benzo[d]imidazol-1-ium formate

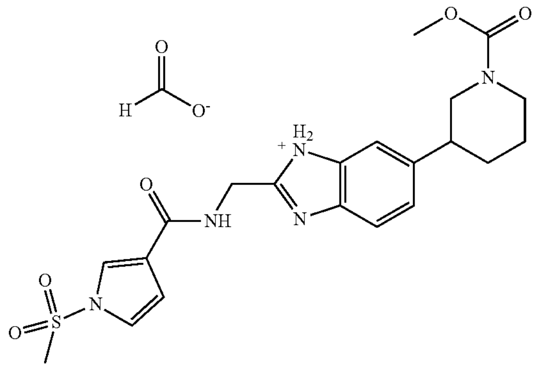

A mixture of (6-(1-(methoxycarbonyl)piperidin-3-yl)-1H-benzo[d]imidazol-2-yl)-methanaminium chloride (110 mg, 0.339 mmol), 1-methylsulfonylpyrrole-3-carboxylic acid (70.5 mg, 0.373 mmol), EDCI (130 mg, 0.677 mmol), HOBt (91.5 mg, 0.677 mmol) and DIPEA (177 µL, 1.02 mmol) in DMF (2 mL) was stirred at room temperature. After 2 h, the reaction mixture was partitioned between ethyl acetate and water. The organic phase was separated, washed three times with brine, dried over $Na_2SO_4$, filtered and concentrated under reduced pressure to give a residue. The residue was purified by reversed-phase prep-HPLC (water:ACN:FA) to afford the title compound (37.4 mg, 74.0 µmol, 21.9% yield, formic acid salt) as a white solid. LCMS (ESI) m/z: $[M+H]^+$=459.9. $^1$H NMR (400 MHz, methanol-$d_4$) δ 8.26-8.16 (m, 1H), 7.88-7.82 (m, 1H), 7.48 (d, J=8.0 Hz, 1H), 7.42 (s, 1H), 7.27-7.26 (m, 1H), 7.16 (d, J=8.0 Hz, 1H), 6.82-6.81 (m, 1H), 4.77 (s, 2H), 4.25-4.10 (m, 2H), 3.70 (s, 3H), 3.37 (s, 3H), 3.00-2.82 (m, 2H), 2.77 (s, 1H), 2.09-1.99 (m, 1H), 1.88-1.72 (m, 2H), 1.61 (d, J=12.0 Hz, 1H).

Step 6: Preparation of (S)-methyl 3-(2-((1-(methylsulfonyl)-1H-pyrrole-3-carboxamido)methyl)-1H-benzo[d]imidazol-6-yl)piperidine-1-carboxylate (Compound 21) and (R)-methyl 3-(2-((1-(methylsulfonyl)-1H-pyrrole-3-carboxamido)methyl)-1H-benzo[d]imidazol-6-yl)piperidine-1-carboxylate (Compound 22)

Compound 21

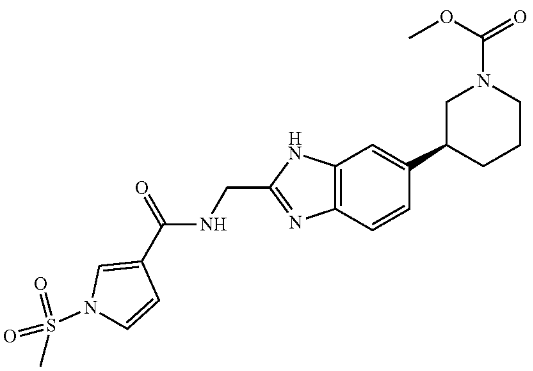

+

Compound 22

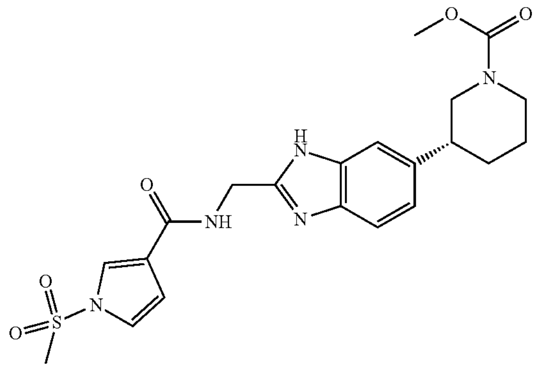

6-(1-(methoxycarbonyl)piperidin-3-yl)-2-((1-(methylsulfonyl)-1H-pyrrole-3-carboxamido)methyl)-1H-benzo[d]imidazol-1-ium formate (37.4 mg, 0.0740 mmol) was subjected to chiral SFC to afford Compound 21 (10.2 mg, 0.0220 mmol) as an off-white solid and Compound 22 (10.5 mg, 0.0228 mmol) as an off-white solid. Compound 21: LCMS (ESI) m/z: $[M+H]^+$=460.4; $^1$H NMR (400 MHz, methanol-$d_4$) δ 7.85-7.84 (m, 1H), 7.57-7.34 (m, 2H), 7.27-7.26 (m, 1H), 7.15 (d, J=8.0 Hz, 1H), 6.83-6.82 (m, 1H), 4.76 (s, 2H), 4.26-4.09 (m, 2H), 3.70 (s, 3H), 3.37 (s, 3H), 2.98-2.83 (m, 2H), 2.82-2.71 (m, 1H), 2.09-1.99 (m, 1H), 1.87-1.74 (m, 2H), 1.68-1.53 (m, 1H). Compound 22: LCMS (ESI) m/z: $[M+H]^+$=460.4; $^1$H NMR (400 MHz, methanol-$d_4$) δ 7.86-7.85 (m, 1H), 7.56-7.32 (m, 2H), 7.27-7.26 (m, 1H), 7.16 (d, J=8.0 Hz, 1H), 6.83-6.82 (m, 1H), 4.77 (s, 2H), 4.19-4.15 (m, 2H), 3.70 (s, 3H), 3.37 (s, 3H), 2.99-2.82 (m, 2H), 2.81-2.72 (m, 1H), 2.09-2.00 (m, 1H), 1.88-1.75 (m, 2H), 1.68-1.56 (m, 1H).

Example 13. Preparation of methyl 3-(2-(((tert-butoxycarbonyl)amino)methyl)-3H-imidazo[4,5-b]pyridin-5-yl)-5,6-dihydropyridine-1(2H)-carboxylate

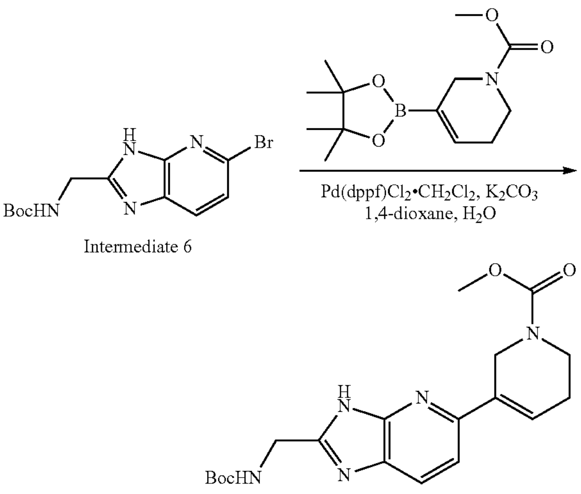

A mixture of Intermediate 6 (500 mg, 1.53 mmol), methyl 5-(4,4,5,5-tetramethyl-1,3,2-dioxaborolan-2-yl)-3,4-dihydro-2H-pyridine-1-carboxylate (449 mg, 1.68 mmol), dichloro 1,1'-bis(diphenylphosphino)ferrocene palladium dichloromethane (125 mg, 0.153 mmol), and $K_2CO_3$ (634 mg, 4.58 mmol) in 1,4-dioxane (5 mL) and water (1 mL) was degassed and purged with $N_2$ three times, and then stirred at 80° C. for under a $N_2$ atmosphere. After 12 h, the reaction mixture was diluted with water and extracted three times with ethyl acetate. The combined organic layers were washed with brine, dried over $Na_2SO_4$, filtered and concentrated under reduced pressure to give a residue. The residue was purified by flash silica gel chromatography (0-100% ethyl acetate/petroleum ether) to afford the title compound (140 mg, 0.361 mmol, 23.7% yield) as a colorless oil. LCMS (ESI) m/z: $[M+H]^+$=388.3. $^1$H NMR (400 MHz, DMSO-$d_6$) δ 13.18-12.05 (m, 1H), 7.96-7.76 (m, 1H), 7.53 (d, J=8.4 Hz, 2H), 6.79-6.64 (m, 1H), 4.46 (s, 2H), 4.46-4.34 (m, 2H), 3.70-3.62 (m, 3H), 3.54 (d, J=5.6 Hz, 2H), 2.39-2.30 (m, 2H), 1.42 (d, J=4.0 Hz, 9H).

Example 14. Preparation of Compounds 25 and 26

Compounds 25 and 26, shown in Table 6, below were synthesized starting from intermediate 6 and the corresponding cyclohexenes utilizing the synthetic protocol described in Example 12 above.

TABLE 6

| # | LC-MS (m/z) | $^1$H NMR |
|---|---|---|
| 25 | 461.1 | $^1$H NMR (400 MHz, methanol-$d_4$) δ 7.87 (d, J = 2.0 Hz, 2H), 7.30-7.28 (m, 1H), 7.22 (d, J = 8.0 Hz, 1H), 6.84-6.83 (m, 1H), 4.81 (s, 2H), 4.35-4.07 (m, 2H), 3.71 (s, 3H), 3.39 (s, 3H), 3.25-3.05 (m, 1H), 2.98-2.92 (m, 2H), 2.18-2.03 (m, 1H), 1.98-1.74 (m, 2H), 1.65-1.61 (m, 1H) |
| 26 | 461.1 | $^1$H NMR (400 MHz, methanol-$d_4$) δ 7.85 (s, 2H), 7.27 (s, 1H), 7.21 (d, J = 8.0 Hz, 1H), 6.82 (s, 1H), 4.81 (s, 2H), 4.36-4.04 (m, 2H), 3.71 (s, 3H), 3.39 (s, 3H), 3.19-3.02 (m, 1H), 2.99-2.79 (m, 2H), 2.15-1.99 (m, 1H), 1.96-1.74 (m, 2H), 1.71-1.52 (m, 1H) |

Example 15. Preparation of 1-(methylsulfonyl)-N-((5-phenyl-3H-imidazo[4,5-b]pyridin-2-yl)methyl)-1H-pyrrole-3-carboxamide (Compound 74)

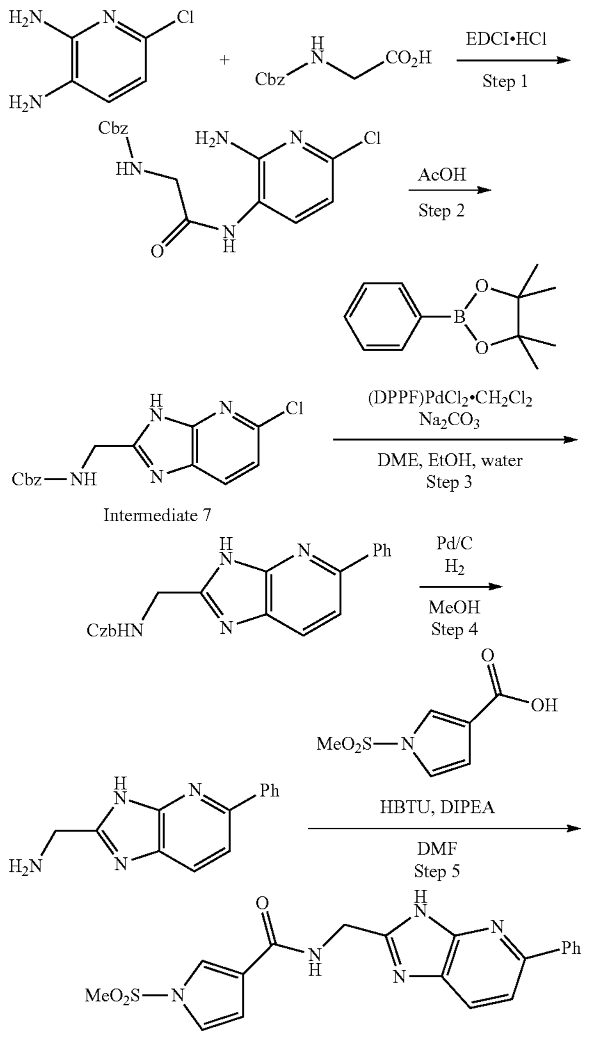

Compound 74

Step 1: Preparation of benzyl (2-((2-amino-6-chloropyridin-3-yl)amino)-2-oxoethyl)carbamate

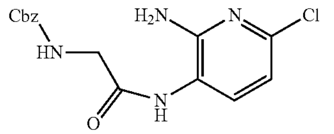 [SMILES: Nc1nc(Cl)ccc1NC(=O)CNC(=O)OCc1ccccc1]

To a solution of 6-chloropyridine-2,3-diamine (2.0 g, 13.9 mmol) and ((benzyloxy)carbonyl)glycine (2.9 g, 13.9 mmol) in pyridine (46.3 mL) was added N-(3-dimethylaminopropyl)-N'-ethylcarbodiimide hydrochloride (7.99 g, 41.7 mmol). After stirring at room temperature overnight, the reaction mixture was diluted with water and ethyl acetate. The organic layer was washed twice with water and brine and dried with anhydrous sodium sulfate. Salts were removed via vacuum filtration and volatile material were removed using a rotary evaporator. The residue was triturated with dichloromethane to afford the title compound (3.49 g, 10.4 mmol, 75% yield). LCMS (ESI) m/z: $[M+H]^+=334.6$.

Step 2: Preparation of benzyl ((5-chloro-3H-imidazo[4,5-b]pyridin-2-yl)methyl)carbamate (Intermediate 7)

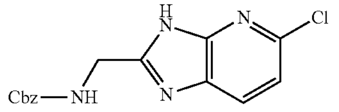 [SMILES: O=C(NCc1nc2ccc(Cl)nc2[nH]1)OCc1ccccc1]

A suspension of benzyl (2-((2-amino-6-chloropyridin-3-yl)amino)-2-oxoethyl)carbamate (2.53 g, 7.55 mmol) in acetic acid (15.1 mL) was irradiated at 150° C. in a microwave reactor. After 1 h, the resulting solution was poured into water and the precipitate was collected via vacuum filtration. The off-white/pink solid was washed with water, dichloromethane and acetonitrile and dried vacuum to afford the title compound (1.65 g, 5.22 mmol, 69% yield). LCMS $(M+H)^+=316.6$.

Step 3: Preparation of benzyl ((5-phenyl-3H-imidazo[4,5-b]pyridin-2-yl)methyl)carbamate

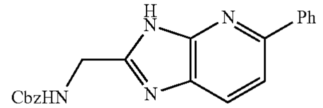 [SMILES: O=C(NCc1nc2ccc(-c3ccccc3)nc2[nH]1)OCc1ccccc1]

To a microwave reaction vial containing benzyl ((5-chloro-3H-imidazo[4,5-b]pyridin-2-yl)methyl)carbamate (300 mg, 0.947 mmol), phenylboronic acid pinacol ester (250 mg, 1.22 mmol), dichloro 1,1'-bis(diphenylphosphino) ferrocene palladium dichloromethane adduct (154 mg, 0.189 mmol), and sodium carbonate (200 mg, 1.89 mmol) was added degassed 1,2-dimethoxyethane (12 mL), ethanol (4 mL) and water (1 mL). The reaction mixture was irradiated at 120° C. in a microwave reactor. After 3 h, the reaction mixture was diluted with water and ethyl acetate and filtered through a pad of Celite. The layers were separated, and the organic layer was washed with brine and the brine layer was extracted once with ethyl acetate. The combined organic layers were dried with anhydrous sodium sulfate and salts were removed via vacuum filtration. Volatile materials were removed using a rotary evaporator. The resulting residue was purified via silica gel flash chromatography (15% to 50% ethyl acetate in dichloromethane) to yield the title compound (162 mg, 0.430 mmol, 45.4% yield). LCMS (ESI) m/z: $[M+H]^+=358.6$.

Step 4: Preparation of (5-phenyl-3H-imidazo[4,5-b]pyridin-2-yl)methanamine

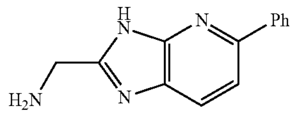 [SMILES: NCc1nc2ccc(-c3ccccc3)nc2[nH]1]

To a mixture of benzyl ((5-phenyl-3H-imidazo[4,5-b]pyridin-2-yl)methyl)carbamate (153 mg, 0.426 mmol) in methanol (5.3 mL) was added 10% Pd/C (9.0 mg, 0.0284 mmol). After the suspension was stirred under a balloon of hydrogen at room temperature overnight, the reaction mixture was filtered through a pad of Celite. Volatile materials were removed using a rotary evaporator to afford the crude title product (51.6 mg, 66.4% yield), which was used without further purification. LCMS (ESI) m/z: $[M+H]^+$ =171.9.

Step 5: Preparation of 1-(methylsulfonyl)-N-((5-phenyl-3H-imidazo[4,5-b]pyridin-2-yl)methyl)-1H-pyrrole-3-carboxamide (Compound 74)

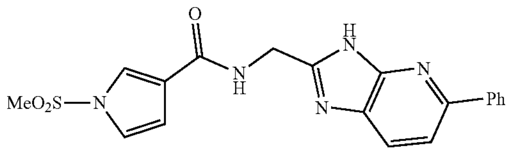 [SMILES: CS(=O)(=O)n1ccc(C(=O)NCc2nc3ccc(-c4ccccc4)nc3[nH]2)c1]

To a solution of (5-phenyl-3H-imidazo[4,5-b]pyridin-2-yl)methanamine (35.1 mg, 0.157 mmol) and 1-(methylsulfonyl)-1H-pyrrole-3-carboxylic acid (44.4 mg, 0.235 mmol) in DMF (2 mL) was added DIPEA (0.082 mL, 0.471 mmol) and HBTU (89.1 mg, 0.235 mmol). After stirring overnight at room temperature, the reaction mixture was diluted with water and ethyl acetate. The layers were separated, and the aqueous layer was extracted twice with ethyl acetate. The combined organic layers were washed twice with water and once with brine. The organic layers were dried with anhydrous sodium sulfate and salts were removed via vacuum filtration. Volatile materials were removed using a rotary evaporator. The resulting residue was purified via an automated reversed-phase prep-HPLC to yield Compound 74 (12.1 mg, 0.0307 mmol, 19.5% yield) as a white powder. LCMS (ESI) m/z: $[M+H]^+$=395.6. $^1$H NMR (400 MHz, DMSO-$d_6$) δ 8.93 (s, 1H), 8.12-8.05 (m, 2H), 7.98 (t, J=2.0 Hz, 1H), 7.88 (t, J=2.0 Hz, 1H), 7.78 (d, J=8.3 Hz, 1H), 7.48 (dd, J=8.4, 6.9 Hz, 2H), 7.42-7.35 (m, 1H), 7.32 (dd, J=3.3, 2.3 Hz, 1H), 6.81 (dd, J=3.4, 1.6 Hz, 1H), 4.67 (d, J=5.6 Hz, 2H), 3.56 (s, 3H).

Example 16. Preparation of benzyl ((6-bromo-1H-benzo[d]imidazol-2-yl)methyl)carbamate (Intermediate 8)

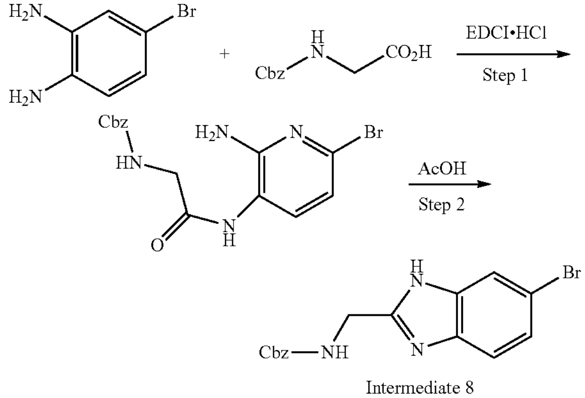

Intermediate 8

Step 1: Preparation of benzyl (2-((2-amino-4-bromophenyl)amino)-2-oxoethyl)carbamate

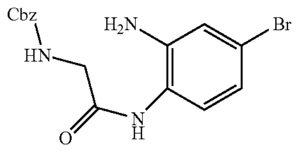 [SMILES: Nc1cc(Br)ccc1NC(=O)CNC(=O)OCc1ccccc1]

To a solution of 6-chloropyridine-2,3-diamine (2.0 g, 13.9 mmol) and ((benzyloxy)carbonyl)glycine (2.9 g, 13.9 mmol) in pyridine (46.3 mL) was added N-(3-dimethylaminopropyl)-N'-ethylcarbodiimide hydrochloride (7.99 g, 41.7 mmol). After stirring overnight at room temperature, the reaction mixture was diluted with water and ethyl acetate. The organic layer was washed twice with water and diluted with brine. The resulting emulsion was filtered through a pad of Celite and the organic layer was dried with anhydrous sodium sulfate. Salts were removed via vacuum filtration and volatile material was removed using a rotary evaporator. The residue was purified by silica gel flash chromatography (20% to 100% ethyl acetate in dichloromethane). The residue was suspended in methanol and solids were removed via vacuum filtration. The filtrate was concentrated to afford the title compound (1.31 g, 3.46 mmol, 32.7% yield). LCMS (ESI) m/z: $[M+H]^+$=377.6 and 378.4.

Step 2: Preparation of benzyl ((6-bromo-1H-benzo[d]imidazol-2-yl)methyl)carbamate (Intermediate 8)

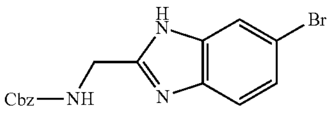 [SMILES: O=C(NCc1nc2ccc(Br)cc2[nH]1)OCc1ccccc1]

A suspension of benzyl (2-((2-amino-4-bromophenyl)amino)-2-oxoethyl)carbamate (2.53 g, 7.55 mmol) in acetic acid (15.1 mL) was irradiated at 150° C. in a microwave reactor. After 1 h, the resulting solution was diluted with water and ethyl acetate. To this mixture was slowly added sodium carbonate (10 g). The layers were separated, and the organic layer was washed with saturated aqueous sodium bicarbonate, brine and dried with anhydrous sodium sulfate. Volatile materials were removed using a rotary evaporator. The resulting residue was purified via silica gel flash chromatography (0% to 4% methanol in dichloromethane) to afford Intermediate 8 (967 mg, 2.68 mmol). LCMS $(M+H)^+$: 359.6 and 361.6.

Example 17. Preparation of Compounds 27 to 29

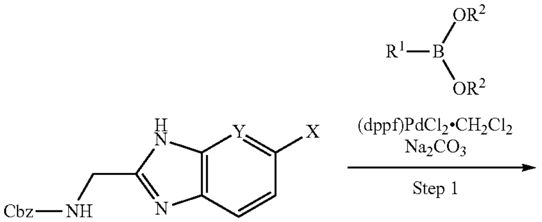

Y = N, X = Cl: Intermediate 7
Y = CH, X = Br: Intermediate 8
Y = N, X = Br: Intermediate 9
Y = CH, X = Br: Intermediate 10

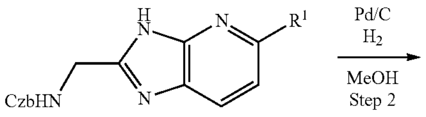

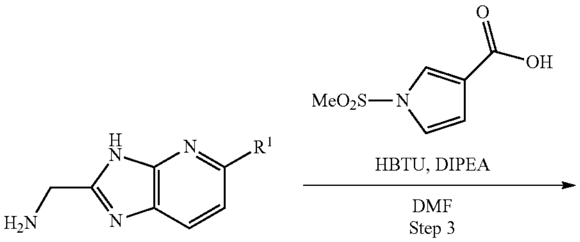

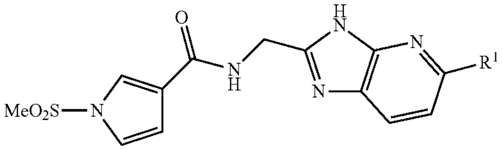

Compounds 27 to 29, shown in Table 7 below, were each synthesized starting from the Intermediates 7, 8, 9, or 10, and the appropriate boronic acid using the synthetic protocol shown in the scheme above.

TABLE 7

| # | LC-MS (m/z) | $^1$H NMR |
|---|---|---|
| 27 | 395.1 | $^1$H NMR (400 MHz, DMSO-$d_6$) δ 8.94 (t, J = 5.8 Hz, 1H), 8.20 (d, J = 1.1 Hz, 1H), 7.88 (t, J = 2.0 Hz, 1H), 7.73 (s, 1H), 7.68-7.63 (m, 2H), 7.57 (d, J = 8.4 Hz, 1H), 7.51-7.42 (m, 3H), 7.35-7.27 (m, 2H), 6.82 (dd, J = 3.3, 1.6 Hz, 1H), 4.65 (d, J = 5.7 Hz, 2H), 3.56 (s, 3H) |
| 28 | 480.1 | $^1$H NMR (400 MHz, DMSO-$d_6$) δ 13.14 (s, 1H), 12.60 (s, 1H), 8.94 (dt, J = 37.4, 5.7 Hz, 1H), 8.13 (d, J = 8.0 Hz, 1H), 8.07 (s, 1H), 7.99 (dd, J = 41.8, 8.4 Hz, 1H), 7.91-7.84 (m, 2H), 7.62 (td, J = 8.0, 2.6 Hz, 1H), 7.40 (d, J = 5.8 Hz, 1H), 7.32 (ddd, J = 5.7, 3.2, 2.3 Hz, 1H), 6.81 (ddd, J = 7.1, 3.3, 1.7 Hz, 1H), 4.68 (dd, J = 14.1, 5.7 Hz, 2H), 3.57 (d, J = 1.6 Hz, 3H) |
| 29 | 480.1 | $^1$H NMR (400 MHz, DMSO-$d_6$) δ 13.09 (s, 1H), 12.57 (s, 1H), 8.93 (dt, J = 38.3, 5.7 Hz, 1H), 8.21 (dd, J = 8.8, 3.2 Hz, 2H), 7.98 (dd, J = 41.7, 8.3 Hz, 1H), 7.88 (dt, J = 4.2, 2.0 Hz, 1H), 7.82 (dd, J = 8.3, 5.2 Hz, 1H), 7.47 (dd, J = 8.8, 2.9 Hz, 2H), 7.32 (ddd, J = 5.7, 3.1, 2.2 Hz, 1H), 6.81 (ddd, J = 7.1, 3.4, 1.6 Hz, 1H), 4.67 (dd, J = 13.7, 5.7 Hz, 2H), 3.56 (s, 3H) |

Example 18. Preparation of 1-[4-(4,4,5,5-tetramethyl-1,3,2-dioxaborolan-2-yl)phenyl]azetidine

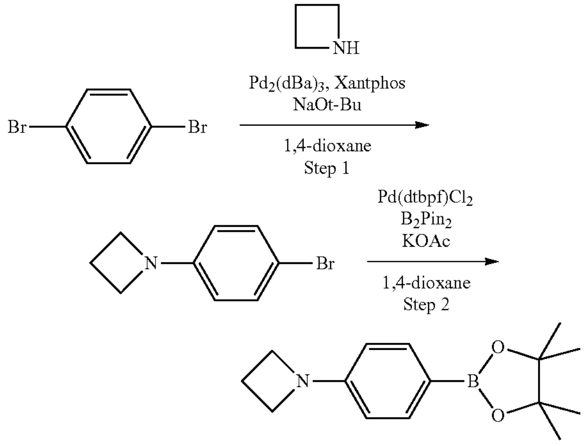

Step 1: Preparation of 1-(4-bromophenyl)azetidine

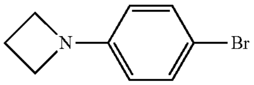 [SMILES: Brc1ccc(N2CCC2)cc1]

To a mixture of azetidine (0.0944 mL, 1.40 mmol), 1,4-dibromobenzene (0.163 mL, 1.27 mmol), (5-diphenylphosphanyl-9,9-dimethyl-xanthen-4-yl)-diphenyl-phosphane (147 mg, 0.254 mmol) and tris(dibenzylideneacetone) dipalladium(0) (116 mg, 0.127 mmol) in 1,4-dioxane (3 mL) was added t-BuONa (367 mg, 3.82 mmol) under a $N_2$ atmosphere. After stirring at 60° C. for 2 h, the reaction mixture was diluted with methanol, filtered and concentrated under reduced pressure to afford a residue. The residue was purified by silica gel flash chromatography (0-50% ethyl acetate/petroleum ether gradient) to afford the title compound (200 mg, 0.943 mmol, 74.2% yield) as a yellow solid. LCMS (ESI) m/z: $[M+H]^+$=211.8. $^1$H NMR (400 MHz, $CDCl_3$) δ 7.36-7.05 (m, 2H), 6.37-6.12 (m, 2H), 3.77 (d, J=7.2 Hz, 4H), 2.32-2.25 (m, 2H).

Step 2: Preparation of 1-[4-(4,4,5,5-tetramethyl-1,3,2-dioxaborolan-2-yl)phenyl]azetidine

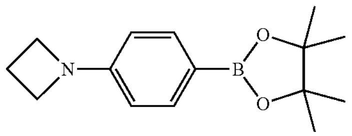 [SMILES: CC1(C)OB(c2ccc(N3CCC3)cc2)OC1(C)C]

A mixture of 1-(4-bromophenyl)azetidine (150 mg, 0.707 mmol), 4,4,5,5-tetramethyl-2-(4,4,5,5-tetramethyl-1,3,2-dioxaborolan-2-yl)-1,3,2-dioxaborolane (180 mg, 0.707 mmol), KOAc (208 mg, 2.12 mmol) and [1,1'-bis(di-tert-butylphosphino)ferrocene]dichloropalladium(II) (46.1 mg, 0.0707 mmol) in 1,4-dioxane (1 mL) was degassed and purged with $N_2$ three times. After stirring at 80° C. for 2 h under a $N_2$ atmosphere, the reaction mixture was diluted with water and extracted three times with ethyl acetate. The combined organic layers were washed with brine, dried over $Na_2SO_4$, filtered and concentrated under reduced pressure to afford a residue. The residue was purified by silica gel flash chromatography (0-30% ethyl acetate/petroleum ether gradient) to afford the title compound (150 mg, 0.579 mmol, 81.8% yield) as a yellow solid. LCMS (ESI) m/z: $[M+H]^+$ =260.0. $^1$H NMR (400 MHz, $CDCl_3$) δ 7.59 (d, J=8.4 Hz, 2H), 6.40-6.29 (m, 2H), 3.84 (d, J=7.2 Hz, 4H), 2.34-2.26 (m, 2H), 1.25 (s, 12H).

Example 19. Preparation of 1-(3-(4,4,5,5,-tetramethyl-1,3,2-dioxaboronlan-2-yl)phenyl)azetidine, (2S,6R)-2,6-dimethyl-4-(3-(4,4,5,5-tetramethyl-1,3,2-dioxaborolan-2-yl)phenyl)morpholine, 1-(3-(4,4,5,5-tetramethyl-1,3,2-dioxaborolan-2-yl)phenyl)piperidin-4-ol, and (2S,6R)-2,6-dimethyl-4-(4-(4,4,5,5-tetramethyl-1,3,2-dioxaborolan-2-yl)phenyl) morpholine The compounds shown in Table 8 below were each synthesized utilizing the synthetic protocol described in Example 18 above from the appropriate dibromobenzene and azetidine, 2,6-dimethylmorpholine, or 4-hydroxypiperidine.

TABLE 8

| Structure | LC-MS (m/z) | $^1$H NMR |
|---|---|---|
| 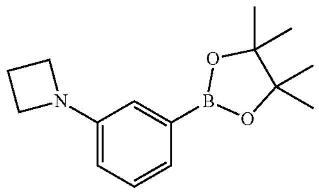 [SMILES: CC1(C)OB(c2cccc(N3CCC3)c2)OC1(C)C] 1-(3-(4,4,5,5-tetramethyl-1,3,2-dioxaboronlan-2-yl)phenyl)azetidine | 260.0 | $^1$H NMR (400 MHz, $CDCl_3$) δ 7.18-7.09 (m, 2H), 6.81 (d, J = 2.4 Hz, 1H), 6.50-6.47 (m, 1H), 3.82 (d, J = 7.2 Hz, 4H), 2.34-2.21 (m, 2H), 1.27 (s, 12H) |
| 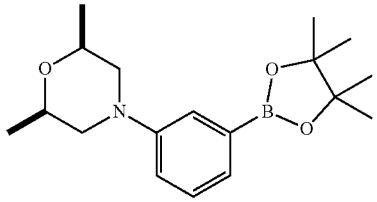 (2S,6R)-2,6-dimethyl-4-(3-(4,4,5,5-tetramethyl-1,3,2-dioxaborolan-2-yl)phenyl)morpholine | 318.2 | $^1$H NMR (400 MHz, $CDCl_3$) δ 7.38-7.26 (m, 3H), 7.06-6.99 (m, 1H), 3.87-3.75 (m, 2H), 3.55-3.46 (m, 2H), 2.50-2.36 (m, 2H), 1.36 (s, 12H), 1.29-1.28 (m, 6H) |
| 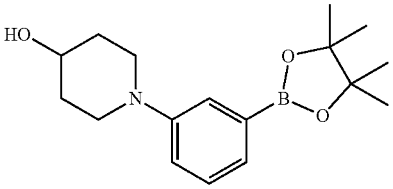 [SMILES: CC1(C)OB(c2cccc(N3CCC(O)CC3)c2)OC1(C)C] 1-(3-(4,4,5,5-tetramethyl-1,3,2-dioxaborolan-2-yl)phenyl)piperidin-4-ol | 304.1 | $^1$H NMR (400 MHz, $CDCl_3$) δ 7.40 (d, J = 2.0 Hz, 1H), 7.32-7.23 (m, 2H), 7.09-7.02 (m, 1H), 3.88-3.78 (m, 1H), 3.64-3.53 (m, 2H), 2.98-2.87 (m, 2H), 2.04-1.98 (m, 2H), 1.75-1.64 (m, 2H), 1.34 (s, 12H) |
| 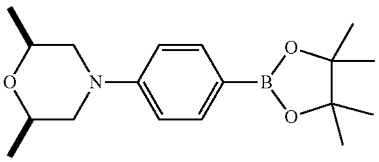 [SMILES: C[C@@H]1CN(c2ccc(B3OC(C)(C)C(C)(C)O3)cc2)C[C@H](C)O1] | 318.2 | |

TABLE 8-continued

| Structure | LC-MS (m/z) | $^1$H NMR |
|---|---|---|
| (2S, 6R)-2,6-dimethyl-4-(4-(4,4,5,5-tetramethyl-1,3,2-dioxaborolan-2-yl)phenyl)morpholine | | |

Example 20. Preparation of 1-(isopropylsulfonyl)-1H-pyrrole-3-carboxylate acid

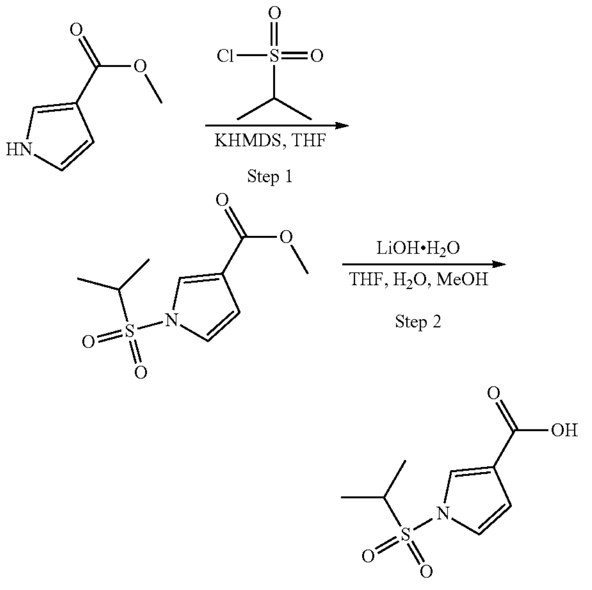

Step 1: Preparation of methyl 1-(isopropylsulfonyl)-1H-pyrrole-3-carboxylate

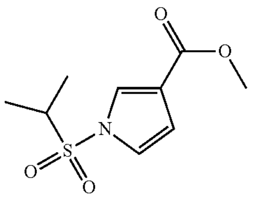

To a cooled solution (0° C.) of methyl 1H-pyrrole-3-carboxylate (2 g, 16.0 mmol) in THE (20 mL) was added a 1 M solution of KHMDS (32.0 mL, 32 mL). After stirring at 0° C. for 30 min, propane-2-sulfonyl chloride (1.96 mL, 17.6 mmol) was added to the reaction mixture and the mixture was warmed to room temperature. After 15.5 h, the reaction mixture was poured into water slowly and extracted three times with ethyl acetate. The combined organic layers were washed with brine, dried over anhydrous $Na_2SO_4$, filtered and concentrated under reduced pressure to afford a residue. The residue was purified by silica gel flash chromatography (0-30% ethyl acetate/petroleum ether gradient) to afford the title compound (1.2 g, 5.19 mmol, 32.5% yield) as a white solid. $^1$H NMR (400 MHz, $CDCl_3$) δ 7.70-7.69 (m, 1H), 7.07-7.06 (m, 1H), 6.75-6.73 (m, 1H), 3.85 (s, 3H), 3.49-3.39 (m, 1H), 1.35 (d, J=6.8 Hz, 6H).

Step 2: Preparation of 1-(isopropylsulfonyl)-1H-pyrrole-3-carboxylic acid

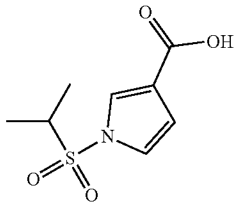

To a mixture of methyl 1-(isopropylsulfonyl)-1H-pyrrole-3-carboxylate (500 mg, 2.16 mmol) in THE (10 mL) and methanol (5 mL) was added a solution of $LiOH \cdot H_2O$ (272 mg, 6.49 mmol) dissolved in water (5 mL). After stirring at room temperature for 2 h, the reaction mixture was acidified with 1 N HCl to pH=3 and extracted three times with ethyl acetate. The combined organic layers were dried over anhydrous $Na_2SO_4$, filtered and concentrated under reduced pressure to give a residue. The residue was purified by reversed phase chromatography and concentrated under reduced pressure to remove acetonitrile. The solution was extracted three times with ethyl acetate. The combined organic layers were dried over anhydrous $Na_2SO_4$, filtered and concentrated under reduced pressure to afford the title compound (400 mg, 1.84 mmol, 85.2% yield) as a white solid. LCMS (ESI) m/z: $[M+H]^+$=218.0. $^1$H NMR (400 MHz, $CDCl_3$) δ 7.80-7.78 (m, 1H), 7.11-7.09 (m, 1H), 6.80-6.78 (m, 1H), 3.50-3.43 (m, 1H), 1.37 (d, J=6.8 Hz, 6H).

Example 21. Preparation of 1-(methylsulfonyl)-1H-pyrrole-3-carboxylic acid

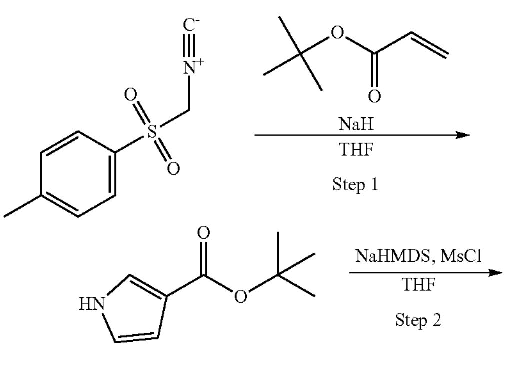

-continued

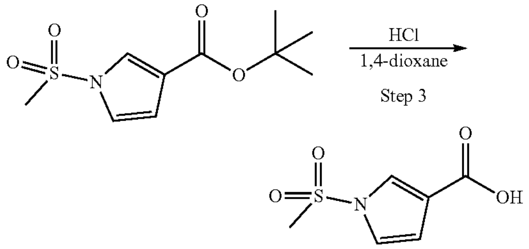

Step 1: Preparation of tert-butyl 1H-pyrrole-3-carboxylate

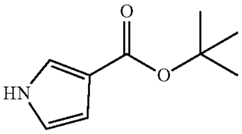

To a mixture of tert-butyl prop-2-enoate (78.6 mL, 542 mmol) and 1-(isocyanomethylsulfonyl)-4-methylbenzene (106 g, 542 mmol) in THE (1300 mL) was added 60% NaH in mineral oil (25.97 g, 649 mmol) slowly at 30° C. over 1 h and then heated to 70° C. After 2 h, the reaction mixture was poured into saturated aqueous $NH_4Cl$ solution and extracted three times with ethyl acetate. The combined organic phase was washed twice with brine, dried over anhydrous $Na_2SO_4$, filtered and concentrated under reduced pressure to afford a residue. The residue was purified by silica gel column chromatography (petroleum ether/ethyl acetate=20:1-3:1) to afford the title compound (41.5 g, 236 mmol, 43% yield) as a yellow solid. LCMS (ESI) m/z $[M+Na]^+$=180.4. $^1$H NMR (400 MHz, $CDCl_3$) δ 8.36 (br s, 1H), 7.35-7.25 (m, 1H), 6.71-6.62 (m, 1H), 6.59-6.49 (m, 1H), 1.48 (s, 9H).

Step 2: Preparation of tert-butyl 1-methylsulfonylpyrrole-3-carboxylate

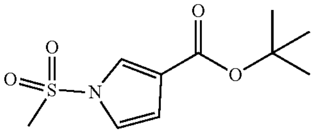 [SMILES: CC(C)(C)OC(=O)c1ccn(S(C)(=O)=O)c1]

To a cooled solution (0° C.) of tert-butyl 1H-pyrrole-3-carboxylate (40.5 g, 242 mmol) in THE (1500 mL) was added a 1 M solution of NaHMDS (484 mL, 484 mmol). After stirring at 0° C. for 30 min, methanesulfonyl chloride (28.1 mL, 363 mmol) slowly and the mixture was warmed to 30° C. After 16 h, the reaction mixture was slowly poured into saturated aqueous $NH_4Cl$ solution and extracted three times with ethyl acetate. The combined organic layers were washed twice with brine, dried over anhydrous $Na_2SO_4$, filtered and concentrated under reduced pressure to afford a residue. The residue was purified by silica gel chromatography (petroleum ether/ethyl acetate=10/1) to afford a yellow solid. The yellow solid was triturated with methyl tert-butyl ether at room temperature for 20 min, filtered and dried in vacuum to afford the title compound (25.7 g, 105 mmol, 43% yield) as a white solid. $^1$H NMR (400 MHz, $CDCl_3$) δ 7.66-7.64 (m, 1H), 7.10-7.08 (m, 1H), 6.73-6.71 (m, 1H), 3.21 (s, 3H), 1.56 (s, 9H).

Step 3: Preparation of 1-methylsulfonylpyrrole-3-carboxylic acid

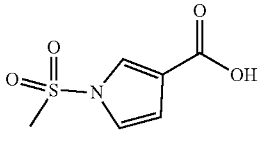

To a mixture of tert-butyl 1-methylsulfonylpyrrole-3-carboxylate (25.7 g, 105 mmol) in 1,4-dioxane (100 mL) was added a 4 M solution of HCl in 1,4-dioxane (400 mL, 1.6 mol) at 15° C. After stirring at 15° C. for 14 h, the reaction mixture was concentrated under reduced pressure to afford a residue. The residue was triturated with methyl tert-butyl ether at 15° C. for 16 h. The mixture was filtered and dried in vacuum to afford the title compound (18.7 g, 98.8 mmol, 94% yield) as a white solid. LCMS (ESI) m/z $[M+H]^+$=189.8. $^1$H NMR (400 MHz, methanol-$d_4$) δ 7.78-7.77 (m, 1H), 7.25-7.23 (m, 1H), 6.72-6.70 (m, 1H), 3.37 (s, 3H).

Example 22. Preparation of 5-methyl-1-(methylsulfonyl)-1H-pyrrole-3-carboxylic acid The compound shown in Table 9 below was synthesized using an analogous method to the method described in Example 21 above.

TABLE 9

| Structure | LC-MS (m/z) | $^1$H NMR |
|---|---|---|
| 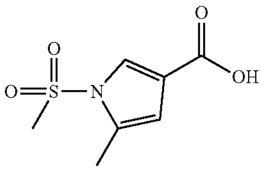 | 204.1 | $^1$H NMR (400 MHz, methanol-$d_4$) δ 7.69 (d, J = 1.6 Hz, 1H), 6.41 (s, 1H), 3.35 (s, 3H), 2.44 (d, J = 0.8 Hz, 3H) |

Example 23. Preparation of methyl 3-(4,4,5,5-tetramethyl-1,3,2-dioxaborolan-2-yl)-5,6-dihydropyridine-1(2H)-carboxylate and methyl 5-(4,4,5,5-tetramethyl-1,3,2-dioxaborolan-2-yl)-3,4-dihydropyridine-1(2H)-carboxylate

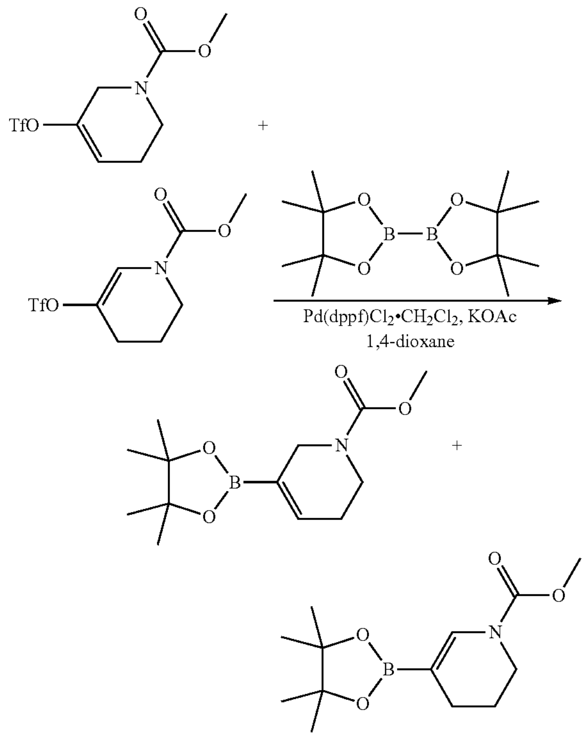

To a mixture of methyl 3-(((trifluoromethyl)sulfonyl)oxy)-5,6-dihydropyridine-1(2H)-carboxylate (75 g, 135 mmol) and 4,4,5,5-tetramethyl-2-(4,4,5,5-tetramethyl-1,3,2-dioxaborolan-2-yl)-1,3,2-dioxaborolane (37.7 g, 148 mmol) in 1,4-dioxane (600 mL) was added KOAc (39.7 g, 405 mmol) and $Pd(dppf)Cl_2 \cdot CH_2Cl_2$ (5.51 g, 6.74 mmol) at room temperature under a $N_2$ atmosphere. After stirring at 80° C. for 3 h, the reaction mixture was diluted with water and extracted three times with ethyl acetate. The combined organic layers were dried over anhydrous $Na_2SO_4$, filtered and concentrated under reduced pressure to give a residue. The residue was purified by silica gel flash chromatography (0-30% ethyl acetate/petroleum ether gradient) to give methyl 3-(4,4,5,5-tetramethyl-1,3,2-dioxaborolan-2-yl)-5,6-dihydropyridine-1(2H)-carboxylate (13 g, 48.7 mmol, 36.1% yield) as a white solid and methyl 5-(4,4,5,5-tetramethyl-1,3,2-dioxaborolan-2-yl)-3,4-dihydropyridine-1(2H)-carboxylate (9.2 g, 34.4 mmol, 25.5% yield) as a yellow oil.

Example 24. Preparation of 1-(methylsulfonyl)-N-((2-phenyl-1,6-naphthyridin-7-yl)methyl)-1H-pyrrole-3-carboxamide (Compound 61)

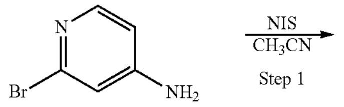

-continued

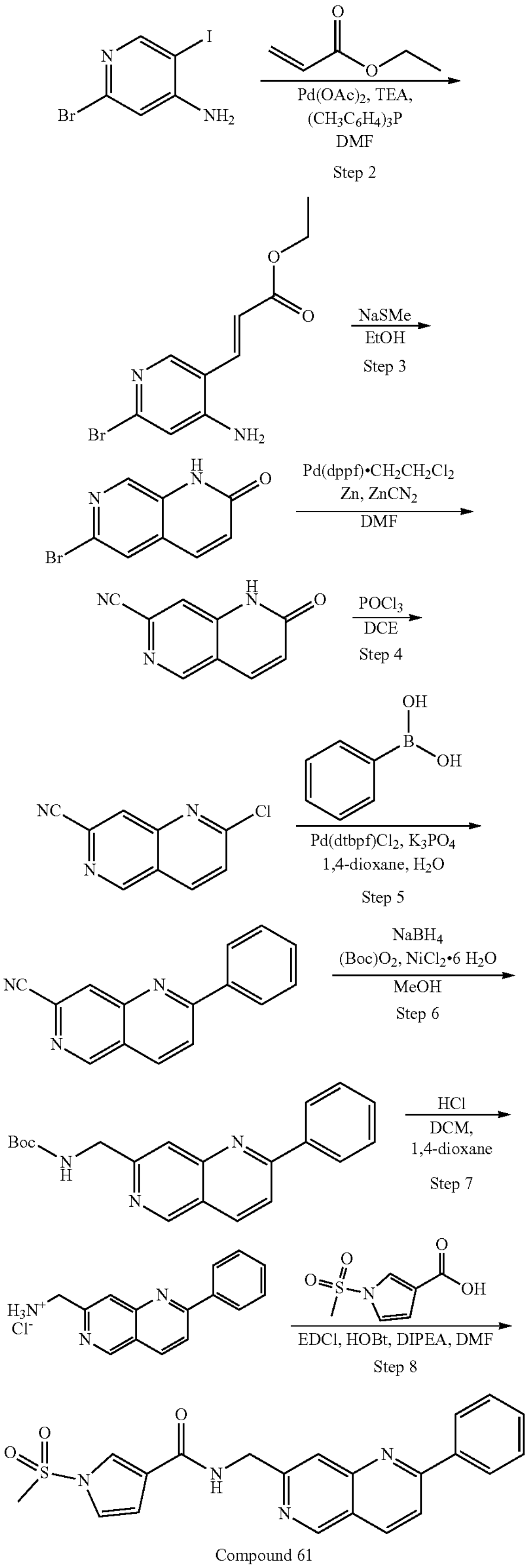

Compound 61

Step 1: Preparation of 2-bromo-5-iodopyridin-4-amine

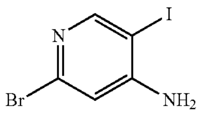

To a solution of 2-bromopyridin-4-amine (80 g, 347 mmol) in acetonitrile (2000 mL) was added NIS (125 g, 555 mmol) at 80° C. After stirring at 80° C. for 16 h, additional NIS (52.0 g, 231 mmol) was added to the reaction and stirred at 80° C. After 4 h, additional NIS (52.0 g, 231 mmol) was added to the mixture was stirred at 80° C. After stirring an additional 16 h, the reaction mixture was concentrated under reduced pressure. The residue was diluted with saturated aqueous $Na_2SO_3$ and extracted twice with ethyl acetate. The combined organic layers were washed with brine, dried over $Na_2SO_4$, filtered and concentrated under reduced pressure to give a residue. The residue was purified by silica gel column chromatography (petroleum ether/ethyl acetate=20:3) to afford the title compound (75 g, 251 mmol, 54.3% yield) as a light yellow solid. LCMS (ESI) m/z: $[^{79}BrM+H]^+$=299.0. $^1H$ NMR (400 MHz, $CDCl_3$) δ 8.31 (s, 1H), 6.78 (s, 1H), 4.75 (br s, 2H).

Step 2: Preparation of (E)-ethyl 3-(4-amino-6-bromopyridin-3-yl)acrylate

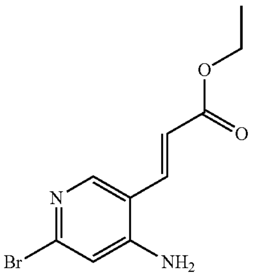

To a solution of 2-bromo-5-iodopyridin-4-amine (120 g, 401 mmol) in DMF (1200 mL) was added ethyl prop-2-enoate (87.3 mL, 803 mmol), TEA (83.82 mL, 602 mmol), $Pd(OAc)_2$ (4.51 g, 20.1 mmol) and tri-o-tolylphosphine (12.2 g, 40.2 mmol) under $N_2$. The mixture was stirred at 100° C. under $N_2$. After 3 h, the reaction mixture was diluted with water and extracted twice with ethyl acetate. The combined organic layers were washed with brine, dried over $Na_2SO_4$, filtered and concentrated under reduced pressure. The residue was purified by silica gel column chromatography (petroleum ether/ethyl acetate=20:3) to afford the title compound (100 g, 369 mmol, 91.9% yield) as a light yellow solid. LCMS (ESI) m/z: $[^{79}BrM+H]^+$=271.0. $^1H$ NMR (400 MHz, DMSO-$d_6$) δ 8.23 (s, 1H), 7.73 (d, J=16.0 Hz, 1H), 6.90-6.67 (m, 3H), 6.52 (d, J=16.0 Hz, 1H), 4.20-4.15 (m, 2H), 1.26-1.23 (m, 3H).

Step 3: Preparation of 7-bromo-1,6-naphthyridin-2(1H)-one

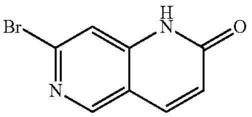 [SMILES: O=c1ccc2cnc(Br)cc2[nH]1]

To a solution of (E)-ethyl 3-(4-amino-6-bromopyridin-3-yl)acrylate (90 g, 332 mmol) in ethanol (450 mL) was added NaSMe (59.0 g, 855.38 mmol) and the mixture was stirred at 60° C. After 2 h, the reaction mixture was diluted with water and neutralized with 1 N HCl to pH 7.0. The mixture was filtered and the filter cake was washed with methyl tert-butyl ether and dried under reduced pressure to afford the title compound (60 g, 264 mmol, 79.5% yield) as a brown solid. LCMS (ESI) m/z: $[^{79}BrM+H]^+$=225. $^1H$ NMR (400 MHz, DMSO-$d_6$) δ 12.09 (br s, 1H), 8.65 (s, 1H), 7.99 (d, J=9.6 Hz, 1H), 7.36 (s, 1H), 6.62 (d, J=9.6 Hz, 1H).

Step 4: Preparation of 2-oxo-1,2-dihydro-1,6-naphthyridine-7-carbonitrile

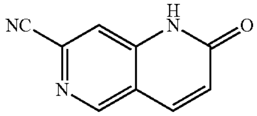 [SMILES: N#Cc1cc2[nH]c(=O)ccc2cn1]

To a solution of 7-bromo-1,6-naphthyridin-2(1H)-one (50 g, 222 mmol), $Pd(dppf)Cl_2 \cdot CH_2Cl_2$ (5.01 g, 6.13 mmol) and $Zn(CN)_2$ (39.1 g, 333 mmol) in DMF (1000 mL) was added Zn powder (2.91 g, 44.4 mmol) under $N_2$. The mixture was degassed and purged with $N_2$ for 3 times and stirred at 85° C. under $N_2$ atmosphere. After 2 h, the reaction mixture was diluted with water and extracted seven times with ethyl acetate. The combined organic layers were dried over $Na_2SO_4$, filtered and concentrated under reduced pressure. The residue was triturated with methanol. The suspension was filtered, and the filter cake was washed with methyl tert-butyl ether and dried under reduced pressure to afford the title compound (32 g, 187 mmol, 84.2% yield) as an off-white solid. LCMS (ESI) m/z: $[M+H]^+$=172.2. $^1H$ NMR (400 MHz, DMSO-$d_6$) δ 12.36 (br s, 1H), 8.96 (s, 1H), 8.08 (d, J=9.6 Hz, 1H), 7.66 (s, 1H), 6.76 (d, J=9.6 Hz, 1H).

Step 5: Preparation of 2-chloro-1,6-naphthyridine-7-carbonitrile

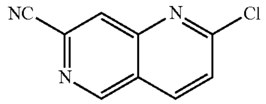 [SMILES: N#Cc1cc2nc(Cl)ccc2cn1]

To a solution of 2-oxo-1,2-dihydro-1,6-naphthyridine-7-carbonitrile (28 g, 164 mmol) in 1,2-dichloroethane (700 mL) was added $POCl_3$ (76.0 mL, 818 mmol) and the mixture was stirred at 60° C. After 14 h, additional of $POCl_3$ (150 mL, 1.61 mol) was added to the reaction mixture. After stirring at 60° C. for an additional 2 h, the reaction mixture was added into ice water drop wise. The resulting mixture was basified with solid $NaHCO_3$ to pH=7.0 and filtered to give a filter cake. The solid was triturated with ethyl acetate. The solid was collected with filtered and dried under reduced pressure to afford the title compound (23 g, 119 mmol, 73.0% yield) as an off-white solid. LCMS (ESI) m/z: $[M+H]^+$=190.1. $^1H$ NMR (400 MHz, DMSO-$d_6$) δ 9.57 (s, 1H), 8.79 (d, J=8.8 Hz, 1H), 8.68 (s, 1H), 7.99 (d, J=8.8 Hz, 1H).

Step 6: Preparation of 2-phenyl-1,6-naphthyridine-7-carbonitrile

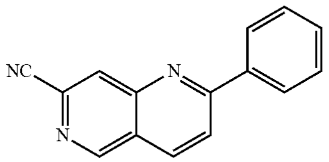 [SMILES: N#Cc1cc2nc(-c3ccccc3)ccc2cn1]

A mixture of 2-chloro-1,6-naphthyridine-7-carbonitrile (300 mg, 1.58 mmol), phenylboronic acid (289 mg, 2.37 mmol), [1,1'-bis(di-tert-butylphosphino)ferrocene]dichloropalladium (103 mg, 0.158 mmol) and $K_3PO_4$ (1.01 g, 4.75 mmol) in dioxane (9 mL) and $H_2O$ (1.8 mL) was degassed and purged with $N_2$ for 3 times, and then stirred at 60° C. under $N_2$ atmosphere. After 3 h, water was added to the mixture, and then extracted three times with ethyl acetate. The combined organic layer was dried over $Na_2SO_4$, filtered and concentrated to give a residue. The residue was purified by silica gel flash chromatography (0-50% ethyl acetate/petroleum ether gradient) to afford the title compound (395 mg, 1.54 mmol, 97.2% yield) as an off-white solid. $^1H$ NMR (400 MHz, $CDCl_3$) δ 9.30 (d, J=0.8 Hz, 1H), 8.47-8.39 (m, 2H), 8.28-8.15 (m, 3H), 7.63-7.54 (m, 3H).

Step 7: Preparation of tert-butyl ((2-phenyl-1,6-naphthyridin-7-yl)methyl)carbamate

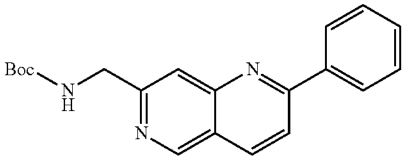 [SMILES: CC(C)(C)OC(=O)NCc1cc2nc(-c3ccccc3)ccc2cn1]

To a cooled solution (−10° C.) of 2-phenyl-1,6-naphthyridine-7-carbonitrile (300 mg, 1.30 mmol), $(Boc)_2O$ (849 mg, 3.89 mmol) and $NiCl_2.6H_2O$ (61.7 mg, 0.259 mmol) in MeOH (45 mL) was added $NaBH_4$ (491 mg, 13.0 mmol). After stirring at room temperature for 16 h, the reaction mixture was concentrated under reduced pressure. The residue was diluted with saturated aqueous $NH_4Cl$ and extracted three times with ethyl acetate. The combined organic layers were washed with brine, dried over $Na_2SO_4$, filtered, and concentrated under reduced pressure to afford a residue. The residue was purified by silica gel flash chromatography (0-60% ethyl acetate/petroleum ether gradient) to afford the title compound (150 mg, 0.403 mmol, 31.0% yield) as a yellow solid. $^1H$ NMR (400 MHz, $CDCl_3$) δ 9.22 (s, 1H), 8.33 (d, J=8.8 Hz, 1H), 8.22-8.12 (m, 2H), 8.03-7.91 (m, 2H), 7.59-7.50 (m, 3H), 5.50 (s, 1H), 4.68 (d, J=5.2 Hz, 2H), 1.50 (s, 9H).

Step 8: Preparation of (2-phenyl-1,6-naphthyridin-7-yl)methanaminium chloride

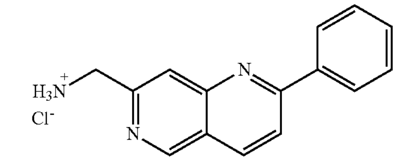 [SMILES: [Cl-] ; NCc1cc2nc(-c3ccccc3)ccc2cn1]

To a cooled solution (0° C.) of tert-butyl ((2-phenyl-1,6-naphthyridin-7-yl)methyl)carbamate (190 mg, 0.566 mmol) in dichloromethane (6 mL) was added solution of 4 M HCl in 1,4-dioxane (1.9 mL, 7.6 mmol). After stirring at room temperature for 1 h, the reaction mixture was concentrated to afford the title compound (190 mg) as a light yellow solid, which was used without further purification. LCMS (ESI) m/z: $[M+H]^+$=236.1.

Step 9: Preparation of 1-(methylsulfonyl)-N-((2-phenyl-1,6-naphthyridin-7-yl)methyl)-1H-pyrrole-3-carboxamide (Compound 61)

Compound 61

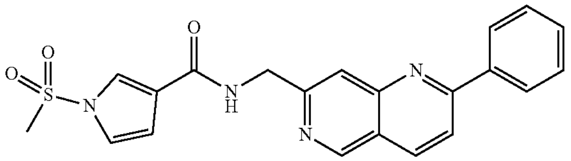

To a solution of 1-methylsulfonylpyrrole-3-carboxylic acid (63.4 mg, 0.335 mmol), EDCI (98.8 mg, 0.515 mmol), HOBt (69.6 mg, 0.515 mmol) and DIPEA (0.224 mL, 1.29 mmol) in DMF (1 mL) was added (2-phenyl-1,6-naphthyridin-7-yl)methanaminium chloride (70 mg, 0.258 mmol). After stirring at room temperature for 3 h, the reaction mixture was diluted with water and extracted three times with ethyl acetate. The combined organic layers were washed with brine, dried over $Na_2SO_4$, filtered and concentrated under reduced pressure to give a residue. The residue was purified by reversed-phase prep-HPLC (water:ACN:FA) to afford Compound 61 (43.4 mg, 0.107 mmol, 41.4% yield) as a white solid. LCMS (ESI) m/z: $[M+H]^+$=407.0. $^1H$ NMR (400 MHz, DMSO-$d_6$) δ 9.37 (d, J=0.6 Hz, 1H), 9.06-8.97 (m, 1H), 8.68-8.63 (m, 1H), 8.33-8.25 (m, 3H), 7.94-7.89 (m, 1H), 7.79-7.75 (m, 1H), 7.61-7.51 (m, 3H), 7.36-7.31 (m, 1H), 6.88-6.82 (m, 1H), 4.73 (d, J=6.0 Hz, 2H), 3.59 (s, 3H).

Example 25. Preparation of Compounds 62 and 63

Compounds 62 and 63, shown in Table 10 below, were synthesized starting from 2-chloro-1,6-naphthyridine-7-carbonitrile and the corresponding boronic acid or boronic ester utilizing the synthetic protocol described in Example 24 above.

TABLE 10

| # | LC-MS (m/z) | $^1$H NMR |
| --- | --- | --- |
| 62 | 437.0 | $^1$H NMR (400 MHz, DMSO-$d_6$) δ 9.37 (s, 1H), 9.01-8.98 (m, 1H), 8.64 (d, J = 9.2 Hz, 1H), 8.28 (d, J = 8.8 Hz, 1H),7.91-7.90 (m, 1H), 7.87-7.82 (m, 2H), 7.78 (S, 1H), 7.50-7.46 (m, 1H), 7.34-7.32 (m, 1H), 7.13-7.11 (m, 1H), 6.85-6.84 (m, 1H), 4.72 (d, J = 5.6 Hz, 2H), 3.86 (s, 3H), 3.58 (s, 3H) |
| 63 | 462.1 | $^1$H NMR (400 MHz, DMSO-$d_6$) δ 9.22 (s, 1H), 8.98-8.97 (m, 1H), 8.47 (d, J = 8.8 Hz, 1H), 8.17-8.12 (m, 3H), 7.91-7.90 (m, 1H), 7.65 (s, 1H), 7.34-7.32 (m, 1H), 6.85-6.84 (m, 1H), 6.51 (d, J = 9.2 Hz, 2H), 4.69 (br d, J = 5.6 Hz, 2H), 3.94-3.91 (m, 4H), 3.58 (s, 3H), 2.39-3.35 (m, 2H) |

Example 26. Preparation of N-[[2-[3-(azetidin-1-yl)phenyl]-1,6-naphthyridin-7-yl]methyl]-1-methylsulfonyl-pyrrole-3-carboxamide (Compound 64)

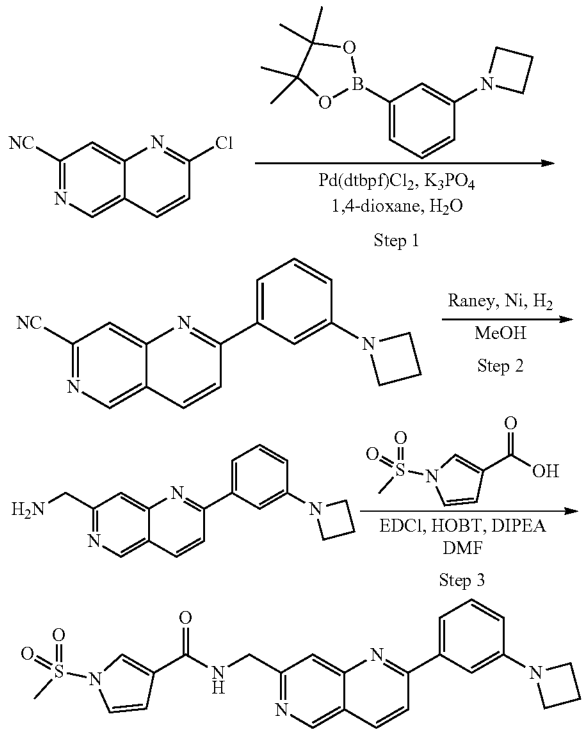

Compound 64

Step 1: Preparation of 2-[3-(azetidin-1-yl)phenyl]-1,6-naphthyridine-7-carbonitrile

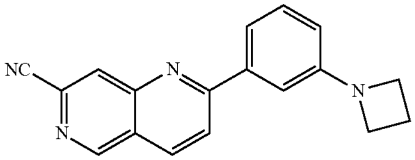 [SMILES: N#Cc1cc2nc(-c3cccc(N4CCC4)c3)ccc2cn1]

A mixture of 1-[3-(4,4,5,5-tetramethyl-1,3,2-dioxaborolan-2-yl)phenyl]azetidine (1.8 g, 3.30 mmol), 2-chloro-1,6-naphthyridine-7-carbonitrile (626 mg, 3.30 mmol) and $K_3PO_4$ (2.10 g, 9.90 mmol) in 1,4-dioxane (18 mL) and $H_2O$ (1.8 mL) was added [1,1'-bis(di-tert-butylphosphino)ferrocene]dichloropalladium (215 mg, 0.330 mol). After stirring at 80° C. for 12 h, the reaction mixture was poured into water and extracted three times with ethyl acetate. The combined organic layers were dried over anhydrous $Na_2SO_4$, filtered, and concentrated under reduced pressure to afford a residue. The residue was purified by silica gel flash chromatography (0-48% ethyl acetate/petroleum ether gradient) to afford the title compound (900 mg, 3.05 mmol, 92.3% yield) as a red solid. LCMS (ESI) m/z: $[M+H]^+$= 287.2. $^1$HNMR (400 MHz, DMSO-$d_6$) δ 9.48 (s, 1H), 8.73 (d, J=8.4 Hz, 1H), 8.64 (s, 1H), 8.44 (d, J=8.8 Hz, 1H), 7.59 (d, J=7.6 Hz, 1H), 7.39-7.34 (m, 1H), 7.29-7.27 (m, 1H), 6.62-6.59 (m, 1H), 3.92-3.88 (m, 4H), 2.37-2.33 (m, 2H).

Step 2: Preparation of [2-[3-(azetidin-1-yl)phenyl]-1,6-naphthyridin-7-yl]methanamine

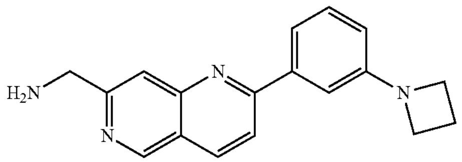 [SMILES: NCc1cc2nc(-c3cccc(N4CCC4)c3)ccc2cn1]

A mixture of 2-[3-(azetidin-1-yl)phenyl]-1,6-naphthyridine-7-carbonitrile (800 mg, 2.79 mmol) and Raney-Ni (400 mg, 4.67 mmol) in methanol (8 mL) was degassed and purged with $H_2$ (15 psi). After stirring at room temperature for 12 h, the reaction mixture was filtered, and the filtrate was concentrated to afford the title compound (700 mg, 1.90 mmol, 68.1% yield) as a brown oil. LCMS (ESI) m/z: $[M+H]^+$=291.

Step 5: Preparation of N-[[2-[3-(azetidin-1-yl)phenyl]-1,6-naphthyridin-7-yl]methyl]-1-methylsulfonyl-pyrrole-3-carboxamide (Compound 64)

Compound 64

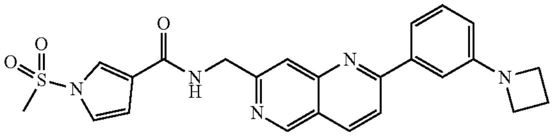

To a mixture of 1-methylsulfonylpyrrole-3-carboxylic acid (32.6 mg, 0.172 mmol), EDCI (49.5 mg, 0.258 mmol), HOBt (34.9 mg, 0.258 mmol) and DIPEA (150 μL, 0.861 mmol) in DMF (1 mL) was added [2-[3-(azetidin-1-yl)phenyl]-1,6-naphthyridin-7-yl]methanamine (50 mg, 0.172 mmol). After stirring at room temperature for 8 h, the reaction mixture was diluted with water and extracted four times with ethyl acetate. The combined organic layers were concentrated and the resulting residue was purified by reversed-phase prep-HPLC (water:ACN:$NH_4OH$) to afford Compound 64 (11.0 mg, 0.0235 mmol, 13.6% yield) as a yellow solid. LCMS (ESI) m/z: $[M+H]^+$=462.2. $^1$HNMR (400 MHz, DMSO-$d_6$) δ 9.35 (s, 1H), 9.00-8.99 (m, 1H), 8.61 (d, J=8.8 Hz, 1H), 8.22 (d, J=8.8 Hz, 1H), 7.92-7.91 (m, 1H), 7.76 (s, 1H), 7.56 (d, J=7.6 Hz, 1H), 7.39-7.32 (m, 2H), 7.27-7.26 (m, 1H), 6.85-6.84 (m, 1H), 6.59-6.58 (m, 1H), 4.72 (d, J=5.2 Hz, 2H), 3.91-3.88 (m, 4H), 3.58 (s, 3H), 2.35-2.32 (m, 2H).

Example 27. Preparation of Compound 65

Compound 65, shown in Table 11 below, was synthesized from 2-chloro-1,6-naphthyridine-7-carbonitrile and 2-(3-(difluoromethyl)phenyl)-4,4,5,5,-tetramethyl-1,3,2-dioxaborolane utilizing the synthetic protocol described in Example 26 above.

Step 1: Preparation of (2-chloro-1,6-naphthyridin-7-yl)methanamine

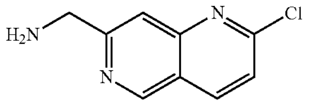 [SMILES: NCc1cc2nc(Cl)ccc2cn1]

To a cooled suspension (−78° C.) of 2-chloro-1,6-naphthyridine-7-carbonitrile (0.500 g, 2.63 mmol) in dichloromethane (21 mL) was added a solution of 1 M DIBAL-H in toluene (6.57 mL, 6.57 mmol) over 5 min. After stirring at −78° C. for 1 h, the reaction mixture was quenched with saturated aqueous potassium sodium tartrate tetrahydrate and warmed to room temperature. The mixture was diluted with 10% methanol in dichloromethane and the resulting emulsion was filtered through a Celite pad. The layers of the resulting filtrate were separated, and the aqueous layer was extracted twice with 10% methanol in dichloromethane. The solid residue and Celite were suspended in 10% methanol in dichloromethane and saturated aqueous potassium sodium tartrate tetrahydrate and stirred for 45 min. The resulting mixture was filtered via vacuum filtration and the layers of

| # | LC-MS (m/z) | $^1$H NMR |
|---|---|---|
| 65 | 457.1 | $^1$H NMR (400 MHz, DMSO-$d_6$) δ 9.41 (s, 1H), 9.02 (t, J = 6.0 Hz, 1H), 8.71 (d, J = 8.8 Hz, 1H), 8.52 (s, 1H), 8.47 (d, J = 7.2 Hz, 1H), 8.35 (d, J = 8.8 Hz, 1H), 7.93 (t, J = 2.0 Hz, 1H), 7.86-7.66 (m, 3H), 7.40-7.01 (m, 2H), 6.86-6.85 (m, 1H), 4.74 (d, J = 6.0 Hz, 2H), 3.60 (s, 3H) |

Example 28. Preparation of N-((2-(3-cyanophenyl)-1,6-naphthyridin-7-yl)methyl)-1-(methylsulfonyl)-1H-pyrrole-3-carboxamide (Compound 66)

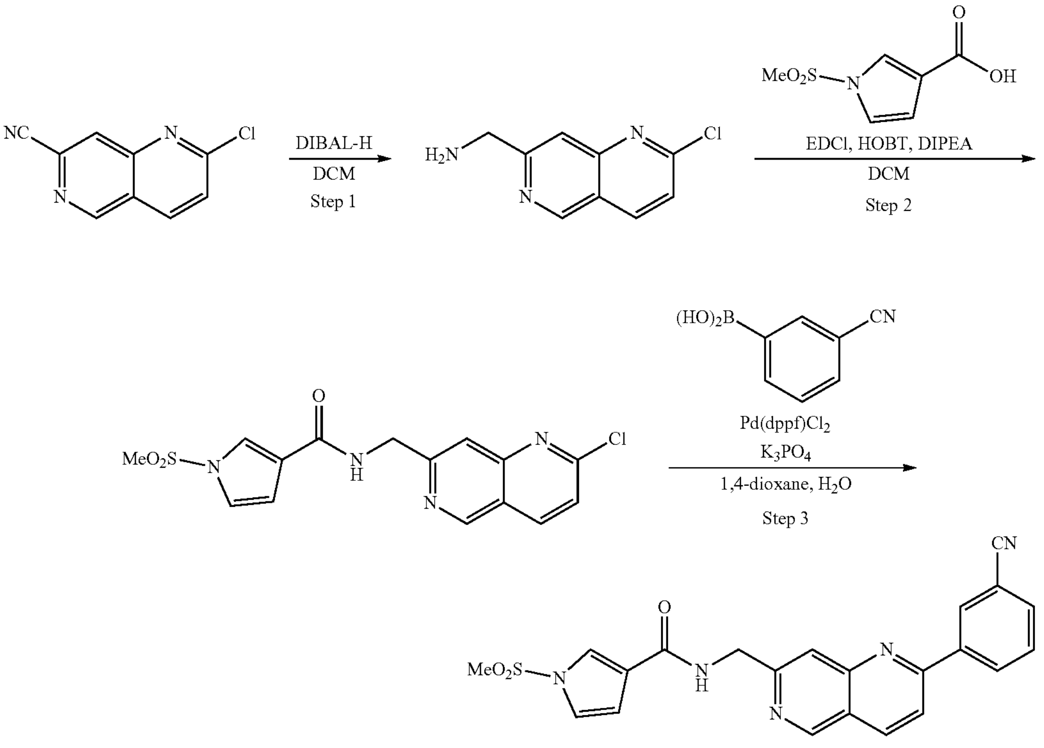

Compound 66 the resulting filtrate was extracted twice with 10% methanol in dichloromethane. The combined organic layers were washed with brine and dried with anhydrous sodium sulfate. Salts were removed via vacuum filtration and volatile materials were removed using a rotary evaporator to afford the title compound as a brown solid (513 mg, 2.64 mmol, quantitative yield), which was used without further purification. LCMS (ESI) m/z: $[M+H]^+$=194.1.

Step 2: Preparation of N-((2-chloro-1,6-naphthyridin-7-yl)methyl)-1-(methylsulfonyl)-1H-pyrrole-3-carboxamide

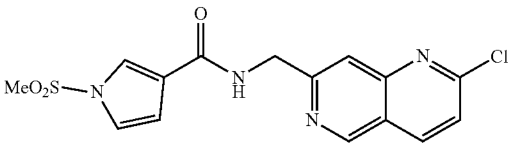 [SMILES: CS(=O)(=O)n1ccc(C(=O)NCc2cc3nc(Cl)ccc3cn2)c1]

To a suspension of (2-chloro-1,6-naphthyridin-7-yl)methanamine (512 mg, 2.64 mmol) and 1-(methylsulfonyl)-1H-pyrrole-3-carboxylic acid (548 mg, 2.90 mmol) in dichloromethane (13.2 mL) was added DIPEA (1.81 mL, 10.5 mmol) followed by 1-hydroxybenzotriazole hydrate (426 mg, 3.16 mmol) and N-(3-dimethylaminopropyl)-N'-ethylcarbodiimide hydrochloride (612 mg, 3.16 mmol). After stirring at room temperature for 3 days, the mixture was diluted with water and ethyl acetate. The layers were separated, and the aqueous layer was extracted twice with ethyl acetate. The combined organic layers were washed with brine and dried with anhydrous sodium sulfate. Salts were removed via vacuum filtration and volatile materials were removed using a rotary evaporator. The resulting mixture was purified via silica gel flash chromatography (0% to 5% MeOH in DCM and 99:0:1 to 96:3:1 DCM:MeOH:TEA) to afford the title compound (342 mg, 0.937 mmol, 35.5% yield, 67% purity) as an orange/beige solid. LCMS (ESI) m/z: $[M+H]^+$=365.0

Step 3: Preparation of N-((2-(3-cyanophenyl)-1,6-naphthyridin-7-yl)methyl)-1-(methylsulfonyl)-1H-pyrrole-3-carboxamide (Compound 66)

Compound 66

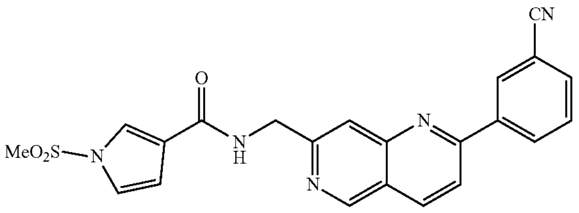

In a vial were combined N-((2-chloro-1,6-naphthyridin-7-yl)methyl)-1-(methylsulfonyl)-1H-pyrrole-3-carboxamide (45 mg, 0.123 mmol), 3-cyanophenylboronic acid (27 mg, 0.184 mmol), potassium phosphate (78.3 mg, 0.369 mmol) and [1,1'-bis(diphenylphosphino)ferrocene]dichloropalladium (17.8 mg, 0.0245 μmol). The vial was purged with nitrogen and sealed with PTFE lined septum. To the resulting mixture was added 1,4-dioxane (1.1 mL) and water (0.3 mL) and heated to 80° C. After 1 h, the reaction mixture was cooled to room temperature and diluted with water and ethyl acetate. The layers were separated the and aqueous layers was extracted twice with ethyl acetate. The combined organic layers were washed with brine and the resulting emulsion was filtered through a Celite plug. The layers were separated the and organic layer was dried with anhydrous sodium sulfate. Salts were removed via vacuum filtration and volatile materials were removed using a rotary evaporator. The resulting residue was purified via automated silica gel flash chromatography (0% to 4% MeOH in DCM) and by reversed-phase prep-HPLC to afford Compound 66 (12.4 mg, 0.0288 mmol, 23.5% yield) as a white powder. LCMS (ESI) m/z: $[M+H]^+$=432.3. $^1$H NMR (500 MHz, DMSO-$d_6$) δ 9.41 (d, J=0.9 Hz, 1H), 9.02 (t, J=6.0 Hz, 1H), 8.76-8.70 (m, 2H), 8.65 (dt, J=8.0, 1.5 Hz, 1H), 8.39 (d, J=8.6 Hz, 1H), 8.02 (dt, J=7.7, 1.4 Hz, 1H), 7.94-7.87 (m, 1H), 7.81 (t, J=0.9 Hz, 1H), 7.78 (t, J=7.8 Hz, 1H), 7.34 (dd, J=3.2, 2.3 Hz, 1H), 6.85 (dd, J=3.3, 1.7 Hz, 1H), 4.74 (d, J=5.9 Hz, 2H), 3.59 (s, 3H).

Example 29. Preparation of 1-methyl-5-(4,4,5,5-tetramethyl-1,3,2-dioxaborolan-2-yl)indoline

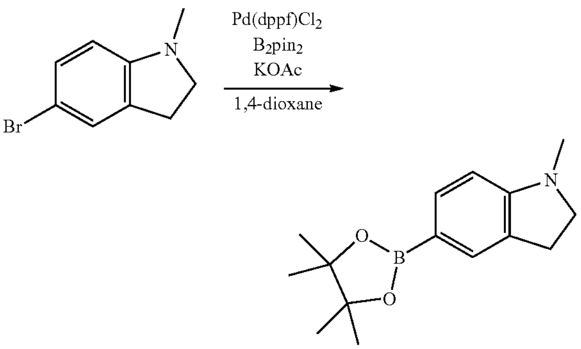

In a vial were combined 5-bromo-2,3-dihydro-1-methyl-1H-indole (90 mg, 0.424 mmol), 4,4,5,5-tetramethyl-2-(4,4,5,5-tetramethyl-1,3,2-dioxaborolan-2-yl)-1,3,2-dioxaborolane (161 mg, 0.636 mmol), potassium acetate (124 mg, 1.27 mmol) and [1,1'-bis(diphenylphosphino)ferrocene]dichloropalladium (30.8 mg, 0.0424 mmol). The vial was purged with nitrogen and sealed with PTFE lined septum. To the resulting mixture was added 1,4-dioxane (1.2 mL) and the vial was heated at 80° C. After 3 h, the reaction mixture was cooled to room temperature and diluted with water and ethyl acetate. The layers were separated, and the aqueous layers was extracted twice with ethyl acetate. The combined organic layers were washed with brine and dried with anhydrous sodium sulfate. Salts were removed via vacuum filtration and volatile materials were removed using a rotary evaporator. The resulting mixture was purified via silica gel flash chromatography (10% to 30% ethyl acetate in heptane) to afford the title compound (61.6 mg, 0.237 mmol, 56.5% yield) as a white solid. LCMS (ESI) m/z: $[M+H]^+$=260.1.

Example 30. Preparation of Compounds 67 to 72

Compounds 67 to 72, shown in Table 12 below, were each synthesized from 2-chloro-1,6-naphthyridine-7-carbonitrile and the corresponding boronic acid or boronic ester utilizing the synthetic protocol described in Example 28 above.

TABLE 12

| # | LC-MS (m/z) | $^1$H NMR |
|---|---|---|
| 67 | 449.1 | $^1$H NMR (500 MHz, DMSO-$d_6$) δ 9.29 (d, J = 0.9 Hz, 1H), 8.99 (t, J= 6.0 Hz, 1H), 8.55 (dd, J = 8.7, 0.9 Hz, 1H), 8.23 (q, J = 1.4 Hz, 1H), 8.19 (d, J = 8.7 Hz, 1H), 8.10 (dd, J = 8.4, 2.0 Hz, 1H), 7.94-7.89 (m, 1H), 7.70 (d, J = 1.0 Hz, 1H), 7.34 (dd, J = 3.2, 2.3 Hz, 1H), 6.92 (d, J = 8.4 Hz, 1H), 6.85 (dd, J = 3.3, 1.7 Hz, 1H), 4.71 (d, J = 6.0 Hz, 2H), 4.63 (t, J = 8.7 Hz, 2H), 3.59 (s, 3H), 3.28 (t, J = 8.9 Hz, 2H). |
| 68 | 449.3 | $^1$H NMR (500 MHz, DMSO-$d_6$) δ 9.34 (d, J = 0.9 Hz, 1H), 8.99 (t, J = 6.0 Hz, 1H), 8.60 (dd, J = 8.8, 0.9 Hz, 1H), 8.23 (d, J = 8.7 Hz, 1H), 7.91 (t, J = 2.0 Hz, 1H), 7.80 (dd, J = 7.7, 1.6 Hz, 1H), 7.75 (d, J = 1.0 Hz, 1H), 7.67 (d, J = 1.6 Hz, 1H), 7.40 (d, J = 7.8 Hz, 1H), 7.33 (dd, J = 3.3, 2.3 Hz, 1H), 6.85 (dd, J = 3.3, 1.7 Hz, 1H), 4.72 (d, J = 5.9 Hz, 2H), 4.60 (t, J = 8.7 Hz, 2H), 3.59 (s, 3H), 3.26 (t, J = 8.7 Hz, 2H). |
| 69 | 478.2 | $^1$H NMR (500 MHz, DMSO-$d_6$) δ 9.29 (s, 1H), 8.97 (t, J = 6.0 Hz, 1H), 8.53 (d, J = 8.7 Hz, 1H), 8.21 (d, J = 8.7 Hz, 1H), 7.91 (t, J = 2.0 Hz, 1H), 7.72 (s, 1H), 7.62 (d, J = 2.1 Hz, 1H), 7.56 (dd, J = 8.3, 2.1 Hz, 1H), 7.33 (dd, J = 3.2, 2.3 Hz, 1H), 6.84 (dd, J = 3.2, 1.7 Hz, 1H), 6.82 (d, J = 8.2 Hz, 1H), 4.71 (d, J = 5.9 Hz, 2H), 4.31 (dd, J = 5.3, 3.5 Hz, 2H), 3.58 (s, 3H), 3.31-3.27 (m, 2H), 2.96 (s, 3H). |
| 70 | 463.3 | $^1$H NMR (500 MHz, DMSO-$d_6$) δ 9.37 (d, J = 0.9 Hz, 1H), 8.99 (t, J = 6.0 Hz, 1H), 8.66-8.61 (m, 1H), 8.27 (d, J = 8.6 Hz, 1H), 7.92 (dt, J = 12.4, 2.0 Hz, 2H), 7.88 (dt, J = 7.8, 1.2 Hz, 1H), 7.78 (s, 1H), 7.49 (t, J = 7.9 Hz, 1H), 7.33 (dd, J = 3.2, 2.2 Hz, 1H), 7.24 (ddd, J = 8.3, 2.6, 0.9 Hz, 1H), 6.84 (dd, J = 3.3, 1.7 Hz, 1H), 4.73 (d, J = 5.9 Hz, 2H), 3.99 (tt, J = 6.0, 3.0 Hz, 1H), 3.58 (s, 3H), 0.88-0.79 (m, 2H), 0.74-0.63 (m, 2H). |
| 71 | 487.1 | $^1$H NMR (500 MHz, DMSO-$d_6$) δ 9.38 (d, J = 0.9 Hz, 1H), 9.01 (t, J = 6.0 Hz, 1H), 8.67 (dd, J = 8.7, 0.9 Hz, 1H), 8.43 (t, J = 1.8 Hz, 1H), 8.36 (d, J = 8.7 Hz, 1H), 8.30 (s, 1H), 8.11 (dt, J = 7.8, 1.4 Hz, 1H), 8.00 (d, J = 0.8 Hz, 1H), 7.92 (t, J = 2.0 Hz, 1H), 7.80 (s, 1H), 7.74 (dt, J = 7.8, 1.4 Hz, 1H), 7.54 (t, J = 7.7 Hz, 1H), 7.34 (dd, J = 3.3, 2.3 Hz, 1H), 6.85 (dd, J = 3.3, 1.7 Hz, 1H), 4.74 (d, J = 5.9 Hz, 2H), 3.89 (s, 3H), 3.59 (s, 3H). |
| 72 | 462.2 | $^1$H NMR (500 MHz, DMSO-$d_6$) δ 9.21 (d, J = 0.9 Hz, 1H), 8.97 (t, J = 6.0 Hz, 1H), 8.44 (dd, J = 8.9, 0.9 Hz, 1H), 8.12 (d, J = 8.8 Hz, 1H), 8.03 (d, J = 7.3 Hz, 2H), 7.91 (t, J = 2.0 Hz, 1H), 7.63 (t, J = 1.0 Hz, 1H), 7.34 (dd, J = 3.3, 2.3 Hz, 1H), 6.85 (dd, J = 3.3, 1.7 Hz, 1H), 6.58 (d, J = 9.0 Hz, 1H), 4.68 (d, J = 5.9 Hz, 2H), 3.59 (s, 3H), 3.42 (t, J = 8.4 Hz, 2H), 3.00 (t, J = 8.3 Hz, 2H), 2.81 (s, 3H). |
| 75 | 437.4 | $^1$H NMR (400 MHz, DMSO-$d_6$) δ 9.35 (s, 1H), 8.98 (t, J = 6.0 Hz, 1H), 8.53 (d, J = 8.6 Hz, 1H), 8.05 (d, J = 8.6 Hz, 1H), 7.90 (d, J = 2.3 Hz, 1H), 7.79 (dd, J = 7.4, 1.7 Hz, 1H), 7.75 (s, 1H), 7.50 (t, J = 7.6 Hz, 1H), 7.32 (t, J = 2.9 Hz, 1H), 7.22 (d, J = 8.4 Hz, 1H), 7.11 (t, J = 7.5 Hz, 1H), 6.87-6.81 (m, 1H), 4.72 (d, J = 5.9 Hz, 2H), 3.87 (s, 3H), 3.57 (s, 3H). |

Example 31. Preparation of 1-methylsulfonyl-N-[(2-phenylthiazolo[5,4-c]pyridin-6-yl)methyl]pyrrole-3-carboxamide (Compound 73)

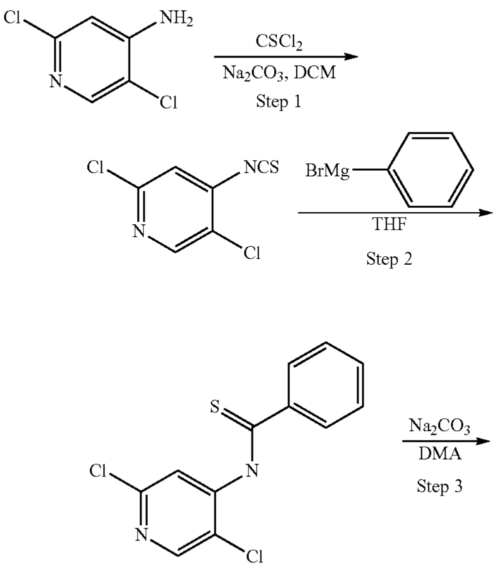

-continued

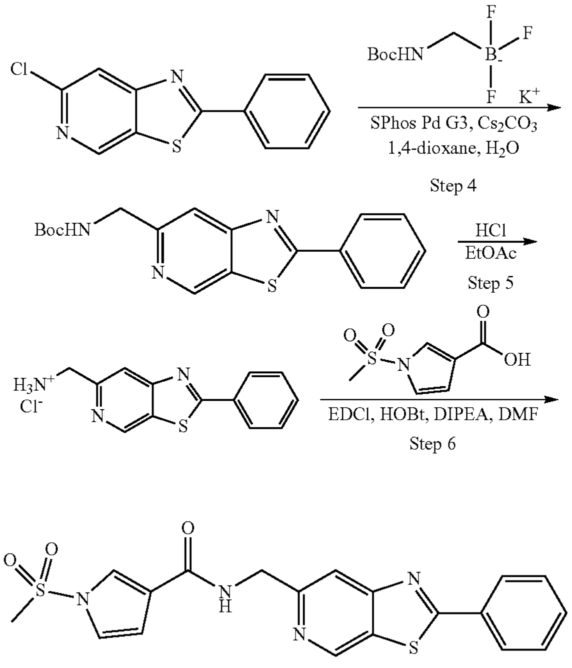

Compound 73

Step 1: Preparation of 2,5-dichloro-4-isothiocyanato-pyridine

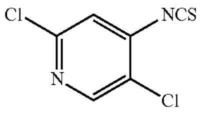

Thiocarbonyl dichloride (0.942 mL, 12.3 mmol) was added to a solution of 2,5-dichloropyridin-4-amine (1 g, 6.13 mmol) and $Na_2CO_3$ (2.60 g, 24.5 mmol) in dichloromethane (15 mL). After stirring at room temperature for 15 h, the reaction mixture was filtered, and the filtrate was concentrated to get the crude product. The residue was purified by silica gel column chromatography (petroleum ether/ethyl acetate=10/1 to 5/1) to afford the title compound (750 mg, 3.66 mmol, 59.6% yield) as a brown solid. $^1$HNMR (400 MHz, DMSO-$d_6$) δ 8.63 (s, 1H), 7.85-7.76 (m, 1H).

Step 2: Preparation of N-(2,5-dichloro-4-pyridyl)benzenecarbothioamide

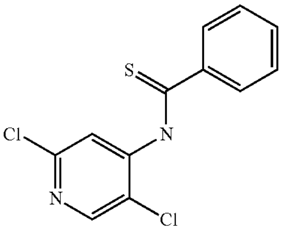 [SMILES: S=C(Nc1cc(Cl)ncc1Cl)c1ccccc1]

To a cooled mixture (−40° C.) of 2,5-dichloro-4-isothiocyanato-pyridine (650 mg, 3.17 mmol) in THE (8 mL) was added a solution of 3 M bromo(phenyl)magnesium (1.58 mL, 4.74 mmol), after addition. After stirring at −40° C. for 30 min, the reaction was warmed to room temperature. After 2 h, the mixture was added into water, and then extracted with ethyl acetate; the organic layer was washed with brine, dried over $Na_2SO_4$, filtered and concentrated to get the crude product. The residue was purified by silica gel column chromatography (petroleum ether/ethyl acetate=10/1-5/1) to afford the title compound (650 mg, 2.30 mmol, 72.4% yield) as a white solid. $^1$HNMR (400 MHz, methanol-$d_4$) δ 8.55-8.51 (m, 1H), 8.08-8.03 (m, 1H), 7.97-7.90 (m, 2H), 7.60-7.53 (m, 1H), 7.50-7.43 (m, 2H).

Step 3: Preparation of 6-chloro-2-phenyl-thiazolo[5,4-c]pyridine

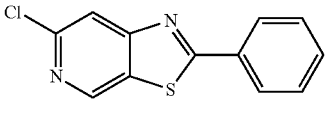 [SMILES: Clc1cc2nc(-c3ccccc3)sc2cn1]

To a mixture of N-(2,5-dichloro-4-pyridyl)benzenecarbothioamide (550 mg, 1.94 mmol) in DMA (8 mL) was added $Na_2CO_3$ (412 mg, 3.88 mmol) at room temperature. After heating at 120° C. for 3 h, the mixture was quenched with water, and then extracted three times with ethyl acetate. The combined organic layer was washed with brine, dried over $Na_2SO_4$, filtered and concentrated to get the crude product. The residue was purified by silica gel column chromatography (petroleum ether/ethyl acetate=10/1 to 5/1) to afford the title compound (250 mg, 1.01 mmol, 52.2% yield) as a yellow solid. LCMS (ESI) m/z: $[M+H]^+$=247.0. $^1$HNMR (400 MHz, DMSO-$d_6$) δ 9.25 (d, J=0.4 Hz, 1H), 8.21-8.16 (m, 3H), 7.70-7.59 (m, 3H).

Step 4: Preparation of tert-butyl N-[(2-phenylthiazolo[5,4-c]pyridin-6-yl)methyl]carbamate

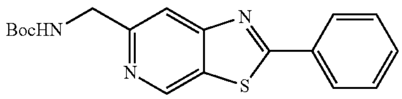 [SMILES: CC(C)(C)OC(=O)NCc1cc2nc(-c3ccccc3)sc2cn1]

To a mixture of 6-chloro-2-phenyl-thiazolo[5,4-c]pyridine (80 mg, 0.324 mmol) and potassium N-Boc-aminomethyltrifluoroborate (122 mg, 0.486 mmol) in 1,4-dioxane (3 mL) and water (0.5 mL) was added (2-dicyclohexylphosphino-2',6'-dimethoxybiphenyl) [2-(2'-amino-1,1'-biphenyl)]palladium methanesulfonate (25.3 mg, 0.0324 mmol), $Cs_2CO_3$ (211 mg, 649 μmol) at room temperature. After stirring at 100° C. for 15 h under a $N_2$ atmosphere, the mixture was filtered, and the filtrate was concentrated to give the crude product. The residue was purified by silica gel column chromatography (petroleum ether/ethyl acetate=5/1 to 3/1) to afford the title compound (60 mg, 0.176 mmol, 54.2% yield) as a white solid. LCMS (ESI) m/z: $[M+H]^+$=342.1. $^1$HNMR (400 MHz, $CDCl_3$) δ 9.13 (s, 1H), 8.15-8.13 (m, 2H), 7.94 (s, 1H), 7.62-7.49 (m, 4H), 5.50 (s, 1H), 4.62 (d, J=5.2 Hz, 2H), 1.49 (s, 9H).

Step 5: Preparation of (2-phenylthiazolo[5,4-c]pyridin-6-yl)methanaminium chloride

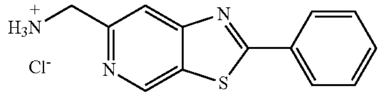 [SMILES: NCc1cc2nc(-c3ccccc3)sc2cn1 ; [Cl-]]

A mixture of tert-butyl N-[(2-phenylthiazolo[5,4-c]pyridin-6-yl)methyl]carbamate (60 mg, 0.176 mmol) in a solution of 4 M HCl in 1,4-dioxane (2 mL, 8 mmol) was stirred at room temperature. After 2 h, the mixture was concentrated to afford the title compound (30 mg, 0.108 mmol, 61.5% yield) as a white solid which was used in the next step directly. LCMS (ESI) m/z: $[M+H]^+$=242.1.

Step 6: Preparation of 1-methylsulfonyl-N-[(2-phenylthiazolo[5,4-c]pyridin-6-yl)methyl]pyrrole-3-carboxamide (Compound 73)

Compound 73

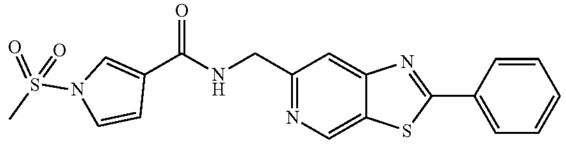

To a mixture of (2-phenylthiazolo[5,4-c]pyridin-6-yl) methanaminium chloride (15 mg, 0.0540 mmol) and 1-methylsulfonylpyrrole-3-carboxylic acid (10.2 mg, 0.0540 μmol) in DMF (1 mL) was added EDCI (20.7 mg, 0.108 mmol), HOBt (14.6 mg, 0.108 mmol) and DIPEA (0.047 mL, 0.270 mmol) at room temperature. After 15 h, water was added to the mixture, then extracted three times with ethyl acetate; the combined organic layer was washed with brine, dried over $Na_2SO_4$, filtered and concentrated to get the crude product. The crude product was purified by reversed-phase prep-HPLC (water:ACN:FA) to afford Compound 73 (1.98 mg, 0.00470 mmol, 8.71% yield) as a white solid. LCMS (ESI) m/z: $[M+H]^+$=413.0. $^1$HNMR (400 MHz, DMSO-$d_6$) δ 9.34 (d, J=0.8 Hz, 1H), 8.96-8.93 (m, 1H), 8.21-8.13 (m, 2H), 7.93-7.86 (m, 2H), 7.70-7.57 (m, 3H), 7.33-7.31 (m, 1H), 6.83-6.81 (m, 1H), 4.67 (d, J=6.0 Hz, 2H), 3.58 (s, 3H).

Example 32: Preparation of N-((2-(6-(cis-2,6-dimethylmorpholino)pyridin-2-yl)-1,6-naphthyridin-7-yl)methyl)-1-(methylsulfonyl)-1H-pyrrole-3-carboxamide (Compound 76)

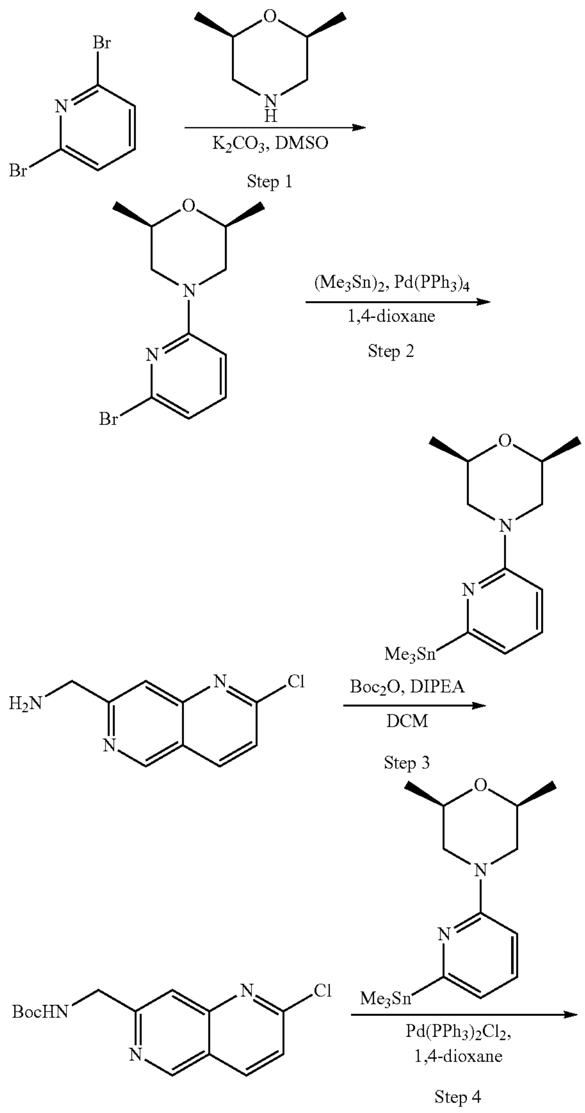

-continued

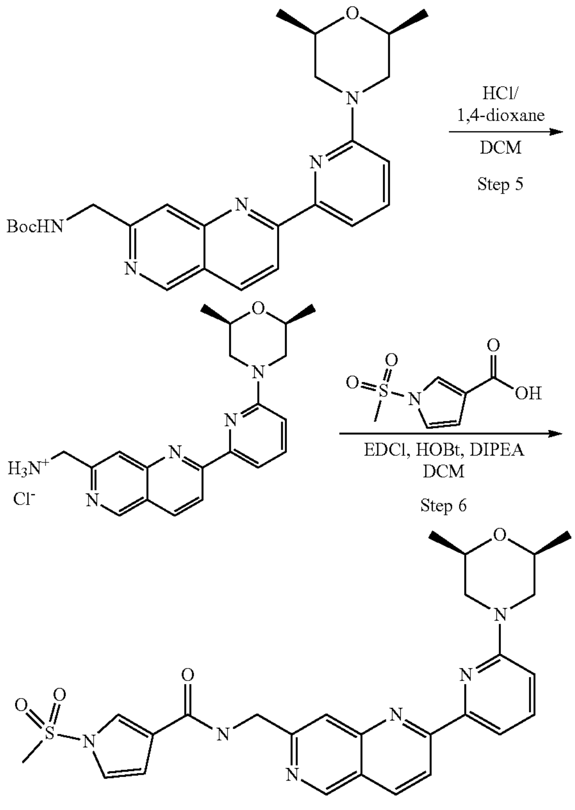

76

Step 1: Preparation of cis-4-(6-bromo-2-pyridyl)-2,6-dimethyl-morpholine

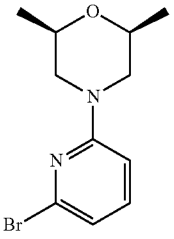

To a solution of 2,6-dibromopyridine (50 g, 211 mmol) and cis-2,6-dimethylmorpholine (36.5 g, 317 mmol) in DMSO (500 mL) was added $K_2CO_3$ (87.5 g, 633 mmol). After stirring at 80° C. for 16 h, the reaction mixture was poured into water. The solution was extracted three times with ethyl acetate. The combined organic layer was washed with brine, dried over $Na_2SO_4$, filtered and concentrated to give a residue. The residue was purified by column chromatography (petroleum ether/ethyl acetate=10/1-1/1), the solution was concentrated to give cis-4-(6-bromo-2-pyridyl)-2,6-dimethyl-morpholine (54 g, 199 mmol, 94.4% yield) as a yellow oil. $^1$H NMR (400 MHz, DMSO-$d_6$) δ 7.31-7.27 (m, 1H), 6.76 (d, J=7.6 Hz, 1H), 6.50 (d, J=8.0 Hz, 1H), 4.03-3.99 (m, 2H), 3.69-3.66 (m, 2H), 2.55-2.49 (m, 2H), 1.28-1.25 (m, 6H).

Step 2: Preparation of [6-[cis-2,6-dimethylmorpholin-4-yl]-2-pyridyl]-trimethyl-stannane

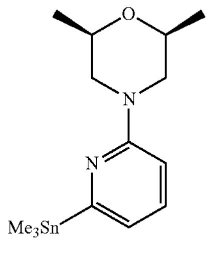

To a solution of cis-4-(6-bromo-2-pyridyl)-2,6-dimethylmorpholine (20 g, 73.8 mmol) and trimethyl(trimethylstannyl)stannane (29.0 g, 88.5 mmol) in 1,4-dioxane (200 mL) was added $Pd(PPh_3)_4$ (4.26 g, 3.69 mmol). The mixture was stirred at 100° C. for 2 h under a $N_2$ atmosphere. The reaction mixture was poured into water and the resulting solution was extracted three times with ethyl acetate. The combined organic layer was washed with brine, dried over $Na_2SO_4$, filtered and concentrated to give [6-[cis-2,6-dimethylmorpholin-4-yl]-2-pyridyl]-trimethyl-stannane (26.1 g, crude) as a brown oil, which was used for the next step directly.

Step 3: Preparation of tert-butyl N-[(2-chloro-1,6-naphthyridin-7-yl)methyl]carbamate

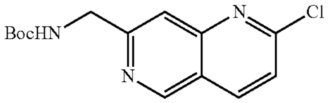 [SMILES: CC(C)(C)OC(=O)NCc1cc2nc(Cl)ccc2cn1]

To a solution of (2-chloro-1,6-naphthyridin-7-yl)methanamine (51 g, 263 mmol) in DCM (1500 mL) was added $(Boc)_2O$ (172 g, 790 mmol) and DIPEA (102 g, 790 mmol). The mixture was stirred at 25° C. for 16 h. The reaction mixture was diluted with water and then filtered. The filtrate was extracted with three times with DCM. The combined organic layers were washed with brine, dried over $Na_2SO_4$, filtered and concentrated under reduced pressure. The residue was purified by silica gel column chromatography (petroleum ether/ethyl acetate=10/1 to 2/1 to 1/3) to afford tert-butyl N-[(2-chloro-1,6-naphthyridin-7-yl)methyl]carbamate (21 g, 64.3 mmol, 24.4% yield) as a light yellow solid. LCMS (ESI) m/z: $[M+H]^+$=293.9. $^1H$ NMR (400 MHz, DMSO-$d_6$) δ 9.37 (s, 1H), 8.62 (d, J=8.4 Hz, 1H), 7.71 (d, J=8.4 Hz, 1H), 7.58-7.53 (m, 2H), 4.39 (d, J=6.4 Hz, 2H), 4.20-4.25 (m, 2H), 1.41 (s, 9H).

Step 4: Preparation of tert-butyl N-[[2-[6-[(2S,6R)-2,6-dimethylmorpholin-4-yl]-2-pyridyl]-1,6-naphthyridin-7-yl]methyl]carbamate

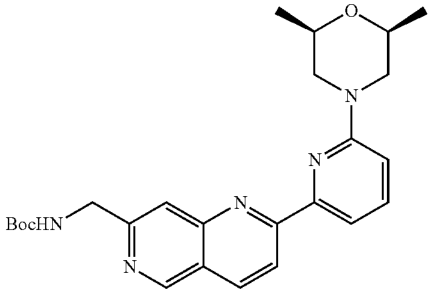 [SMILES: C[C@@H]1CN(c2cccc(-c3ccc4cnc(CNC(=O)OC(C)(C)C)cc4n3)n2)C[C@H](C)O1]

A mixture of [6-[cis-2,6-dimethylmorpholin-4-yl]-2-pyridyl]-trimethyl-stannane (26 g, 73.2 mmol) and tert-butyl N-[(2-chloro-1,6-naphthyridin-7-yl)methyl]carbamate (10.8 g, 36.6 mmol) in 1,4-dioxane (120 mL) was added $Pd(PPh_3)_2Cl_2$ (2.57 g, 3.66 mmol) was stirred at 100° C. for 2 h under a $N_2$ atmosphere. The reaction mixture was concentrated to give a residue. The residue was purified by silica gel column chromatography (petroleum ether/ethyl acetate=1:1-0:1) to afford N-[[2-[6-[(2S,6R)-2,6-dimethylmorpholin-4-yl]-2-pyridyl]-1,6-naphthyridin-7-yl]methyl]carbamate (15 g, 32.8 mmol, 89.5% yield) as a yellow solid. LCMS (ESI) m/z: $[M+H]^+$=450.2. $^1H$ NMR (400 MHz, DMSO-$d_6$) δ 9.35 (s, 1H), 8.66-8.59 (m, 2H), 7.93 (d, J=7.2 Hz, 1H), 7.79-7.74 (m, 2H), 7.62 (7.63-7.61, 1H), 7.04 (d, J=8.4 Hz, 1H), 4.45 (br d, J=6.0 Hz, 2H), 4.32 (br d, J=11.2 Hz, 2H), 3.69-3.65 (m, 2H), 2.52 (br s, 2H), 1.44-1.36 (m, 9H), 1.22 (d, J=6.0 Hz, 6H)

Step 5: Preparation of (2-(6-(cis-2,6-dimethylmorpholino)pyridin-2-yl)-1,6-naphthyridin-7-yl)methanaminium chloride

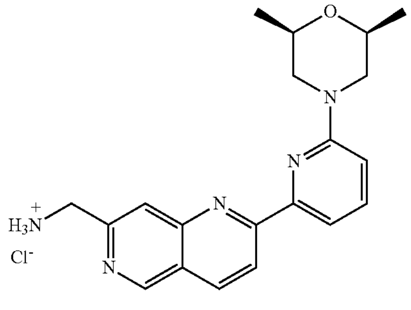 [SMILES: [Cl-] ; C[C@@H]1CN(c2cccc(-c3ccc4cnc(CN)cc4n3)n2)C[C@H](C)O1]

To a solution of HCl (4 M in 1,4-dioxane, 200 mL) was added a solution of N-[[2-[6-[(2S,6R)-2,6-dimethylmorpholin-4-yl]-2-pyridyl]-1,6-naphthyridin-7-yl]methyl]carbamate (15 g, 33.4 mmol) in DCM (200 mL). The mixture was stirred at 30° C. for 2 h. The reaction mixture was concentrated and the resulting residue was poured into MTBE. The solution was filtered and the filter cake was dried in vacuum to give (2-(6-(cis-2,6-dimethylmorpholino)pyridin-2-yl)-1,6-naphthyridin-7-yl)methanaminium chloride (15.5 g, crude) as a yellow solid. LCMS (ESI) m/z: $[M+H]^+$=350.1. $^1$H NMR (400 MHz, DMSO-$d_6$) δ 9.56 (s, 1H), 8.82-8.70 (m, 5H), 8.21 (s, 1H), 7.94 (d, J=7.6 Hz, 1H), 7.82-7.78 (m, 1H), 7.08 (d, J=8.4 Hz, 1H), 4.42-4.31 (m, 4H), 3.70-3.65 (m, 2H), 2.54-2.52 (m, 2H), 1.22-1.16 (m, 6H).

Step 6: preparation of N-((2-(6-(cis-2,6-dimethylmorpholino)pyridin-2-yl)-1,6-naphthyridin-7-yl)methyl)-1-(methylsulfonyl)-1H-pyrrole-3-carboxamide (Compound 76)

76

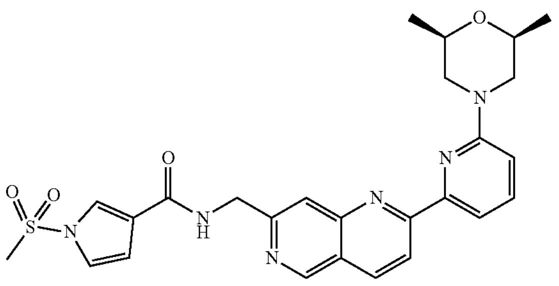

To a solution of 1-methylsulfonylpyrrole-3-carboxylic acid (17.1 mg, 0.0906 mmol) and (2-(6-(cis-2,6-dimethylmorpholino)pyridin-2-yl)-1,6-naphthyridin-7-yl)methanaminium chloride (35.0 mg, 0.0906 mmol) in DCM (0.36 mL) was added DIPEA (0.079 mL, 0.453 mmol) followed by EDCI (20.7 mg, 0.108 mmol) and HOBt (14.5 mg, 0108 mmol). The resulting mixture was stirred overnight at room temperature. The mixture was dilute with water and ethyl acetate. The layers were separated and the aqueous layer was extracted twice with ethyl acetate. The combined organic layers were washed with brine, dried over $Na_2SO_4$, filtered and concentrated under reduced pressure to give a residue. The residue was purified by C18 prep-HPLC ($H_2O$:ACN: FA) to give compound 76 (14.3 mg, 0.0274 mmol, 30.1% yield) as a yellow powder. LCMS (ESI) m/z: $[M+H]^+$ =521.3. $^1$H NMR (400 MHz, DMSO-$d_6$) δ 9.38 (d, J=1.0 Hz, 1H), 8.99 (t, J=6.0 Hz, 1H), 8.70-8.58 (m, 2H), 7.92 (dt, J=4.8, 2.2 Hz, 2H), 7.81-7.71 (m, 2H), 7.34 (td, J=2.8, 2.2, 1.2 Hz, 1H), 7.03 (d, J=8.5 Hz, 1H), 6.85 (dt, J=3.1, 1.4 Hz, 1H), 4.73 (d, J=5.9 Hz, 2H), 4.31 (dt, J=12.7, 1.7 Hz, 2H), 3.74-3.62 (m, 2H), 3.59 (s, 3H), 2.63-2.40 (m, 2H), 1.22 (d, J=6.3 Hz, 6H).

Example 33. Preparation of Compounds of the Invention

The compounds in Table 13 below were synthesized starting from the appropriate common intermediate (2-(6-(cis-2,6-dimethylmorpholino)pyridin-2-yl)-1,6-naphthyridin-7-yl)methanaminium chloride and corresponding carboxylic acid utilizing the synthetic protocol described in Example 32.

TABLE 13

| # | LC-MS (m/z) | $^1$H NMR |
|---|---|---|
| 77 | 499.4 | $^1$H NMR (400 MHz, DMSO-$d_6$) δ 9.37 (s, 1H), 8.69-8.58 (m, 2H), 8.53 (t, J = 6.0 Hz, 1H), 7.91 (d, J = 7.7 Hz, 1H), 7.77-7.68 (m, 2H), 7.58 (t, J = 2.0 Hz, 1H), 7.07-6.96 (m, 2H), 6.57 (dt, J = 2.9, 1.4 Hz, 1H), 4.70 (d, J = 6.0 Hz, 2H), 4.31 (d, J = 13.1 Hz, 2H), 3.74-3.62 (m, 2H), 2.57-2.43 (m, 2H), 1.51 (s, 9H), 1.21 (d, J = 6.2 Hz, 6H) |
| 78 | 500.3 | $^1$H NMR (400 MHz, DMSO-$d_6$) δ 9.38 (s, 1H), 8.75 (t, J = 6.1 Hz, 1H), 8.69-8.58 (m, 2H), 7.96 (dd, J = 2.4, 0.9 Hz, 1H), 7.91 (d, J = 7.4 Hz, 1H), 7.78-7.70 (m, 2H), 7.03 (d, J = 8.5 Hz, 1H), 6.72-6.66 (m, 1H), 4.75 (d, J = 6.1 Hz, 2H), 4.31 (d, J = 11.2 Hz, 2H), 3.74-3.63 (m, 2H), 2.61-2.40 (m, 2H), 1.60 (s, 9H), 1.22 (d, J = 6.1 Hz, 6H) |
| 79 | 511.4 | $^1$H NMR (400 MHz, DMSO-$d_6$) δ 9.39 (s, 1H), 8.95 (t, J = 6.1 Hz, 1H), 8.70-8.59 (m, 2H), 8.18 (dd, J = 2.6, 0.9 Hz, 1H), 7.91 (d, J = 7.4 Hz, 1H), 7.77 (s, 1H), 7.75 (d, J = 8.0 Hz, 1H), 7.03 (d, J = 8.5 Hz, 1H), 6.85 (dd, J = 2.6, 0.9 Hz, 1H), 4.77 (d, J = 6.0 Hz, 2H), 4.31 (d, J = 12.5 Hz, 2H), 3.74-3.60 (m, 2H), 2.56-2.45 (m, 2H), 2.06 (s, 6H), 1.22 (d, J = 6.2 Hz, 6H) |
| 82* | 565.3 | $^1$H NMR (400 MHz, DMSO-$d_6$) δ 9.40 (s, 1H), 8.76 (d, J = 8.2 Hz, 1H), 8.70-8.58 (m, 2H), 8.46 (br d, J = 3.1 Hz, 1H), 8.04 (t, J = 2.0 Hz, 1H), 7.99-7.85 (m, 2H), 7.80-7.68 (m, 1H), 7.31 (dd, J = 2.3, 3.2 Hz, 1H), 7.04 (d, J = 8.4 Hz, 1H), 6.84 (dd, J = 1.7, 3.2 Hz, 1 H), 5.60-5.44 (m, 1H), 4.32 (br d, J = 11.2 Hz, 2H), 3.94-3.81 (m, 2H), 3.68 (ddd, J = 2.3, 6.2, 10.3 Hz, 2H), 3.58 (s, 3H), 3.32 (s, 3H), 2.53 (br d, J = 2.9 Hz, 2H), 1.21 (d, J = 6.2 Hz, 6H) |

*formate salt of compound 82

Example 34: Preparation of N-[[2-(6-cyclopropylpyrazin-2-yl)-1,6-naphthyridin-7-yl]methyl]-1-methylsulfonyl-pyrrole-3-carboxamide (Compound 80)

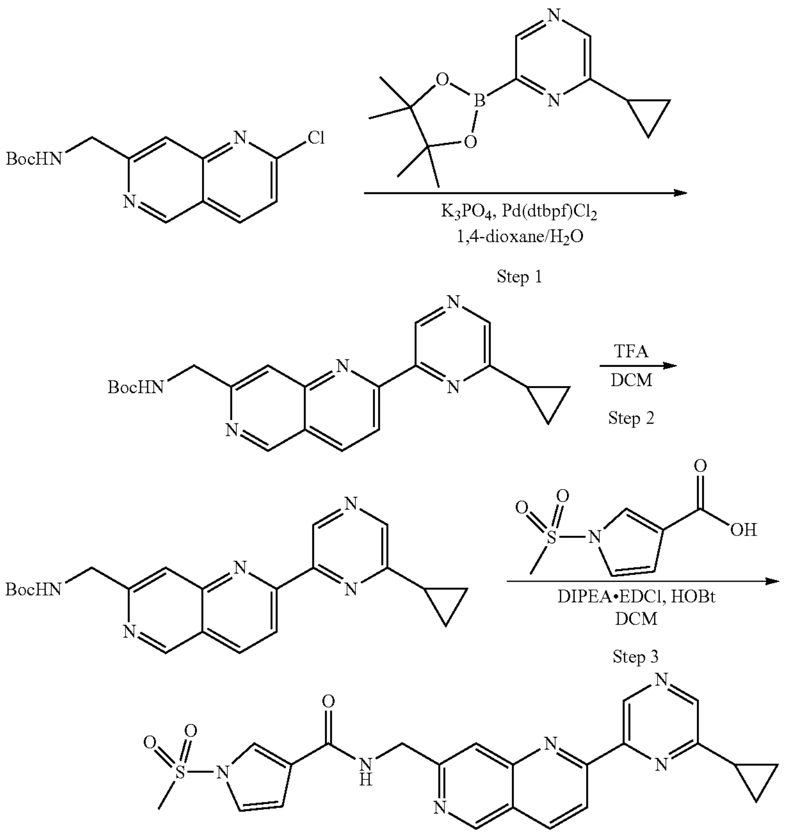

80

Step 1: Preparation of tert-butyl N-[[2-(6-cyclopropylpyrazin-2-yl)-1,6-naphthyridin-7-yl]methyl]carbamate

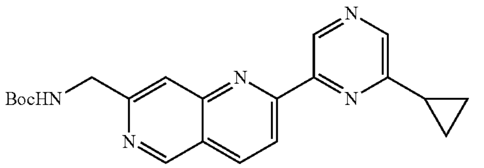 [SMILES: CC(C)(C)OC(=O)NCc1cc2nc(-c3cncc(C4CC4)n3)ccc2cn1]

To a solution of tert-butyl N-[(2-chloro-1,6-naphthyridin-7-yl)methyl]carbamate (270 mg, 0.919 mmol) and 2-cyclopropyl-6-(4,4,5,5-tetramethyl-1,3,2-dioxaborolan-2-yl) pyrazine (679 mg, 2.76 mmol) in 1,4-dioxane/$H_2O$ (4/1, 5 mL) was added $K_3PO_4$ (585 mg, 2.76 mmol) and Pd(dtbpf) $Cl_2$ (59.9 mg, 0.0919 mmol) at 25° C. The mixture was stirred at 80° C. for 2 h under a $N_2$ atmosphere. The reaction mixture was diluted with $H_2O$ and extracted twice with DCM. The combined organic layers were dried over anhydrous $Na_2SO_4$, filtered and concentrated to afford the residue. The residue was purified by silica gel column chromatography (Petroleum ether/Ethyl acetate, 1/0 to 0/1) to afford tert-butyl N-[[2-(6-cyclopropylpyrazin-2-yl)-1,6-naphthyridin-7-yl]methyl]carbamate (210 mg, 0.0556 mmol, 60.5% yield) as a yellow solid. LCMS (ESI) m/z: $[M+H]^+$=378.2. $^1H$ NMR (400 MHz, $CDCl_3$) δ 9.60 (s, 1H), 9.25 (s, 1H), 8.60 (s, 1H), 8.58 (d, J=8.8 Hz, 1H), 8.38 (d, J=8.4 Hz, 1H), 7.96 (s, 1H), 4.69 (d, J=5.6 Hz, 2H), 2.21-2.17 (m, 1H), 1.24 (s, 9H), 1.23-1.22 (m, 2H), 1.18-1.15 (m, 2H).

Step 2: Preparation of Intermediate 8 [2-(6-cyclopropylpyrazin-2-yl)-1,6-naphthyridin-7-yl]methanamine

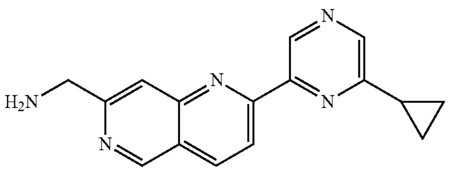 [SMILES: NCc1cc2nc(-c3cncc(C4CC4)n3)ccc2cn1]

To a solution of tert-butyl N-[[2-(6-cyclopropylpyrazin-2-yl)-1,6-naphthyridin-7-yl]methyl]carbamate (210 mg, 0.556 mmol) in DCM (3 mL) was added TFA (0.6 mL, 8.10 mmol). The mixture was stirred at 25° C. for 1 h. To the reaction mixture was added to sat. aqueous $NaHCO_3$ and the mixture was extracted twice with DCM. The combined organic layers were dried over anhydrous $Na_2SO_4$, filtered and concentrated to afford the product [2-(6-cyclopropylpyrazin-2-yl)-1,6-naphthyridin-7-yl]methanamine (130 mg, 0.469 mmol, 84.3% yield) as a yellow solid which was used directly in the next step. LCMS (ESI) m/z: $[M+H]^+$=278.3.

Step 3: Preparation of N-[[2-(6-cyclopropylpyrazin-2-yl)-1,6-naphthyridin-7-yl]methyl]-1-methylsulfonyl-pyrrole-3-carboxamide (Compound 80)

80

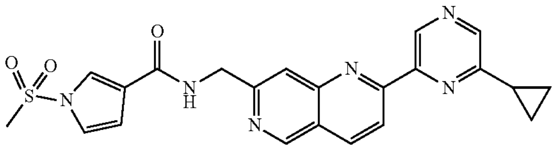

To a mixture of 1-(methylsulfonyl)-1H-pyrrole-3-carboxylic acid (20.5 mg, 0.108 mmol) and [2-(6-cyclopropylpyrazin-2-yl)-1,6-naphthyridin-7-yl]methanamine (25 mg, 0.0902 mmol) in DCM (1 mL) was added DIPEA (46.60 mg, 0.361 mmol), EDCI (25.92 mg, 0.135 mmol), and HOBt (18.27 mg, 0.135 mmol). The mixture was stirred at 25° C. for 1 h. The mixture was poured into water and extracted three times with ethyl acetate. The combined organics were washed with brine, dried over anhydrous $Na_2SO_4$, and filtered; the filtrate was evaporated to dryness. The residue was purified by prep-HPLC to afford compound 80 (30.9 mg, 0.0647 mmol, 71.8% yield) as a yellow solid. LCMS (ESI) m/z $[M+H]^+$=449.2. $^1$H NMR (400 MHz, DMSO-$d_6$) δ 9.45-9.43 (m, 2H), 9.04-9.01 (m, 1H), 8.78 (s, 1H), 8.74 (d, J=8.0 Hz, 1H), 8.55 (d, J=8.4 Hz, 1H), 7.92-7.91 (m, 1H), 7.83 (s, 1H), 7.34-7.33 (m, 1H), 6.85-6.84 (m, 1H), 4.74 (d, J=5.6 Hz, 2H), 3.60-3.59 (m, 3H), 2.38-2.34 (m, 1H), 1.16-1.14 (m, 4H).

Example 35. Preparation of 1-(1-cyano-1-methyl-ethyl)imidazole-4-carboxylic acid

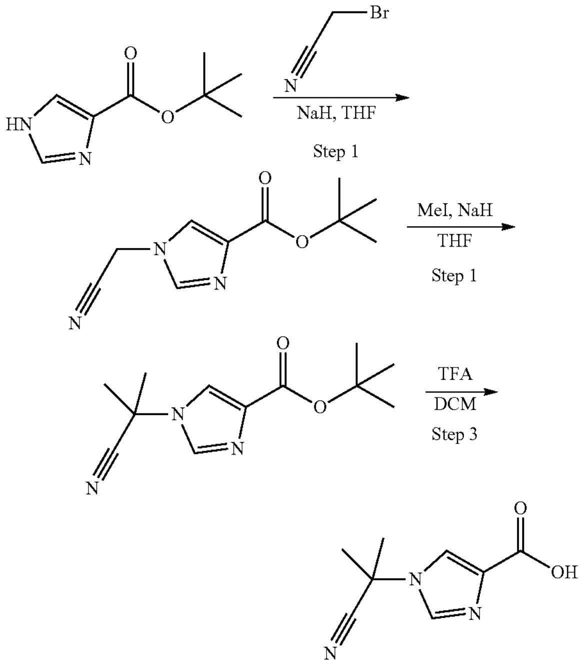

Step 1: Preparation of tert-butyl 1-(cyanomethyl)imidazole-4-carboxylate

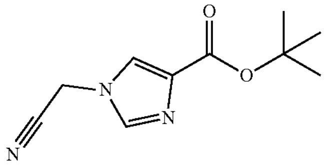

To a cooled (15° C.) solution of tert-butyl 1H-imidazole-5-carboxylate (0.550 g, 3.27 mmol) in THE (10 mL) was added NaH (0.157 g, 3.92 mmol, 60% purity). After 30 min, 2-bromoacetonitrile (0.262 mL, 3.92 mmol) was added. The mixture was warmed to room temperature and stirred for 2 h. The reaction was diluted with water and extracted three times with ethyl acetate. The combined the organic layers were dried over $Na_2SO_4$, filtered and concentrated. The residue was purified by silica gel column chromatography (petroleum ether/ethyl acetate=10/1 to 3/1) to give tert-butyl 1-(cyanomethyl)imidazole-4-carboxylate (0.520 g, 2.51 mmol, 76.7% yield) as a yellow solid. $^1$H NMR (400 MHz, $CDCl_3$) δ 7.64-7.61 (m, 2H), 5.03-5.00 (m, 2H), 1.58 (s, 9H).

Step 2: Preparation of tert-butyl 1-(1-cyano-1-methyl-ethyl)imidazole-4-carboxylate

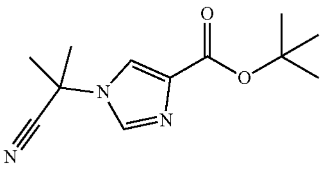 [SMILES: CC(C)(C)OC(=O)c1cn(C(C)(C)C#N)cn1]

To a cooled (0° C.) solution of tert-butyl 1-(cyanomethyl) imidazole-4-carboxylate (0.400 g, 1.93 mmol) in THE (8 mL) was added NaH (0.386 g, 9.65 mmol, 60% purity) in portion. The mixture was stirred at 25° C. for 1 h, followed by addition of MeI (0.721 mL, 11.6 mmol). After 12 h, the reaction was slowly poured into saturated aqueous $NH_4Cl$ and extracted three times with ethyl acetate. The combined the organic layers were dried over $Na_2SO_4$, filtered, and concentrated. The residue was purified by silica gel column chromatography (petroleum ether/ethyl acetate=10/1 to 1/1) to give tert-butyl 1-(1-cyano-1-methyl-ethyl)imidazole-4-carboxylate (0.100 g, 0.397 mmol, 20.5% yield) as a yellow solid. LCMS (ESI) m/z: $[M+H]^+$=236.1; $^1$H NMR (400 MHz, $CDCl_3$) δ 7.71-7.64 (m, 2H), 1.94 (s, 6H), 1.52 (s, 9H).

Step 3: Preparation of 1-(1-cyano-1-methyl-ethyl)imidazole-4-carboxylic acid

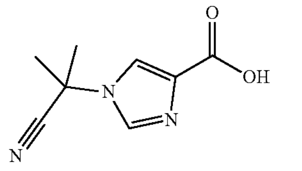

To a solution of tert-butyl 1-(1-cyano-1-methyl-ethyl) imidazole-4-carboxylate (0.050 g, 0.213 mmol) in dichloromethane (0.7 mL) was added TFA (0.157 mL, 2.13 mmol) and stirred at for 2 h. The mixture was concentrated to afford 1-(1-cyano-1-methyl-ethyl)imidazole-4-carboxylic acid (0.034 g, 0.190 mmol, 89.29% yield) as a yellow solid which was used into the next step without further purification. LCMS (ESI) m/z: $[M+H]^+$=180.0.

Example 36: Preparation of 1-(2-cyanopropan-2-yl)-N-((2-phenyl-1,6-naphthyridin-7-yl)methyl)-1H-imidazole-4-carboxamide (Compound 81)

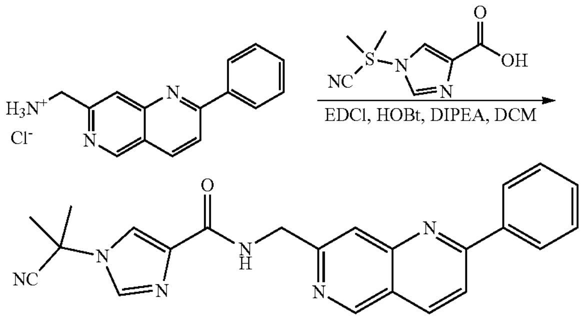

81

Compound 81 was prepared according the procedure in example 34 beginning with (2-phenyl-1,6-naphthyridin-7-yl)methanaminium chloride and 1-(1-cyano-1-methyl-ethyl) imidazole-4-carboxylic acid to afford compound 81. LCMS (ESI) m/z: $[M+H]^+$=397.2. $^1$H NMR (400 MHz, DMSO-$d_6$) δ 9.36 (s, 1H), 8.86 (t, J=6.2 Hz, 1H), 8.64 (d, J=8.6 Hz, 1H), 8.33-8.22 (m, 3H), 8.14 (dd, J=17.6, 1.5 Hz, 2H), 7.73 (d, J=1.2 Hz, 1H), 7.56 (dd, J=5.2, 1.9 Hz, 3H), 4.75 (d, J=6.2 Hz, 2H), 2.04 (s, 6H).

Example 37: Preparation of 1-(1-cyano-1-methyl-ethyl)pyrazole-3-carboxylic acid

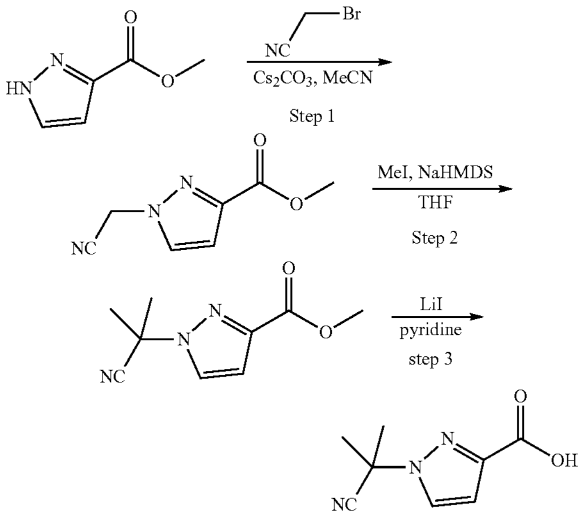

Step 1: Preparation of 3 methyl 1-(cyanomethyl)pyrazole-3-carboxylate

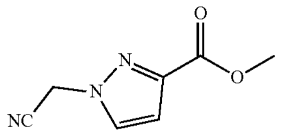

To a solution of methyl 1H-pyrazole-3-carboxylate (50 g, 396 mmol) in MeCN (500 mL) was added bromoacetonitrile (39.6 mL, 595 mmol) and $Cs_2CO_3$ (194 g, 595 mmol). The reaction mixture was stirred at 60° C. for 2 h under a $N_2$ atmosphere. The reaction mixture was diluted with water and extracted three times with ethyl acetate. The combined organic layers were washed with brine, dried over $Na_2SO_4$, filtered, and concentrated in vacuum. The residue was purified by silica gel column chromatography (Petroleum ether/Ethyl acetate=20/1 to 1/1) to give 3 methyl 1-(cyanomethyl) pyrazole-3-carboxylate (30 g, 180 mmol, 45.4% yield) as a yellow solid. LCMS (ESI) m/z: $[M+H]^+$=166.0. $^1$H NMR (400 MHz, DMSO-$d_6$) δ 8.00 (d, J=2.4 Hz, 1H), 6.83 (d, J=2.4 Hz, 1H), 5.60 (s, 2H), 3.81 (s, 3H).

Step 2: Preparation of methyl 1-(1-cyano-1-methyl-ethyl)pyrazole-3-carboxylate

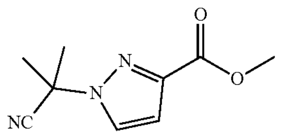

To a solution of 3 methyl 1-(cyanomethyl)pyrazole-3-carboxylate (12 g, 72.7 mmol) and MeI (27.1 mL, 436 mmol) in THE (150 mL) was added NaHMDS (1 M, 291 mL, 291 mmol) in 0° C. The reaction mixture was stirred at 25° C. for 2 h under a $N_2$ atmostphere. The reaction mixture was quenched with saturated aq. $NH_4Cl$ and extracted three times with ethyl acetate. The organic layer was concentrated under vacuum. The residue was purified by silica gel flash chromatography (Ethyl acetate/Petroleum ether, 0-50%) to afford methyl 1-(1-cyano-1-methyl-ethyl)pyrazole-3-carboxylate (3 g, 14.3 mmol, 19.7% yield) as a yellow oil. LCMS (ESI) m/z: $[M+H]^+$=194.2. $^1$H NMR (400 MHz, DMSO-$d_6$) δ 8.19 (d, J=2.8 Hz, 1H), 6.89 (d, J=2.8 Hz, 1H), 3.82 (s, 3H), 2.00 (s, 6H).

Step 3: Preparation of 1-(1-cyano-1-methyl-ethyl)pyrazole-3-carboxylic acid

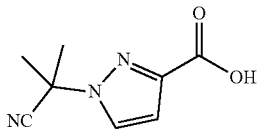

To a solution of methyl 1-(1-cyano-1-methyl-ethyl)pyrazole-3-carboxylate (2 g, 10.4 mmol) in pyridine (20 mL)

was added LiI (13.9 g, 104 mmol) at 25° C. The reaction was stirred at 135° C. for 12 h under a $N_2$ atmosphere. The mixture was concentrated under vacuum. The residue was washed with water and extracted three times with ethyl acetate. The aqueous phase was adjusted to pH-3 by 1 M HCl solution and extracted three times with ethyl acetate. The combined organic phase was dried with anhydrous $Na_2SO_4$, filtered and concentrated in vacuum to afford 1-(1-cyano-1-methyl-ethyl)pyrazole-3-carboxylic acid (1.2 g, crude) as a yellow solid. LCMS (ESI) m/z: $[M+H]^+$= 180.1. $^1H$ NMR (400 MHz, DMSO-$d_6$) δ 12.96 (br s, 1H), 8.14 (s, 1H), 6.82 (s, 1H), 2.00 (s, 6H).

Example 38. Assay for ATPase Catalytic Activity of BRM and BRG-1

The ATPase catalytic activity of BRM or BRG-1 was measured by an in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 μL) contains 30 nM of BRM or BRG-1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM $MgCl_2$, 50 mM NaCl, 0.1% Tween-20, and 1 mM fresh DTT (Pierce™ DTT (Dithiothreitol), cat #20290). The reaction is initiated by the addition of the 2.5 μL ATPase solution to 2.5 μL ATP/DNA solution on low volume white Proxiplate-384 plus plate (PerkinElmer, cat #6008280) and incubates at room temperature for 1 hour. Then following addition of 5 μL of ADP-Glo™ Reagent provided in the kit, the reaction incubates at room temperature for 40 minutes. Then 10 μL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG-1 were synthesized from High Five insect cell lines with a purity of greater than 90%. $IC_{50}$ data for Compounds 1-83 from the ATPase catalytic activity assay described herein are shown in Table 14 below.

TABLE 14

BRM and BRG-1 Inhibition Data for Compounds of the Invention

| Compound # | BRM ATPase: $IC_{50}$ (μM) | BRG1 ATPase: $IC_{50}$ (μM) |
|---|---|---|
| 1 | ++ | ++ |
| 2 | +++ | +++ |
| 3 | +++ | ++ |
| 4 | +++ | +++ |
| 5 | ++ | ++ |
| 6 | ++ | ++ |
| 7 | ++ | ++ |
| 8 | +++ | ++ |
| 9 | +++ | +++ |
| 10 | +++ | ++ |
| 11 | +++ | +++ |
| 12 | ++ | ++ |

TABLE 14-continued

BRM and BRG-1 Inhibition Data for Compounds of the Invention

| Compound # | BRM ATPase: $IC_{50}$ (μM) | BRG1 ATPase: $IC_{50}$ (μM) |
|---|---|---|
| 13 | +++ | +++ |
| 14 | ++ | ++ |
| 15 | ++ | ++ |
| 16 | ++ | ++ |
| 17 | +++ | +++ |
| 18 | ++ | ++ |
| 19 | ++ | ++ |
| 20 | ++ | ++ |
| 21 | ++ | ++ |
| 22 | ++ | + |
| 23 | ++ | ++ |
| 24 | ++ | ++ |
| 25 | ++ | ++ |
| 26 | ++ | + |
| 27 | ++ | ++ |
| 28 | +++ | +++ |
| 29 | ++ | ++ |
| 30 | +++ | ++ |
| 31 | +++ | +++ |
| 32 | +++ | +++ |
| 33 | +++ | +++ |
| 34 | +++ | +++ |
| 35 | +++ | ++ |
| 36 | ++ | ++ |
| 37 | ++ | ++ |
| 38 | ++ | ++ |
| 39 | ++ | ++ |
| 40 | ++ | ++ |
| 41 | +++ | +++ |
| 42 | +++ | +++ |
| 43 | ++ | ++ |
| 44 | +++ | +++ |
| 45 | +++ | ++ |
| 46 | +++ | ++ |
| 47 | +++ | +++ |
| 48 | +++ | +++ |
| 49 | +++ | +++ |
| 50 | +++ | ++ |
| 51 | +++ | ++ |
| 52 | +++ | +++ |
| 53 | ++ | ++ |
| 54 | ++ | ++ |
| 55 | ++ | ++ |
| 56 | +++ | +++ |
| 57 | +++ | +++ |
| 58 | +++ | ++ |
| 59 | ++ | ++ |
| 60 | +++ | ++ |
| 61 | ++ | ++ |
| 62 | ++ | ++ |
| 63 | ++ | ++ |
| 64 | +++ | ++ |
| 65 | ++ | ++ |
| 66 | + | + |
| 67 | ++ | ++ |
| 68 | ++ | ++ |
| 69 | +++ | ++ |
| 70 | ++ | ++ |
| 71 | +++. | ++ |
| 72 | ++ | ++ |
| 73 | ++ | ++ |
| 75 | +++ | ++ |
| 76 | ++++ | +++ |
| 77 | +++ | +++ |
| 78 | +++ | ++ |
| 79 | +++ | +++ |
| 80 | +++ | ++ |
| 81 | – | – |

TABLE 14-continued

| BRM and BRG-1 Inhibition Data for Compounds of the Invention | | |
|---|---|---|
| Compound # | BRM ATPase: $IC_{50}$ (μM) | BRG1 ATPase: $IC_{50}$ (μM) |
| 82 | +++ | ++ |
| 83 | – | – |

"+" indicates inhibitory effect of >1 μM;
"++" indicates inhibitory effect of 0.1-1 μM;
"+++" indicates inhibitory effect of 0.01-0.1 μM,
"++++" indicates inhibitory effect of <0.01 μM In Table 14, compound 83 is a control compound of the following structure:

83

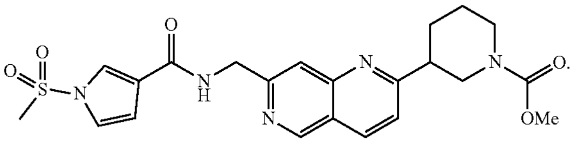

Other Embodiments

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A compound having the structure:

Formula I

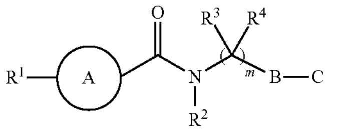

wherein $R^1$ is optionally substituted $C_1$-$C_6$ acyl, optionally substituted $C_1$-$C_6$ alkyl, optionally substituted $C_1$-$C_6$ heteroalkyl, optionally substituted $C_3$-$C_8$ cycloalkyl, optionally substituted $C_2$-$C_9$ heterocyclyl, optionally substituted amino, or —$SO_2R^5$;

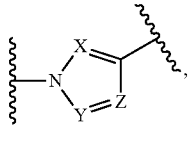, is

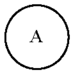

wherein each X, Y, and Z is, independently, N or $CR^8$, wherein $R^8$ is H or $C_1$-$C_6$ alkyl;

m is 1, 2, or 3;

B is an optionally substituted 6- to 10-membered bicyclic heteroarylene;

C is optionally substituted 3- to 10-membered cycloalkyl, optionally substituted 6- to 10-membered aryl, optionally substituted 5- to 10-membered heteroaryl, or optionally substituted 5- to 10-membered heterocyclyl;

$R^2$ is hydrogen or optionally substituted $C_1$-$C_6$ alkyl;

each of $R^3$ and $R^4$ is, independently, hydrogen, optionally substituted $C_1$-$C_6$ alkyl, or optionally substituted $C_1$-$C_6$ heteroalkyl;

$R^5$ is optionally substituted $C_1$-$C_6$ alkyl or —$NR^6R^7$; and each of $R^6$ and $R^7$ is, independently, optionally substituted $C_1$-$C_6$ alkyl, or a pharmaceutically acceptable salt thereof.

2. The compound of claim 1, wherein $R^2$ is hydrogen.

3. The compound of claim 1, wherein m is 1.

4. The compound of claim 1, wherein $R^4$ is hydrogen.

5. The compound of claim 1, wherein $R^3$ is hydrogen.

6. The compound of claim 1, wherein $R^3$ is optionally substituted $C_1$-$C_6$ alkyl.

7. The compound of claim 1, wherein $R^3$ is optionally substituted $C_1$-$C_6$ heteroalkyl.

8. The compound of claim 1, wherein B is a 9- or 10-membered heteroarylene.

9. The compound of claim 1, wherein C is optionally substituted $C_3$-$C_{10}$ cycloalkyl.

10. The compound of claim 1, wherein C is optionally substituted $C_6$-$C_{10}$ aryl.

11. The compound of claim 1, wherein C is optionally substituted 5- to 10-membered heteroaryl.

12. The compound of claim 1, wherein C is optionally substituted 5- to 10-membered heterocyclyl.

13. The compound of claim 1, wherein the compound is any one of Compounds:

| # | Compound |
|---|---|
| 2 | 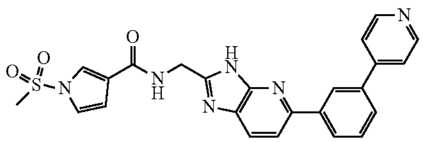 [SMILES: CS(=O)(=O)n1ccc(C(=O)NCc2nc3ccc(-c4cccc(-c5ccncc5)c4)nc3[nH]2)c1] |
| 3 | 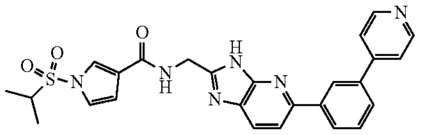 [SMILES: CC(C)S(=O)(=O)n1ccc(C(=O)NCc2nc3ccc(-c4cccc(-c5ccncc5)c4)nc3[nH]2)c1] |
| 4 | 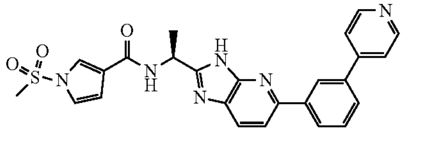 [SMILES: C[C@H](NC(=O)c1ccn(S(C)(=O)=O)c1)c1nc2ccc(-c3cccc(-c4ccncc4)c3)nc2[nH]1] |

-continued
| # | Compound |
|---|---|
| 5 | 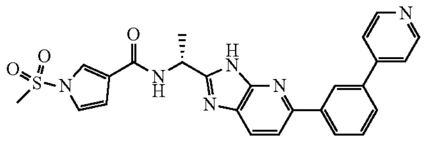 [SMILES: C[C@@H](NC(=O)c1ccn(S(C)(=O)=O)c1)c1nc2ccc(-c3cccc(-c4ccncc4)c3)nc2[nH]1] |
| 6 | 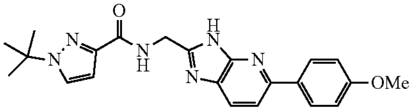 [SMILES: COc1ccc(-c2ccc3nc(CNC(=O)c4ccn(C(C)(C)C)n4)[nH]c3n2)cc1] |
| 7 | 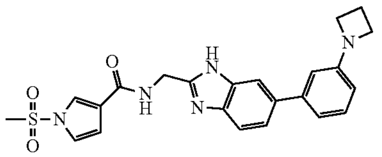 [SMILES: CS(=O)(=O)n1ccc(C(=O)NCc2nc3ccc(-c4cccc(N5CCC5)c4)cc3[nH]2)c1] |
| 8 | 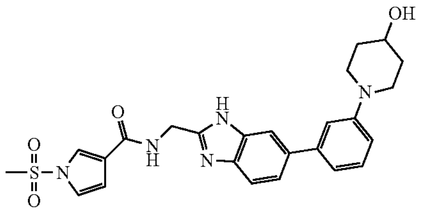 [SMILES: CS(=O)(=O)n1ccc(C(=O)NCc2nc3ccc(-c4cccc(N5CCC(O)CC5)c4)cc3[nH]2)c1] |
| 9 | 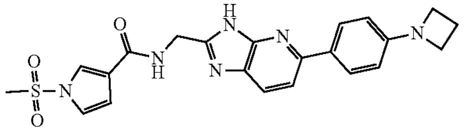 [SMILES: CS(=O)(=O)n1ccc(C(=O)NCc2nc3ccc(-c4ccc(N5CCC5)cc4)nc3[nH]2)c1] |
| 10 | 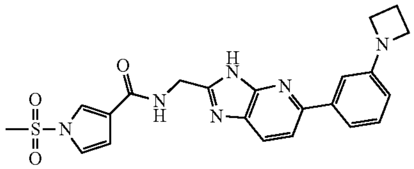 [SMILES: CS(=O)(=O)n1ccc(C(=O)NCc2nc3ccc(-c4cccc(N5CCC5)c4)nc3[nH]2)c1] |
| 11 | 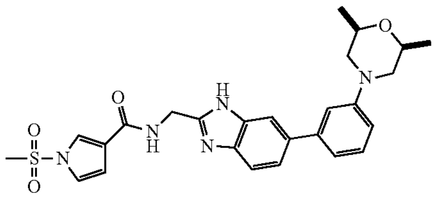 |
| 12 | 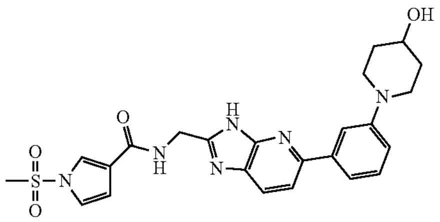 [SMILES: CS(=O)(=O)n1ccc(C(=O)NCc2nc3ccc(-c4cccc(N5CCC(O)CC5)c4)nc3[nH]2)c1] |
-continued
| # | Compound |
|---|---|
| 13 | 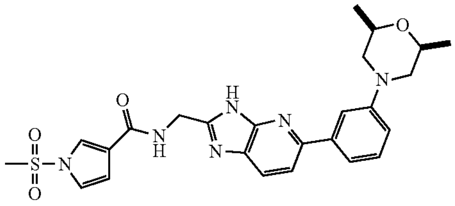 |
| 14 | 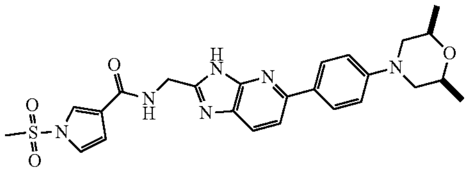 |
| 15 | 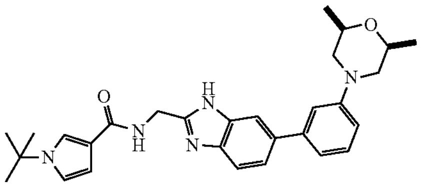 [SMILES: C[C@@H]1CN(c2cccc(-c3ccc4nc(CNC(=O)c5ccn(C(C)(C)C)c5)[nH]c4c3)c2)C[C@H](C)O1] |
| 16 | 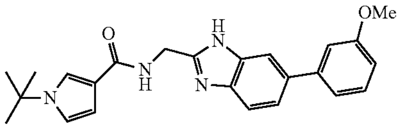 [SMILES: COc1cccc(-c2ccc3nc(CNC(=O)c4ccn(C(C)(C)C)c4)[nH]c3c2)c1] |
| 17 | 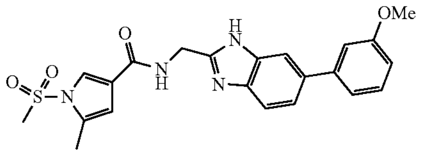 [SMILES: COc1cccc(-c2ccc3nc(CNC(=O)c4cc(C)n(S(C)(=O)=O)c4)[nH]c3c2)c1] |
| 18 | 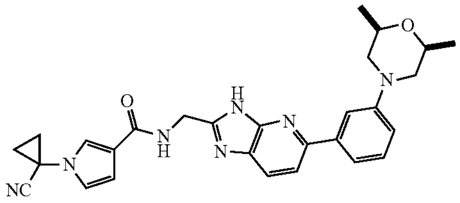 [SMILES: C[C@@H]1CN(c2cccc(-c3ccc4nc(CNC(=O)c5ccn(C6(C#N)CC6)c5)[nH]c4n3)c2)C[C@H](C)O1] |
| 19 | 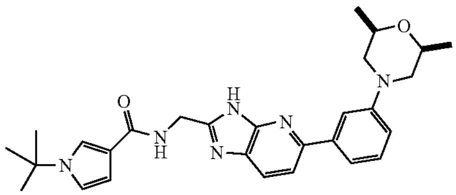 [SMILES: C[C@@H]1CN(c2cccc(-c3ccc4nc(CNC(=O)c5ccn(C(C)(C)C)c5)[nH]c4n3)c2)C[C@H](C)O1] |
| 20 | 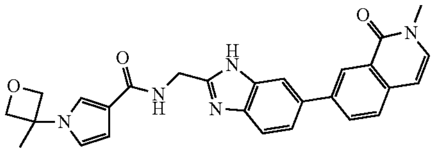 [SMILES: Cn1ccc2ccc(-c3ccc4nc(CNC(=O)c5ccn(C6(C)COC6)c5)[nH]c4c3)cc2c1=O] |

-continued
| # | Compound |
|---|---|
| 21 | 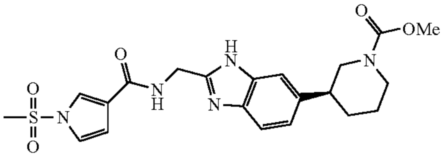 [SMILES: COC(=O)N1CCC[C@@H](c2ccc3nc(CNC(=O)c4ccn(S(C)(=O)=O)c4)[nH]c3c2)C1] |
| 22 | 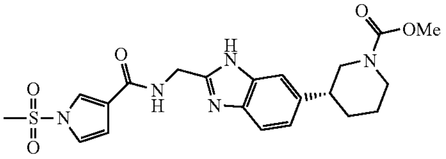 [SMILES: COC(=O)N1CCC[C@H](c2ccc3nc(CNC(=O)c4ccn(S(C)(=O)=O)c4)[nH]c3c2)C1] |
| 23 | 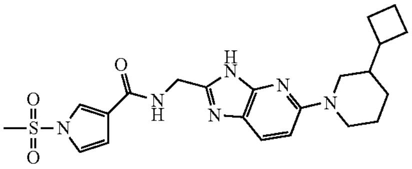 [SMILES: CS(=O)(=O)n1ccc(C(=O)NCc2nc3ccc(N4CCCC(C5CCC5)C4)nc3[nH]2)c1] |
| 24 | 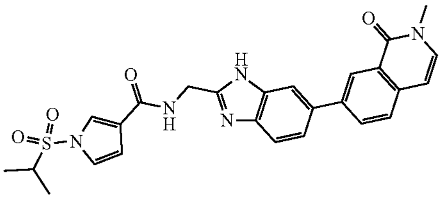 [SMILES: CC(C)S(=O)(=O)n1ccc(C(=O)NCc2nc3ccc(-c4ccc5ccn(C)c(=O)c5c4)cc3[nH]2)c1] |
| 25 | 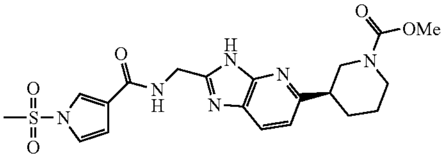 [SMILES: COC(=O)N1CCC[C@@H](c2ccc3nc(CNC(=O)c4ccn(S(C)(=O)=O)c4)[nH]c3n2)C1] |
| 26 | 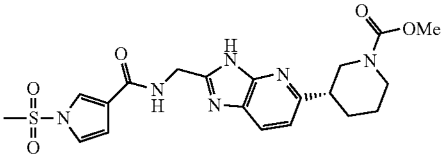 [SMILES: COC(=O)N1CCC[C@H](c2ccc3nc(CNC(=O)c4ccn(S(C)(=O)=O)c4)[nH]c3n2)C1] |
| 27 | 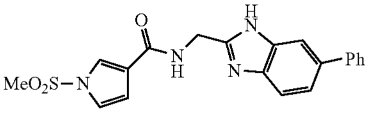 [SMILES: CS(=O)(=O)n1ccc(C(=O)NCc2nc3ccc(-c4ccccc4)cc3[nH]2)c1] |
| 28 | 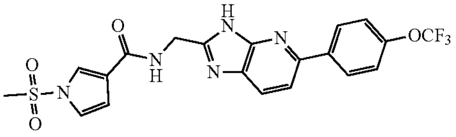 [SMILES: CS(=O)(=O)n1ccc(C(=O)NCc2nc3ccc(-c4ccc(OC(F)(F)F)cc4)nc3[nH]2)c1] |
| 29 | 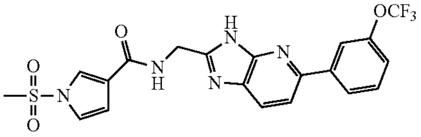 [SMILES: CS(=O)(=O)n1ccc(C(=O)NCc2nc3ccc(-c4cccc(OC(F)(F)F)c4)nc3[nH]2)c1] |
-continued
| # | Compound |
|---|---|
| 30 | 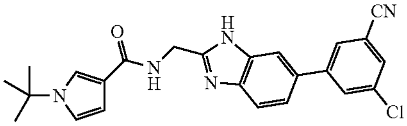 [SMILES: CC(C)(C)n1ccc(C(=O)NCc2nc3ccc(-c4cc(Cl)cc(C#N)c4)cc3[nH]2)c1] |
| 31 | 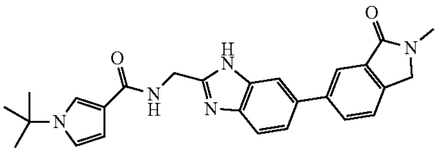 [SMILES: CN1Cc2ccc(-c3ccc4nc(CNC(=O)c5ccn(C(C)(C)C)c5)[nH]c4c3)cc2C1=O] |
| 32 | 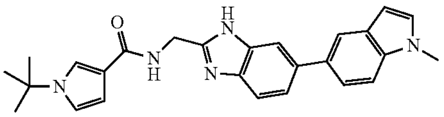 [SMILES: Cn1ccc2cc(-c3ccc4nc(CNC(=O)c5ccn(C(C)(C)C)c5)[nH]c4c3)ccc21] |
| 33 | 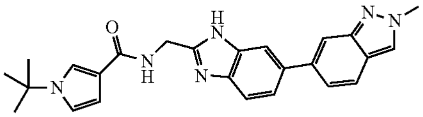 [SMILES: Cn1cc2ccc(-c3ccc4nc(CNC(=O)c5ccn(C(C)(C)C)c5)[nH]c4c3)cc2n1] |
| 34 | 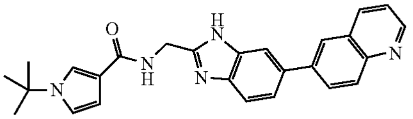 [SMILES: CC(C)(C)n1ccc(C(=O)NCc2nc3ccc(-c4ccc5ncccc5c4)cc3[nH]2)c1] |
| 35 | 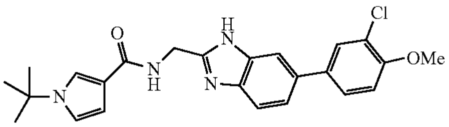 [SMILES: COc1ccc(-c2ccc3nc(CNC(=O)c4ccn(C(C)(C)C)c4)[nH]c3c2)cc1Cl] |
| 36 | 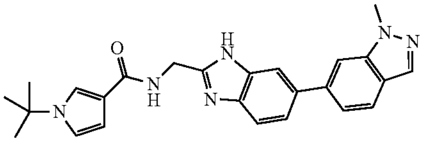 [SMILES: Cn1ncc2ccc(-c3ccc4nc(CNC(=O)c5ccn(C(C)(C)C)c5)[nH]c4c3)cc21] |
| 37 | 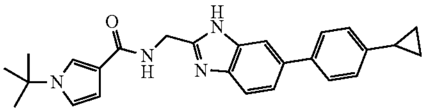 [SMILES: CC(C)(C)n1ccc(C(=O)NCc2nc3ccc(-c4ccc(C5CC5)cc4)cc3[nH]2)c1] |
| 38 | 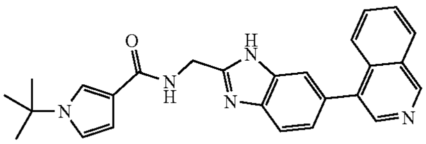 [SMILES: CC(C)(C)n1ccc(C(=O)NCc2nc3ccc(-c4cncc5ccccc45)cc3[nH]2)c1] |
| 39 | 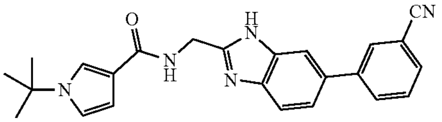 [SMILES: CC(C)(C)n1ccc(C(=O)NCc2nc3ccc(-c4cccc(C#N)c4)cc3[nH]2)c1] |
| 40 | 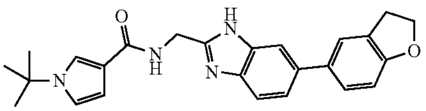 [SMILES: CC(C)(C)n1ccc(C(=O)NCc2nc3ccc(-c4ccc5c(c4)CCO5)cc3[nH]2)c1] |

-continued
| # | Compound |
|---|---|
| 41 | 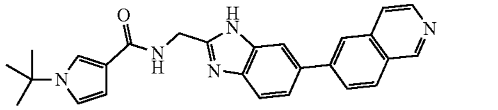 [SMILES: CC(C)(C)n1ccc(C(=O)NCc2nc3ccc(-c4ccc5cnccc5c4)cc3[nH]2)c1] |
| 42 | 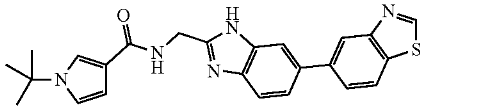 [SMILES: CC(C)(C)n1ccc(C(=O)NCc2nc3ccc(-c4ccc5scnc5c4)cc3[nH]2)c1] |
| 43 | 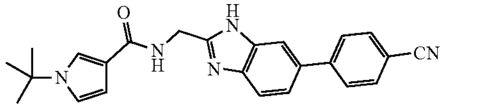 [SMILES: CC(C)(C)n1ccc(C(=O)NCc2nc3ccc(-c4ccc(C#N)cc4)cc3[nH]2)c1] |
| 44 | 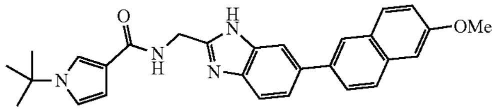 [SMILES: COc1ccc2cc(-c3ccc4nc(CNC(=O)c5ccn(C(C)(C)C)c5)[nH]c4c3)ccc2c1] |
| 45 | 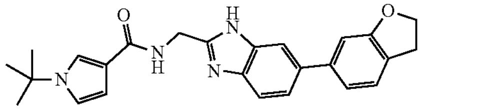 [SMILES: CC(C)(C)n1ccc(C(=O)NCc2nc3ccc(-c4ccc5c(c4)OCC5)cc3[nH]2)c1] |
| 46 | 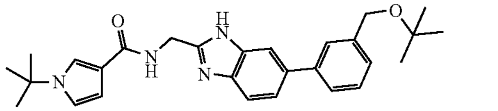 [SMILES: CC(C)(C)OCc1cccc(-c2ccc3nc(CNC(=O)c4ccn(C(C)(C)C)c4)[nH]c3c2)c1] |
| 47 | 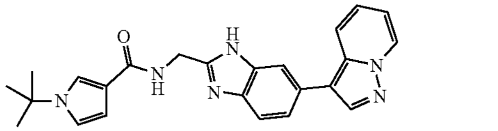 [SMILES: CC(C)(C)n1ccc(C(=O)NCc2nc3ccc(-c4cnn5ccccc45)cc3[nH]2)c1] |
| 48 | 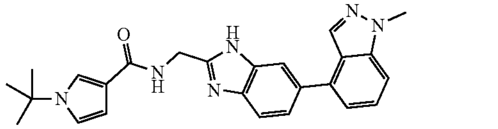 [SMILES: Cn1ncc2c(-c3ccc4nc(CNC(=O)c5ccn(C(C)(C)C)c5)[nH]c4c3)cccc21] |
| 49 | 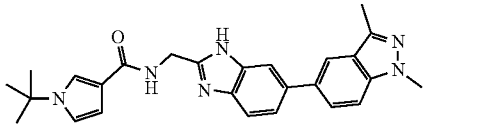 [SMILES: Cc1nn(C)c2ccc(-c3ccc4nc(CNC(=O)c5ccn(C(C)(C)C)c5)[nH]c4c3)cc12] |
| 50 | 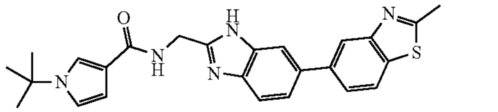 [SMILES: Cc1nc2cc(-c3ccc4nc(CNC(=O)c5ccn(C(C)(C)C)c5)[nH]c4c3)ccc2s1] |
| 51 | 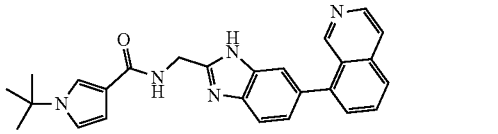 [SMILES: CC(C)(C)n1ccc(C(=O)NCc2nc3ccc(-c4cccc5ccncc45)cc3[nH]2)c1] |
| 52 | 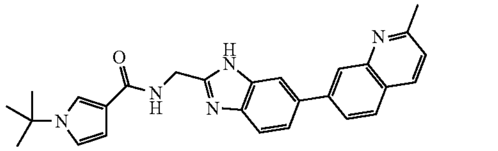 [SMILES: Cc1ccc2ccc(-c3ccc4nc(CNC(=O)c5ccn(C(C)(C)C)c5)[nH]c4c3)cc2n1] |
-continued
| # | Compound |
|---|---|
| 53 | 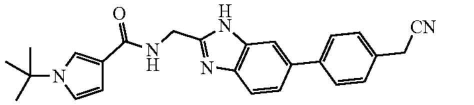 [SMILES: CC(C)(C)n1ccc(C(=O)NCc2nc3ccc(-c4ccc(CC#N)cc4)cc3[nH]2)c1] |
| 54 | 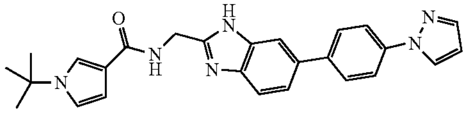 [SMILES: CC(C)(C)n1ccc(C(=O)NCc2nc3ccc(-c4ccc(-n5cccn5)cc4)cc3[nH]2)c1] |
| 55 | 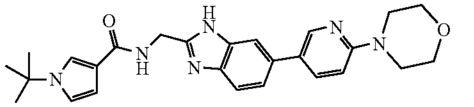 [SMILES: CC(C)(C)n1ccc(C(=O)NCc2nc3ccc(-c4ccc(N5CCOCC5)nc4)cc3[nH]2)c1] |
| 56 | 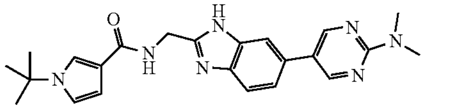 [SMILES: CN(C)c1ncc(-c2ccc3nc(CNC(=O)c4ccn(C(C)(C)C)c4)[nH]c3c2)cn1] |
| 57 | 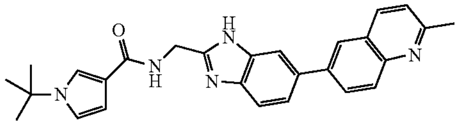 [SMILES: Cc1ccc2cc(-c3ccc4nc(CNC(=O)c5ccn(C(C)(C)C)c5)[nH]c4c3)ccc2n1] |
| 58 | 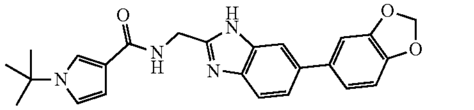 [SMILES: CC(C)(C)n1ccc(C(=O)NCc2nc3ccc(-c4ccc5c(c4)OCO5)cc3[nH]2)c1] |
| 59 | 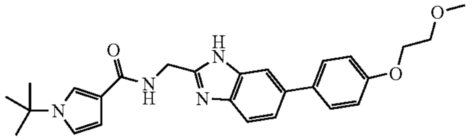 [SMILES: COCCOc1ccc(-c2ccc3nc(CNC(=O)c4ccn(C(C)(C)C)c4)[nH]c3c2)cc1] |
| 60 | 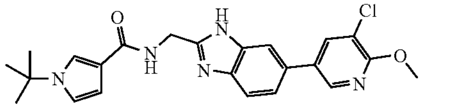 [SMILES: COc1ncc(-c2ccc3nc(CNC(=O)c4ccn(C(C)(C)C)c4)[nH]c3c2)cc1Cl] |
| 61 | 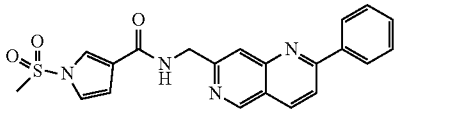 [SMILES: CS(=O)(=O)n1ccc(C(=O)NCc2cc3nc(-c4ccccc4)ccc3cn2)c1] |
| 62 | 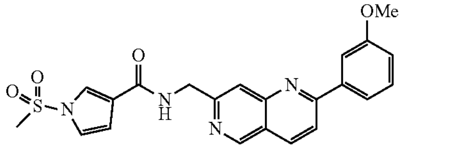 [SMILES: COc1cccc(-c2ccc3cnc(CNC(=O)c4ccn(S(C)(=O)=O)c4)cc3n2)c1] |
| 63 | 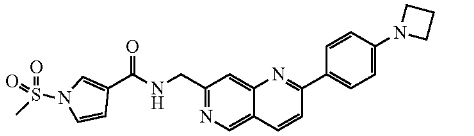 [SMILES: CS(=O)(=O)n1ccc(C(=O)NCc2cc3nc(-c4ccc(N5CCC5)cc4)ccc3cn2)c1] |
| 64 | 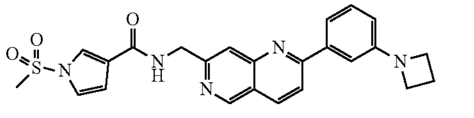 [SMILES: CS(=O)(=O)n1ccc(C(=O)NCc2cc3nc(-c4cccc(N5CCC5)c4)ccc3cn2)c1] |

-continued
| # | Compound |
|---|---|
| 65 | 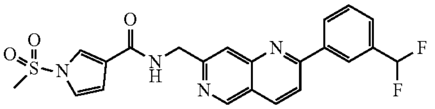 [SMILES: CS(=O)(=O)n1ccc(C(=O)NCc2cc3nc(-c4cccc(C(F)F)c4)ccc3cn2)c1] |
| 66 | 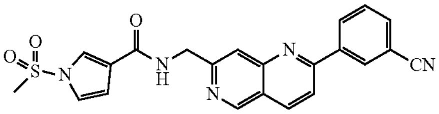 [SMILES: CS(=O)(=O)n1ccc(C(=O)NCc2cc3nc(-c4cccc(C#N)c4)ccc3cn2)c1] |
| 67 | 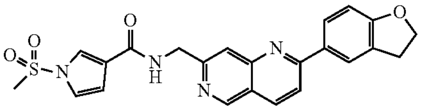 [SMILES: CS(=O)(=O)n1ccc(C(=O)NCc2cc3nc(-c4ccc5c(c4)CCO5)ccc3cn2)c1] |
| 68 | 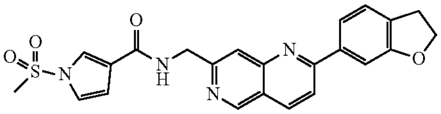 [SMILES: CS(=O)(=O)n1ccc(C(=O)NCc2cc3nc(-c4ccc5c(c4)OCC5)ccc3cn2)c1] |
| 69 | 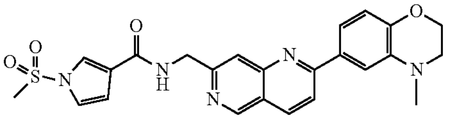 [SMILES: CN1CCOc2ccc(-c3ccc4cnc(CNC(=O)c5ccn(S(C)(=O)=O)c5)cc4n3)cc21] |
| 70 | 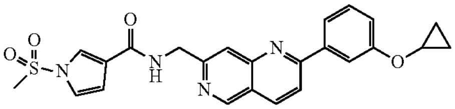 [SMILES: CS(=O)(=O)n1ccc(C(=O)NCc2cc3nc(-c4cccc(OC5CC5)c4)ccc3cn2)c1] |
| 71 | 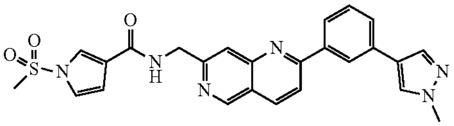 [SMILES: Cn1cc(-c2cccc(-c3ccc4cnc(CNC(=O)c5ccn(S(C)(=O)=O)c5)cc4n3)c2)cn1] |
| 72 | 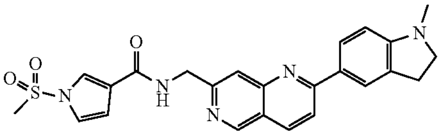 [SMILES: CN1CCc2cc(-c3ccc4cnc(CNC(=O)c5ccn(S(C)(=O)=O)c5)cc4n3)ccc21] |
| 73 | 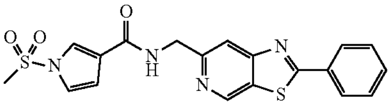 [SMILES: CS(=O)(=O)n1ccc(C(=O)NCc2cc3nc(-c4ccccc4)sc3cn2)c1] |
| 74 | 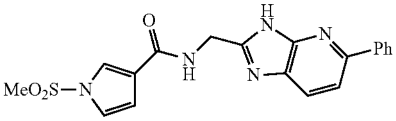 [SMILES: CS(=O)(=O)n1ccc(C(=O)NCc2nc3ccc(-c4ccccc4)nc3[nH]2)c1] |
| 75 | 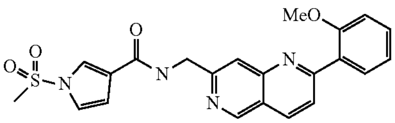 [SMILES: COc1ccccc1-c1ccc2cnc(CNC(=O)c3ccn(S(C)(=O)=O)c3)cc2n1] |
| 76 | 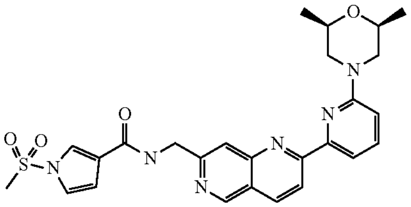 |
| 77 | 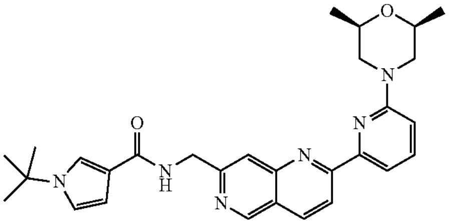 [SMILES: C[C@@H]1CN(c2cccc(-c3ccc4cnc(CNC(=O)c5ccn(C(C)(C)C)c5)cc4n3)n2)C[C@H](C)O1] |
| 78 | 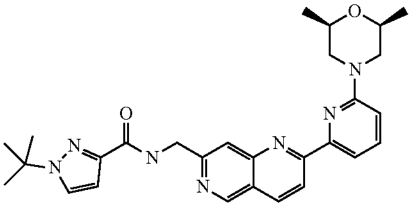 [SMILES: C[C@@H]1CN(c2cccc(-c3ccc4cnc(CNC(=O)c5ccn(C(C)(C)C)n5)cc4n3)n2)C[C@H](C)O1] |
| 79 | 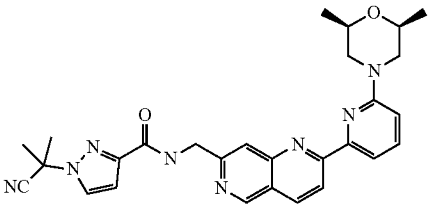 [SMILES: C[C@@H]1CN(c2cccc(-c3ccc4cnc(CNC(=O)c5ccn(C(C)(C)C#N)n5)cc4n3)n2)C[C@H](C)O1] |
| 80 | 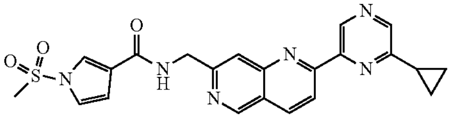 [SMILES: CS(=O)(=O)n1ccc(C(=O)NCc2cc3nc(-c4cncc(C5CC5)n4)ccc3cn2)c1] |
| 81 | 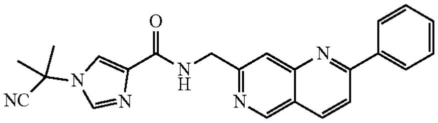 [SMILES: CC(C)(C#N)n1cnc(C(=O)NCc2cc3nc(-c4ccccc4)ccc3cn2)c1] |
| 82 | 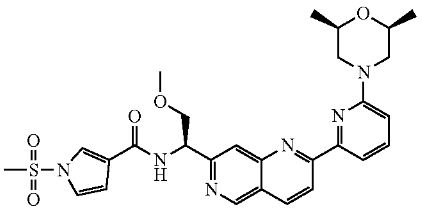 |
14. A pharmaceutical composition comprising a compound of claim 1 and a pharmaceutically acceptable excipient.
* * * * *